US011504282B2

(12) United States Patent
Raycheck et al.

(10) Patent No.: US 11,504,282 B2
(45) Date of Patent: *Nov. 22, 2022

(54) ABSORBENT ARTICLE WITH LEG CUFFS

(71) Applicant: The Procter & Gamble Company, Cincinnati, OH (US)

(72) Inventors: Jeromy Thomas Raycheck, South Lebanon, OH (US); Abhishek Prakash Surushe, Schwalbach am Taunus (DE); Cornelia Beate Martynus, Nidderau-Ostheim (DE); Donald Carroll Roe, West Chester, OH (US); Ernesto Gabriel Bianchi, Oberursel (DE); Bruno Johannes Ehrnsperger, Bad Soden (DE)

(73) Assignee: The Procter & Gamble Company, Cincinnati, OH (US)

( * ) Notice: Subject to any disclaimer, the term of this patent is extended or adjusted under 35 U.S.C. 154(b) by 379 days.

This patent is subject to a terminal disclaimer.

(21) Appl. No.: 16/693,457

(22) Filed: Nov. 25, 2019

(65) Prior Publication Data

US 2020/0107972 A1 Apr. 9, 2020

Related U.S. Application Data

(63) Continuation of application No. 15/074,583, filed on Mar. 18, 2016, now Pat. No. 10,531,990.
(Continued)

(51) Int. Cl.
*A61F 13/49* (2006.01)
*A61F 13/494* (2006.01)
(Continued)

(52) U.S. Cl.
CPC .. *A61F 13/49007* (2013.01); *A61F 13/49001* (2013.01); *A61F 13/495* (2013.01);
(Continued)

(58) Field of Classification Search
CPC .......... A61F 13/49001; A61F 13/49007; A61F 13/49011; A61F 13/4942; A61F 13/495;
(Continued)

(56) References Cited

U.S. PATENT DOCUMENTS 3,848,594 A 11/1974 Buell
3,860,003 A 1/1975 Buell
(Continued)

FOREIGN PATENT DOCUMENTS

CA 2922316 A1 3/2015
CN 1047970 A 12/1990
(Continued)

OTHER PUBLICATIONS

All Office Actions; U.S. Appl. No. 16/663,763, filed on Oct. 25, 2019.
(Continued)

*Primary Examiner* — Michele M Kidwell
(74) *Attorney, Agent, or Firm* — Daniel S. Albrecht

(57) ABSTRACT

A disposable absorbent article may include a chassis that includes a topsheet, a backsheet, and an absorbent core disposed between the topsheet and the backsheet; and a leg gasketing system. The leg gasketing system may include an inner cuff and an outer cuff; the inner cuff may include an inner cuff folded edge and an inner cuff material edge and the outer cuff may include an outer cuff folded edge and an outer cuff material edge such that the web of material is folded laterally inward to form the outer cuff folded edge and folded laterally outward to form the inner cuff folded edge, and the leg gasketing system further including a leg gasketing system pocket with an opening on an inboard longitudinal edge of the leg gasketing system pocket. The disposable absorbent article also includes at least one channel in the absorbent core.

20 Claims, 23 Drawing Sheets

Related U.S. Application Data

(60) Provisional application No. 62/134,628, filed on Mar. 18, 2015.

(51) Int. Cl.
| | |
|---|---|
| *A61F 13/495* | (2006.01) |
| *A61F 13/532* | (2006.01) |
| *A61F 13/537* | (2006.01) |
| *A61F 13/551* | (2006.01) |
| *A61F 13/531* | (2006.01) |
| *A61F 13/53* | (2006.01) |
| *A61F 13/539* | (2006.01) |

(52) U.S. Cl.
CPC .... *A61F 13/49011* (2013.01); *A61F 13/4942* (2013.01); *A61F 13/531* (2013.01); *A61F 13/5323* (2013.01); *A61F 13/53717* (2013.01); *A61F 13/55105* (2013.01); *A61F 2013/49092* (2013.01); *A61F 2013/5315* (2013.01); *A61F 2013/53051* (2013.01); *A61F 2013/5395* (2013.01); *A61F 2013/53908* (2013.01)

(58) Field of Classification Search
CPC ........... A61F 13/531; A61F 13/5323; A61F 13/53717; A61F 13/55105; A61F 2013/49092; A61F 2013/53051; A61F 2013/5315; A61F 2013/53908; A61F 2013/5395

See application file for complete search history.

(56) References Cited

U.S. PATENT DOCUMENTS

| | | |
|---|---|---|
| 4,055,182 A | 10/1977 | Mack |
| 4,324,245 A | 4/1982 | Mesek |
| 4,552,795 A | 11/1985 | Hansen et al. |
| 4,610,678 A | 9/1986 | Weisman et al. |
| 4,639,390 A | 1/1987 | Shoji et al. |
| 4,662,875 A | 5/1987 | Hirotsu et al. |
| 4,673,402 A | 6/1987 | Weisman et al. |
| 4,699,622 A | 10/1987 | Toussant et al. |
| 4,738,677 A | 4/1988 | Foreman |
| 4,753,646 A | 6/1988 | Enloe |
| 4,808,178 A | 2/1989 | Aziz et al. |
| 4,808,252 A | 2/1989 | Lash |
| 4,816,025 A | 3/1989 | Foreman |
| 4,834,735 A | 5/1989 | Alemany et al. |
| 4,846,815 A | 7/1989 | Scripps |
| 4,850,990 A | 7/1989 | Huntoon |
| 4,883,549 A | 11/1989 | Frost et al. |
| 4,888,231 A | 12/1989 | Angstadt |
| 4,892,536 A | 1/1990 | Des Marais et al. |
| 4,894,060 A | 1/1990 | Nestegard |
| 4,909,803 A | 3/1990 | Aziz et al. |
| 4,923,660 A | 5/1990 | Willenberg et al. |
| 4,938,754 A | 7/1990 | Mesek |
| 4,938,755 A | 7/1990 | Foreman |
| 4,946,527 A | 8/1990 | Battrell |
| 4,963,140 A | 10/1990 | Robertson et al. |
| 4,990,147 A | 2/1991 | Freeland |
| 5,021,051 A | 6/1991 | Hiuke |
| 5,026,364 A | 6/1991 | Robertson |
| 5,037,416 A | 8/1991 | Allen et al. |
| 5,061,261 A | 10/1991 | Suzuki et al. |
| 5,137,537 A | 8/1992 | Herron et al. |
| 5,147,345 A | 9/1992 | Young et al. |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,171,391 A | 12/1992 | Chmielewski et al. |
| 5,187,817 A | 2/1993 | Zolner |
| 5,196,000 A | 3/1993 | Clear et al. |
| 5,221,274 A | 6/1993 | Buell et al. |
| 5,242,436 A | 9/1993 | Weil et al. |
| 5,260,345 A | 11/1993 | Des Marais et al. |
| 5,269,775 A | 12/1993 | Freeland et al. |
| 5,281,207 A | 1/1994 | Chmielewski et al. |
| 5,342,338 A | 8/1994 | Roe |
| 5,358,500 A | 10/1994 | LaVon et al. |
| 5,387,207 A | 2/1995 | Dyer et al. |
| 5,397,316 A | 3/1995 | LaVon et al. |
| 5,397,318 A | 3/1995 | Dreier |
| 5,415,644 A | 5/1995 | Enloe |
| 5,482,625 A | 1/1996 | Kenishi et al. |
| 5,486,418 A | 1/1996 | Ohmory et al. |
| 5,499,978 A | 3/1996 | Buell et al. |
| 5,507,736 A | 4/1996 | Clear et al. |
| 5,531,730 A | 7/1996 | Dreier |
| 5,540,671 A | 7/1996 | Dreier |
| 5,545,158 A | 8/1996 | Jessup |
| 5,554,145 A | 9/1996 | Roe et al. |
| 5,558,660 A | 9/1996 | Dreier |
| 5,558,661 A | 9/1996 | Roe et al. |
| 5,567,254 A | 10/1996 | Sagaser |
| 5,569,227 A | 10/1996 | Vandemoortele et al. |
| 5,569,234 A | 10/1996 | Buell et al. |
| 5,571,096 A | 11/1996 | Dobrin et al. |
| 5,575,785 A | 11/1996 | Gryskiewicz et al. |
| 5,576,090 A | 11/1996 | Suzuki |
| 5,580,411 A | 12/1996 | Nease et al. |
| 5,584,828 A | 12/1996 | Yamamoto et al. |
| 5,591,152 A | 1/1997 | Buell et al. |
| 5,593,401 A | 1/1997 | Sosalla et al. |
| 5,601,543 A | 2/1997 | Dreier et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,643,243 A | 7/1997 | Klemp |
| 5,643,588 A | 7/1997 | Roe et al. |
| 5,694,918 A | 7/1997 | Schleinz |
| 5,672,166 A | 9/1997 | Vandemoortele |
| 5,674,215 A | 10/1997 | Ronnberg |
| 5,681,302 A | 10/1997 | Melbye et al. |
| 5,695,488 A | 12/1997 | Sosalla |
| 5,749,865 A | 5/1998 | Yamamoto et al. |
| 5,769,838 A | 6/1998 | Buell et al. |
| 5,827,259 A | 10/1998 | Laux et al. |
| 5,827,387 A | 10/1998 | Reynolds et al. |
| 5,833,677 A | 11/1998 | Sauer |
| 5,865,823 A | 2/1999 | Curro |
| 5,879,341 A | 3/1999 | Odorzynski et al. |
| 5,895,382 A | 4/1999 | Popp et al. |
| 5,899,895 A | 5/1999 | Robles et al. |
| 5,904,675 A | 5/1999 | Laux et al. |
| 5,911,713 A | 6/1999 | Yamada et al. |
| 5,931,825 A | 8/1999 | Kuen et al. |
| 5,931,826 A | 8/1999 | Faulks et al. |
| 5,938,652 A | 8/1999 | Sauer |
| 5,942,179 A | 8/1999 | Tailentire et al. |
| 5,993,433 A | 11/1999 | St. Louis et al. |
| 6,004,306 A | 12/1999 | Robles et al. |
| 6,107,537 A | 8/2000 | Elder et al. |
| 6,117,121 A | 9/2000 | Faluks et al. |
| 6,120,486 A | 9/2000 | Toyoda et al. |
| 6,120,487 A | 9/2000 | Ashton |
| 6,123,694 A | 9/2000 | Pieniak et al. |
| 6,132,410 A | 10/2000 | Van Gompel et al. |
| 6,135,988 A | 10/2000 | Turner et al. |
| 6,140,551 A | 10/2000 | Niemeyer et al. |
| 6,142,985 A | 11/2000 | Feist |
| 6,152,906 A | 11/2000 | Faulks et al. |
| 6,171,290 B1 | 1/2001 | Boisse et al. |
| 6,174,302 B1 | 1/2001 | Kumasaka |
| 6,186,996 B1 | 2/2001 | Martin |
| 6,217,563 B1 | 4/2001 | Van Gompel et al. |
| 6,231,558 B1 | 5/2001 | Mosley |
| 6,248,097 B1 | 6/2001 | Beitz et al. |
| 6,258,076 B1 | 7/2001 | Glaug et al. |
| 6,264,639 B1 | 7/2001 | Sauer |
| 6,264,641 B1 | 7/2001 | Van Gompel et al. |

(56) References Cited

U.S. PATENT DOCUMENTS

| | | |
|---|---|---|
| 6,264,642 B1 | 7/2001 | Kuen et al. |
| 6,264,643 B1 | 7/2001 | Toyoda et al. |
| 6,280,426 B1 | 8/2001 | Turner et al. |
| 6,293,934 B1 | 9/2001 | Kumasaka |
| 6,312,420 B1 | 11/2001 | Sasaki et al. |
| 6,315,764 B1 | 11/2001 | Faulks et al. |
| 6,336,922 B1 | 1/2002 | Van Gompel et al. |
| 6,346,162 B1 | 2/2002 | Reynolds et al. |
| 6,364,863 B1 | 4/2002 | Yamamoto et al. |
| 6,375,646 B1 | 4/2002 | Widlund et al. |
| 6,413,249 B1 | 7/2002 | Turi et al. |
| 6,425,889 B1 | 7/2002 | Kitaoka et al. |
| 6,432,098 B1 | 8/2002 | Kline et al. |
| 6,436,216 B1 | 8/2002 | Grover |
| 6,440,117 B1 | 8/2002 | Itoh et al. |
| 6,440,239 B1 | 8/2002 | Vogt |
| 6,451,001 B1 | 9/2002 | Kumasaka |
| 6,461,342 B2 | 10/2002 | Tanji et al. |
| 6,478,785 B1 | 11/2002 | Ashton et al. |
| 6,491,677 B1 | 12/2002 | Glaug et al. |
| 6,494,872 B1 | 12/2002 | Suzuki et al. |
| 6,506,185 B1 | 1/2003 | Sauer et al. |
| 6,527,893 B1 | 3/2003 | Boisse et al. |
| 6,562,123 B2 | 4/2003 | Katayama et al. |
| 6,569,139 B1 | 5/2003 | Datta et al. |
| 6,569,140 B1 | 5/2003 | Mizutani et al. |
| 6,565,976 B1 | 7/2003 | Jitoe et al. |
| 6,592,562 B2 | 7/2003 | Menard et al. |
| 6,613,033 B1 | 9/2003 | Popp et al. |
| 6,629,967 B1 | 10/2003 | Simmons et al. |
| 6,638,262 B2 | 10/2003 | Suzuki et al. |
| 6,641,570 B2 | 11/2003 | Mishima et al. |
| 6,641,692 B2 | 11/2003 | Reynolds et al. |
| 6,659,990 B1 | 12/2003 | Odorzynski et la. |
| 6,682,515 B1 | 1/2004 | Mizutani et al. |
| 6,682,516 B2 | 1/2004 | Johnston et al. |
| 6,699,228 B1 | 3/2004 | Chmielewski et al. |
| 6,702,801 B2 | 3/2004 | Van Gompel et al. |
| 6,706,029 B1 | 3/2004 | Suzuki et al. |
| 6,706,030 B1 | 3/2004 | Okuda et al. |
| 6,767,343 B2 | 7/2004 | Shimada et al. |
| 6,767,344 B2 | 7/2004 | Suzuki |
| 6,808,582 B2 | 10/2004 | Popp et al. |
| 6,837,958 B2 | 1/2005 | Otsubo et al. |
| 6,840,930 B1 | 1/2005 | Miyamoto et al. |
| 6,884,310 B2 | 4/2005 | Roessler et al. |
| 6,903,793 B2 | 6/2005 | Ukegawa et al. |
| 6,921,394 B2 | 7/2005 | Yasushi et al. |
| 6,978,486 B2 | 12/2005 | Zhou et al. |
| 7,014,632 B2 | 3/2006 | Takino et al. |
| 7,018,368 B2 | 3/2006 | Van Gompel et al. |
| 7,037,300 B2 | 5/2006 | Kling |
| 7,135,014 B2 | 11/2006 | Sasaki et al. |
| 7,150,729 B2 | 12/2006 | Shimada et al. |
| 7,156,828 B2 | 1/2007 | Ostrow |
| 7,163,530 B1 | 1/2007 | Toyoshima et al. |
| 7,169,136 B2 | 1/2007 | Otsubo et al. |
| 7,189,219 B1 | 3/2007 | Kasai et al. |
| 7,195,621 B2 | 3/2007 | Ohnishi et al. |
| 7,207,978 B2 | 4/2007 | Takino et al. |
| 7,226,437 B2 | 6/2007 | Sasaki et al. |
| 7,264,686 B2 | 9/2007 | Thorson et al. |
| 7,291,138 B2 | 11/2007 | Hoshino et al. |
| 7,331,946 B2 | 2/2008 | Shimada et al. |
| 7,338,479 B2 | 3/2008 | Fujioka et al. |
| 7,378,360 B2 | 5/2008 | Clark et al. |
| 7,378,568 B2 | 5/2008 | Thomas et al. |
| 7,435,243 B2 | 10/2008 | Miyamoto |
| 7,435,244 B2 | 10/2008 | Schroer et al. |
| 7,527,616 B2 | 5/2009 | Miyamoto |
| 7,561,602 B1 | 7/2009 | Nakabayashi |
| 7,569,039 B2 | 8/2009 | Matsuda et al. |
| 7,604,625 B2 | 10/2009 | Turi et al. |
| 7,621,900 B2 | 11/2009 | Van Gompel et al. |
| 7,626,073 B2 | 12/2009 | Catalan |
| 7,666,176 B2 | 2/2010 | Erdman et al. |
| 7,670,325 B2 | 3/2010 | Sugiyama e al. |
| 7,708,725 B2 | 5/2010 | Kinoshita et al. |
| 7,722,590 B2 | 5/2010 | Tsuji et al. |
| 7,722,591 B2 | 5/2010 | Back |
| 7,727,214 B2 | 6/2010 | Torigoshi et al. |
| 7,727,215 B2 | 6/2010 | Kenmochi et al. |
| 7,744,576 B2 | 6/2010 | Busam et al. |
| 7,744,579 B2 | 6/2010 | Langdon et al. |
| 7,750,203 B2 | 7/2010 | Becker et al. |
| 7,753,899 B2 | 7/2010 | Mori et al. |
| 7,754,040 B2 | 7/2010 | Norrby |
| 7,785,309 B2 | 8/2010 | Van Gompel et al. |
| 7,794,441 B2 | 9/2010 | Ashton et al. |
| 7,834,236 B2 | 11/2010 | Middlesworth et al. |
| 7,838,724 B2 | 11/2010 | Van Gompel et al. |
| 7,879,017 B1 | 2/2011 | Tabata et al. |
| 7,918,839 B2 | 4/2011 | Ehrnsperger et al. |
| 7,918,840 B2 | 4/2011 | Corneliusson |
| 7,959,619 B2 | 6/2011 | Cartier et al. |
| 8,002,760 B2 | 8/2011 | Ehrnsperger et al. |
| 8,038,662 B2 | 10/2011 | Hornung et al. |
| 8,043,274 B2 | 10/2011 | Milnar et al. |
| 8,043,275 B2 | 10/2011 | Peterson |
| 8,062,279 B2 | 11/2011 | Miyamoto |
| 8,075,543 B2 | 12/2011 | Okuda |
| 8,105,303 B2 | 1/2012 | Sakaguchi |
| 8,114,059 B2 | 2/2012 | Ehrnsperger et al. |
| 8,152,788 B2 | 4/2012 | Beckert et al. |
| 8,182,627 B2 | 5/2012 | Eckstein et al. |
| 8,211,077 B2 | 7/2012 | Sugiyama et al. |
| 8,212,102 B2 | 7/2012 | Kumasaka |
| 8,231,592 B2 | 7/2012 | Suzuki et al. |
| 8,251,967 B2 | 8/2012 | Malowaniec et al. |
| 8,328,782 B2 | 12/2012 | Catalan |
| 8,333,749 B2 | 12/2012 | Tsang et al. |
| 8,348,919 B2 | 1/2013 | Langdon et al. |
| 8,353,891 B2 | 1/2013 | Hornung et al. |
| 8,377,023 B2 | 2/2013 | Sawyer et al. |
| 8,382,735 B2 | 2/2013 | Torigoshi et al. |
| 8,475,424 B2 | 7/2013 | Fujimoto et al. |
| 8,496,638 B2 | 7/2013 | Lord et al. |
| 8,513,483 B2 | 8/2013 | Tee et al. |
| 8,518,010 B2 | 8/2013 | Kuwano et al. |
| 8,551,064 B2 | 10/2013 | LaVon et al. |
| 8,568,566 B2 | 10/2013 | Jackels et al. |
| 8,663,184 B2 | 3/2014 | Liu et al. |
| 8,668,680 B2 | 3/2014 | Ichikawa et al. |
| 8,679,084 B2 | 3/2014 | Kurihara |
| 8,716,549 B2 | 5/2014 | Cheng et al. |
| 8,764,722 B2 | 7/2014 | Rhei et al. |
| 8,777,918 B2 | 7/2014 | Kuwano et al. |
| 8,795,250 B2 | 8/2014 | O'Connell |
| 8,939,957 B2 | 1/2015 | Raycheck et al. |
| 9,044,358 B2 | 6/2015 | Nakajima et al. |
| 9,066,838 B2 | 6/2015 | Hippe et al. |
| 9,089,455 B2 | 7/2015 | Raycheck et al. |
| 9,737,444 B2 * | 8/2017 | Lawson .......... A61F 13/49017 |
| 9,750,651 B2 | 9/2017 | Bianchi et al. |
| 10,022,280 B2 | 7/2018 | Ehrnsperger et al. |
| 10,485,710 B2 | 11/2019 | Surushe |
| 10,524,962 B2 * | 1/2020 | Raycheck ......... A61F 13/49466 |
| 10,531,991 B2 * | 1/2020 | Raycheck ......... A61F 13/49466 |
| 10,583,049 B2 * | 3/2020 | Raycheck ......... A61F 13/55105 |
| 10,588,789 B2 | 3/2020 | Surushe et al. |
| 10,588,791 B2 * | 3/2020 | Raycheck ......... A61F 13/55105 |
| 2002/0128626 A1 | 9/2002 | Friderich et al. |
| 2002/0177829 A1 | 11/2002 | Fell et al. |
| 2003/0023220 A1 | 1/2003 | Ukegawa et al. |
| 2003/0050616 A1 | 3/2003 | Reynolds et al. |
| 2003/0078558 A1 | 4/2003 | Karami et al. |
| 2003/0120247 A1 | 6/2003 | Miyamoto |
| 2003/0120248 A1 | 6/2003 | Miyamoto |
| 2003/0135185 A1 | 7/2003 | Crowther |
| 2004/0002690 A1 | 1/2004 | Miyamoto |
| 2004/0127876 A1 | 7/2004 | Stevens |
| 2004/0129597 A1 | 7/2004 | Guzmann et al. |
| 2004/0158217 A1 | 8/2004 | Wu et al. |
| 2004/0222553 A1 | 11/2004 | Desai et al. |

(56) References Cited

U.S. PATENT DOCUMENTS

| | | |
|---|---|---|
| 2004/0243085 A1 | 12/2004 | Veith et al. |
| 2005/0003048 A1 | 1/2005 | Pearce et al. |
| 2005/0004549 A1 | 1/2005 | Maas et al. |
| 2005/0095700 A1 | 5/2005 | Budzowski et al. |
| 2005/0113790 A1 | 5/2005 | Suzuki |
| 2005/0177123 A1 | 8/2005 | Catalan |
| 2005/0203479 A1 | 9/2005 | Sakaguchi et al. |
| 2005/0215155 A1 | 9/2005 | Young et al. |
| 2005/0222550 A1 | 10/2005 | Mitsui et al. |
| 2005/0281757 A1 | 12/2005 | Ibrahim et al. |
| 2005/0288645 A1 | 12/2005 | LaVon |
| 2006/0014460 A1 | 1/2006 | Isele et al. |
| 2006/0058767 A1 | 3/2006 | Zhang et al. |
| 2006/0058768 A1 | 3/2006 | Zhang et al. |
| 2006/0111686 A1 | 5/2006 | Schneider |
| 2006/0264860 A1 | 11/2006 | Beck et al. |
| 2006/0270302 A1 | 11/2006 | Ando et al. |
| 2007/0005040 A1 | 1/2007 | Langdon et al. |
| 2007/0088116 A1 | 4/2007 | Abba et al. |
| 2007/0123834 A1 | 5/2007 | McDowall et al. |
| 2007/0191808 A1 | 8/2007 | Toyoshima et al. |
| 2007/0287980 A1 | 12/2007 | Kline et al. |
| 2007/0287983 A1 | 12/2007 | Lodge et al. |
| 2008/0077111 A1 | 3/2008 | Erdman et al. |
| 2008/0195070 A1 | 8/2008 | Ponomarenko et al. |
| 2008/0195071 A1 | 8/2008 | Ponomarenko et al. |
| 2008/0312617 A1 | 12/2008 | Hundorf et al. |
| 2008/0312631 A1 | 12/2008 | Okuda |
| 2009/0118689 A1 | 5/2009 | Lawson et al. |
| 2009/0157034 A1 | 6/2009 | Mattingly et al. |
| 2009/0195187 A1 | 6/2009 | Ashraf |
| 2009/0182298 A1 | 7/2009 | Kumasaka |
| 2009/0275911 A1 | 11/2009 | Hornung et al. |
| 2009/0312730 A1 | 12/2009 | LaVon et al. |
| 2009/0312734 A1 | 12/2009 | LaVon et al. |
| 2010/0028638 A1 | 2/2010 | Reichardt et al. |
| 2010/0193110 A1 | 8/2010 | Eckstein et al. |
| 2010/0305532 A1 | 12/2010 | Ashton et al. |
| 2010/0312214 A1 | 12/2010 | Shimada et al. |
| 2010/0318054 A1 | 12/2010 | Langdon et al. |
| 2011/0004177 A1 | 1/2011 | Roe et al. |
| 2011/0022019 A1 | 1/2011 | Shimada et al. |
| 2011/0066128 A1 | 3/2011 | Takahashi |
| 2011/0092944 A1 | 4/2011 | Sagasaka et al. |
| 2011/0172626 A1 | 7/2011 | Misumo et al. |
| 2011/0178489 A1 | 7/2011 | Baba et al. |
| 2011/0196327 A1 | 8/2011 | Chhabra et al. |
| 2011/0223381 A1 | 9/2011 | Sauter et al. |
| 2011/0245792 A1 | 10/2011 | O'Connell |
| 2011/0250256 A1 | 10/2011 | Hyun-Oh et al. |
| 2012/0027702 A1 | 2/2012 | Bernoud et al. |
| 2012/0073760 A1 | 3/2012 | Hamada et al. |
| 2012/0277702 A1 | 11/2012 | Raycheck et al. |
| 2012/0277713 A1 | 11/2012 | Raycheck et al. |
| 2012/0289921 A1 | 11/2012 | Hashino et al. |
| 2012/0316526 A1 | 12/2012 | Jackels et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0330262 A1 | 12/2012 | Lawson et al. |
| 2012/0330263 A1 | 12/2012 | Lawson et al. |
| 2012/0330264 A1 | 12/2012 | Lawson et al. |
| 2013/0041340 A1 | 2/2013 | Kawakami et al. |
| 2013/0255865 A1 | 10/2013 | Brown et al. |
| 2014/0005621 A1 | 1/2014 | Roe et al. |
| 2014/0142529 A1 | 5/2014 | Cheng |
| 2014/0163511 A1 | 6/2014 | Roe et al. |
| 2015/0073372 A1 | 3/2015 | Hippe et al. |
| 2016/0067940 A1 | 3/2016 | Liebe et al. |
| 2016/0270971 A1 | 9/2016 | Raycheck et al. |
| 2016/0270972 A1 | 9/2016 | Surushe et al. |
| 2016/0270973 A1 | 9/2016 | Surushe et al. |
| 2016/0270974 A1 | 9/2016 | Surushe et al. |
| 2016/0270975 A1 | 9/2016 | Surushe et al. |
| 2016/0270977 A1 | 9/2016 | Surushe et al. |
| 2016/0270978 A1 | 9/2016 | Raycheck et al. |
| 2016/0270979 A1 | 9/2016 | Raycheck et al. |
| 2016/0270980 A1 | 9/2016 | Raycheck et al. |
| 2016/0270981 A1 | 9/2016 | Raycheck et al. |
| 2016/0270982 A1 | 9/2016 | Raycheck et al. |
| 2016/0270983 A1 | 9/2016 | Roe et al. |
| 2016/0270985 A1 | 9/2016 | Raycheck et al. |
| 2016/0287449 A1 | 10/2016 | Surushe et al. |
| 2017/0266062 A1 | 9/2017 | Raycheck et al. |
| 2019/0365577 A1* | 12/2019 | Raycheck ............. A61F 13/495 |
| 2020/0054499 A1 | 2/2020 | Surushe et al. |
| 2020/0085643 A1 | 3/2020 | Raycheck et al. |
| 2020/0085646 A1 | 3/2020 | Raycheck et al. |
| 2020/0155366 A1 | 5/2020 | Raycheck et al. |
| 2020/0170852 A1 | 6/2020 | Surushe et al. |
| 2020/0188192 A1 | 6/2020 | Raycheck et al. |
| 2020/0397624 A1 | 12/2020 | Prakash et al. |

FOREIGN PATENT DOCUMENTS

| | | |
|---|---|---|
| CN | 1589129 A | 3/2005 |
| CN | 101010053 A | 8/2007 |
| CN | 101027027 A | 8/2007 |
| CN | 101277664 A | 10/2008 |
| CN | 102413799 A | 4/2012 |
| CN | 102753129 A | 10/2012 |
| CN | 102821724 A | 12/2012 |
| CN | 202682191 U | 1/2013 |
| CN | 103705344 A | 4/2014 |
| CN | 103732194 A | 4/2014 |
| CN | 203576760 U | 5/2014 |
| CN | 104185462 A | 12/2014 |
| CN | 104185465 A | 12/2014 |
| CN | 104958139 A | 10/2015 |
| EA | 200901264 A1 | 4/2010 |
| EP | 0 214 636 B1 | 11/1991 |
| EP | 0486006 A2 | 5/1992 |
| EP | 0 404 648 B1 | 2/1994 |
| EP | 0 412 579 B1 | 6/1994 |
| EP | 0 403 832 B1 | 10/1994 |
| EP | 0 773 769 B1 | 11/2000 |
| EP | 0 866 682 B1 | 3/2002 |
| EP | 0 376 022 B2 | 3/2006 |
| EP | 1 905 402 A2 | 6/2008 |
| GB | 2383522 A | 7/2003 |
| JP | 6426701 A | 1/1989 |
| JP | H 0265861 A | 3/1990 |
| JP | 5192367 B2 | 8/1993 |
| JP | 7184955 A | 7/1995 |
| JP | 07-313550 A | 12/1995 |
| JP | H 08-215239 A | 8/1996 |
| JP | 8252280 A | 10/1996 |
| JP | 9215709 A | 8/1997 |
| JP | 2810738 B2 | 10/1998 |
| JP | H 10-277091 A | 10/1998 |
| JP | 11253483 A | 9/1999 |
| JP | 11318978 A | 11/1999 |
| JP | 11323611 A | 11/1999 |
| JP | 2602070 Y2 | 12/1999 |
| JP | 2000-014702 A | 1/2000 |
| JP | 2603259 Y2 | 3/2000 |
| JP | 2000-254176 A | 9/2000 |
| JP | 2000-288016 A | 10/2000 |
| JP | 2000288012 A | 10/2000 |
| JP | 2000-342623 A | 12/2000 |
| JP | 2001-245922 A | 9/2001 |
| JP | 3242586 B2 | 12/2001 |
| JP | 2002-102279 A | 4/2002 |
| JP | 2002-209938 A | 7/2002 |
| JP | 3315993 B2 | 8/2002 |
| JP | 2002-253604 A | 9/2002 |
| JP | 3391776 B2 | 3/2003 |
| JP | 3391779 B2 | 3/2003 |
| JP | 3406231 B2 | 5/2003 |
| JP | 3488506 B2 | 1/2004 |
| JP | 3605426 B2 | 1/2004 |
| JP | 3493211 B2 | 2/2004 |
| JP | 2014-083191 A | 5/2004 |
| JP | 3592591 B2 | 11/2004 |

(56) References Cited

FOREIGN PATENT DOCUMENTS

| | | |
|---|---|---|
| JP | 3606297 | 1/2005 |
| JP | 3615894 B2 | 8/2005 |
| JP | 3771466 B2 | 4/2006 |
| JP | 3773550 B2 | 5/2006 |
| JP | 3825977 B2 | 9/2006 |
| JP | 2006-263306 A | 10/2006 |
| JP | 2006-320709 A | 11/2006 |
| JP | 3856904 B2 | 12/2006 |
| JP | 3884292 B2 | 2/2007 |
| JP | 2007-143633 A | 6/2007 |
| JP | 3926585 B2 | 6/2007 |
| JP | 3953228 B2 | 8/2007 |
| JP | 2008-302138 A | 12/2008 |
| JP | 4215370 B2 | 1/2009 |
| JP | 2009-056142 | 3/2009 |
| JP | 4330281 B2 | 9/2009 |
| JP | 2011177288 A | 9/2011 |
| JP | 4996508 B2 | 8/2012 |
| JP | 5001756 B2 | 8/2012 |
| JP | 2014-012219 A | 1/2014 |
| JP | 2014-068848 A | 4/2014 |
| JP | 5651801 B1 | 1/2015 |
| WO | WO 1994-04656 A2 | 3/1994 |
| WO | WO 1993-03698 A1 | 6/1994 |
| WO | WO 1995-16746 A1 | 6/1995 |
| WO | WO 1996-039553 A1 | 2/1996 |
| WO | WO 1997-20532 A1 | 6/1997 |
| WO | WO 2002-36059 A1 | 5/2002 |
| WO | WO 2006-135357 A1 | 12/2006 |
| WO | 2012067216 A1 | 5/2012 |
| WO | WO 2013-065618 A1 | 5/2013 |
| WO | WO 2013-065619 A1 | 5/2013 |
| WO | 2014020382 A1 | 2/2014 |
| WO | 2014125858 A1 | 8/2014 |
| WO | WO 2014-147879 A1 | 9/2014 |
| WO | WO 2015-005166 A1 | 1/2015 |
| WO | WO 2015-198928 A1 | 12/2015 |
| WO | WO 2016-051936 A1 | 4/2016 |
| WO | WO 2016-051937 A1 | 4/2016 |
| WO | WO 2016-051938 A1 | 4/2016 |

OTHER PUBLICATIONS

All Office Actions, U.S. Appl. No. 16/543,984.
All Office Actions, U.S. Appl. No. 16/690,841.
All Office Actions, U.S. Appl. No. 16/693,766.
All Office Actions, U.S. Appl. No. 16/752,769.
All Office Actions, U.S. Appl. No. 16/782,187.
All Office Actions, U.S. Appl. No. 16/795,778.
All Office Actions, U.S. Appl. No. 17/009,836.
PCT International Search Report and Written Opinion for PCT/US2019/023 097, dated Jun. 30, 2016 (14 pages).
P&G, All Office Actions for U.S. Appl. No. 15/074,047.
P&G, All Office Actions for U.S. Appl. No. 15/074,066.
P&G, All Office Actions for U.S. Appl. No. 15/074,108.
P&G, All Office Actions for U.S. Appl. No. 15/074,145.
P&G, All Office Actions for U.S. Appl. No. 15/074,211.
P&G, All Office Actions for U.S. Appl. No. 15/074,240.
P&G, All Office Actions for U.S. Appl. No. 15/074,300.
P&G, All Office Actions for U.S. Appl. No. 15/074,352.
P&G, All Office Actions for U.S. Appl. No. 15/074,382.
P&G, All Office Actions for U.S. Appl. No. 15/074,453.
P&G, All Office Actions for U.S. Appl. No. 15/074,496.
P&G, All Office Actions for U.S. Appl. No. 15/074,543.
P&G, All Office Actions for U.S. Appl. No. 15/074,650.
P&G, All Office Actions for U.S. Appl. No. 15/074,675.
P&G, All Office Actions for U.S. Appl. No. 15/074,583.
All Office Actions, U.S. Appl. No. 17/712,545, filed Apr. 4, 2022.
U.S. Unpublished U.S. Appl. No. 17/712,545, filed Apr. 4, 2022, to Jeromy Thomas Raycheck et. al.

* cited by examiner

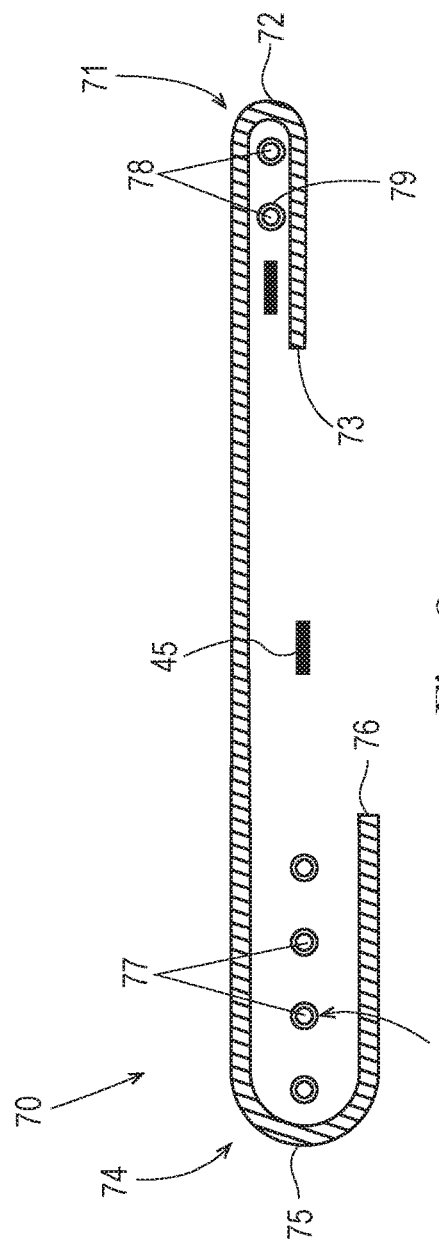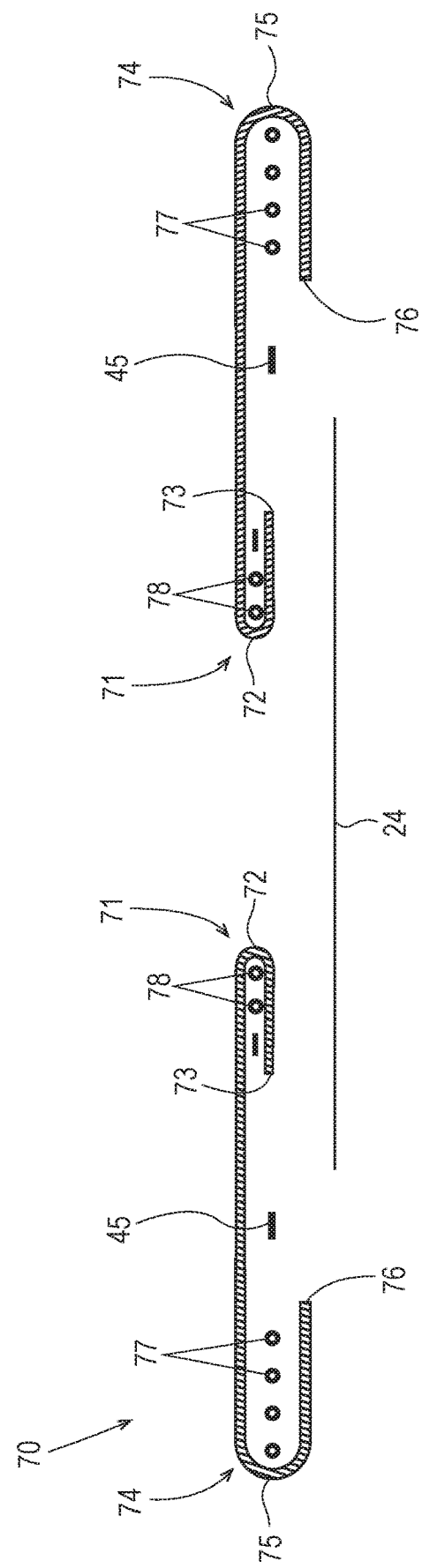

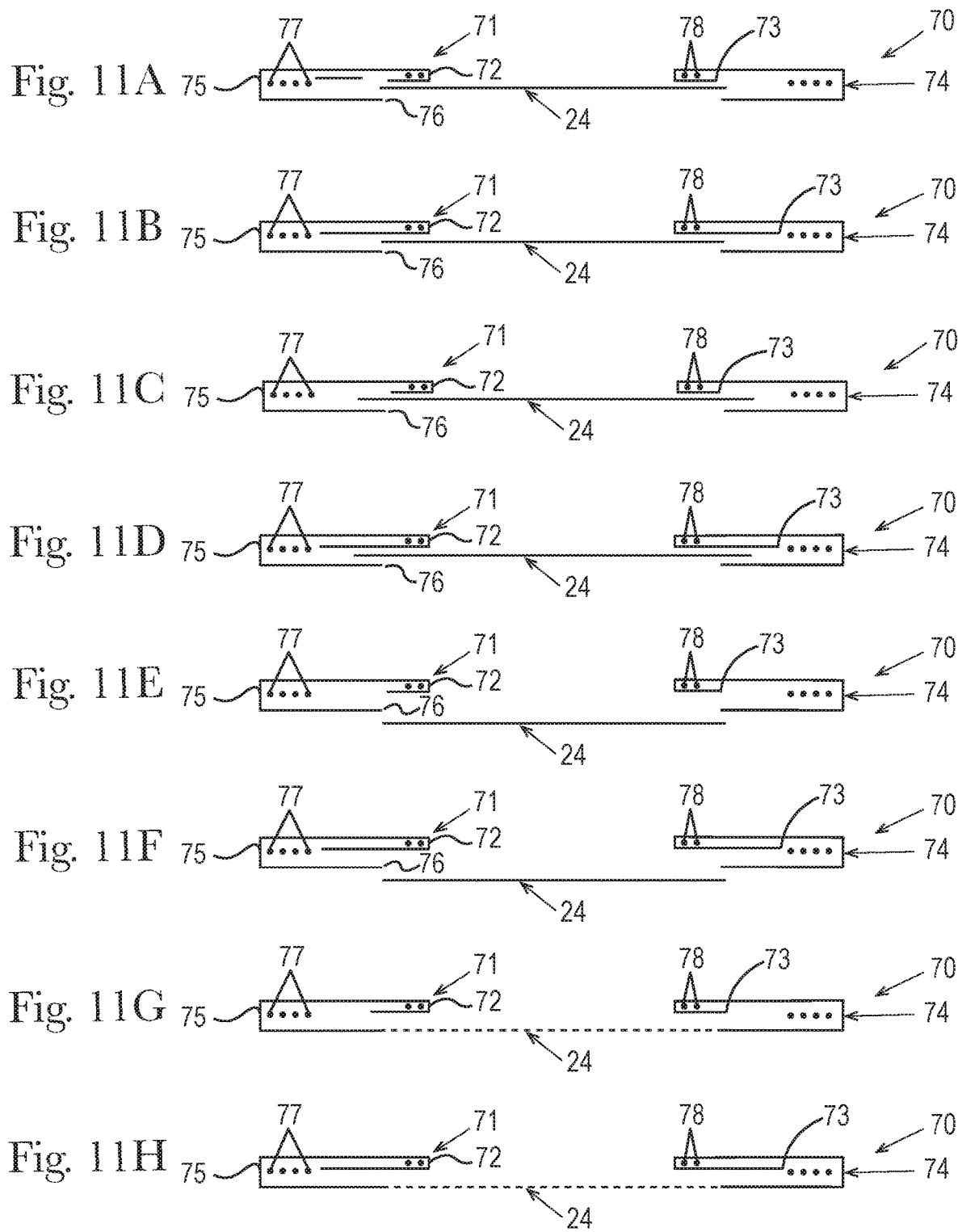

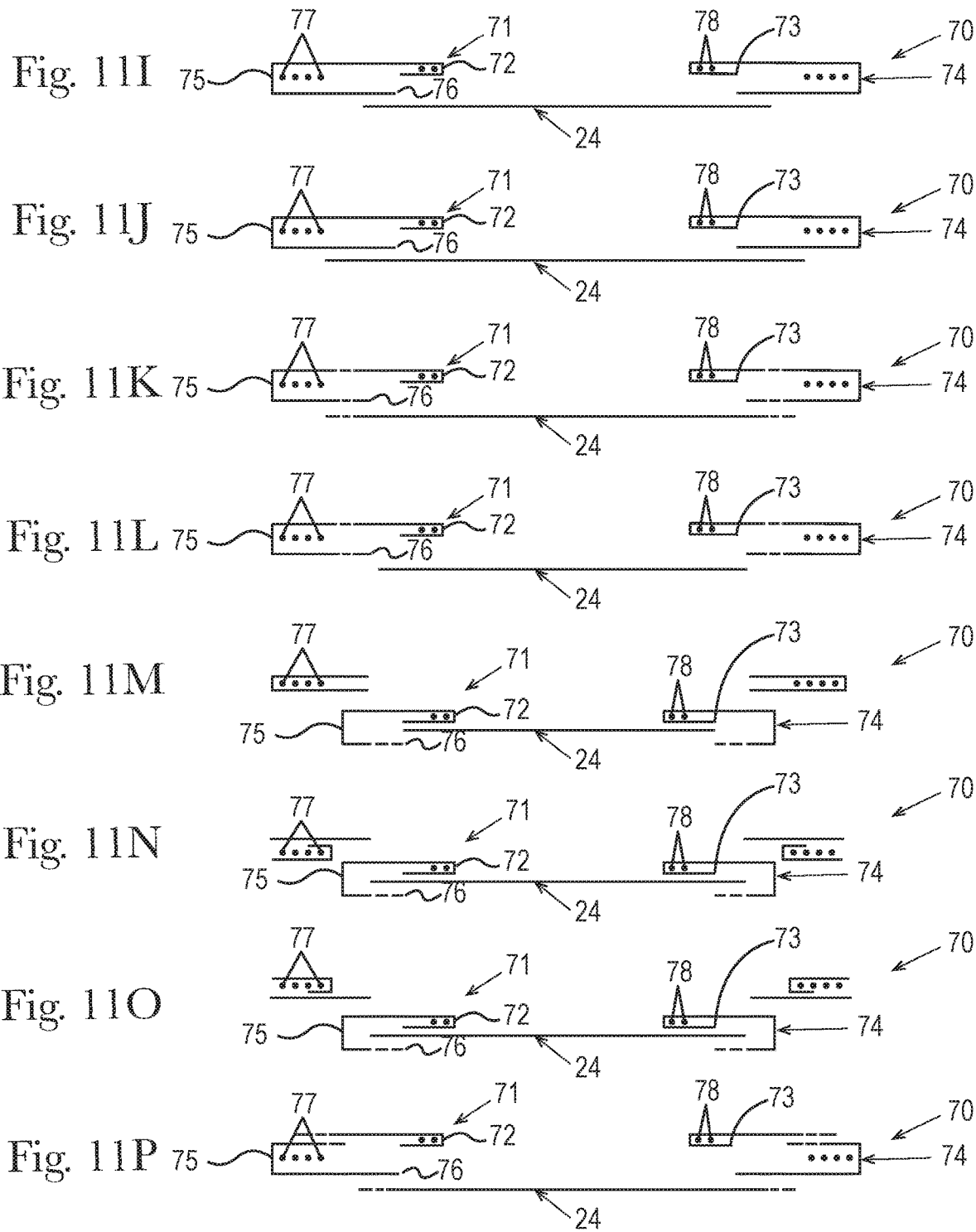

ABSORBENT ARTICLE WITH LEG CUFFS

CROSS REFERENCE TO RELATED APPLICATIONS

This application is a continuation of, and claims priority under 35 U.S.C. § 120 to, U.S. patent application Ser. No. 15/074,583, filed on Mar. 18, 2016, which claims the benefit, under 35 USC § 119(e), of U.S. Provisional Patent Application Ser. No. 62/134,628, filed Mar. 18, 2015, the entirety of both of which are incorporated by reference herein.

FIELD OF INVENTION

This invention relates to absorbent articles (e.g., diapers, adult incontinence articles, feminine hygiene pads) having improved leg cuffs that yield a more garment-like article, as well as having improved functional characteristics (e.g., reduced leakage, reduced sagging, fecal material containment).

BACKGROUND OF THE INVENTION

It has long been known that absorbent articles such as conventional absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). To effectively contain bodily exudates, the article should provide a snug fit around the waist and legs of a wearer.

Current diaper designs frequently include the use of a barrier leg cuff to prevent leakage of bodily exudates and an outer cuff which provides a covering over the barrier leg cuff to minimize the visibility of exudates through the barrier cuff and provide a secondary means to capture bodily exudates should they breach the barrier leg cuff. The barrier leg cuff may be made using a hydrophobic nonwoven and may be disposed on the body-facing surface of the absorbent article or connected to the body-facing surface of the film backsheet layer. The barrier leg cuff may be a substantially liquid impervious layer that prevents bodily exudates from passing out of the sides of the article and may also be highly breathable, allowing outside air to reach the skin to help maintain a healthy level of skin hydration. In many current diapers, the outer cuff comprises the polymeric film layer of the backsheet to provide the high opacity required to cover the barrier leg cuff as well as to prevent molten adhesive from passing through the cuff to the garment-facing surface of the article during manufacturing. The outer cuff contains the outer leg elastic strands, which create the contraction forces and gathers, and can be sandwiched between the cuff material and backsheet material. The elastic strands in the leg cuffs are typically joined with molten adhesive during manufacture, and the hot adhesive has the potential to pass through nonwoven materials during manufacture, causing contamination of manufacturing lines as well as the potential for stickiness on the outside surface of the article. The polymeric film is generally used to prevent these issues, however, results in a plastic-like look as well as a noisy application process.

Because of manufacturing tolerances when cutting, tracking, and combining materials, the outer leg elastic strands are generally spaced inboard from the longitudinal edge of the article in the crotch region. This prevents inadvertent cutting or exposure of the outer leg elastic strands during the manufacturing process. This design results in the outermost portion of the longitudinal edge of the product not continuously contacting closely to the skin of the user during wear. Thus, the ability of the elastic strand(s) to control the edge of the article diminishes as the distance between the outermost elastic and the edge increases, leading to a more random distribution of larger gathers which contact the skin at larger intervals or sometimes not at all. This effect can lead to user perception that the diaper may leak where the longitudinal edge does not contact the skin of the user. In addition, many articles currently available contain only two to three outer leg elastics per side to create the gathers, increasing the difficulty of achieving the desired appearance of a wide finished leg cuff or more garment-like cuff such as the elasticized hemmed edge of the arm cuff of a sweater. If the elastics are spaced more closely, the result is a narrow section of elasticized zone, which results in a less finished, less comfortable, and less clothing-like appearance. If the elastics are spaced farther apart, the gathers can appear to separate further from the skin of the user, leading to a perception of potential leakage risk. As discussed above, this is driven by having less control of the gathers between strands of increasing separation.

Accordingly, it is desirable to provide an absorbent article with a folded outer cuff design having finished edges with elastics that are close to the edge to maintain a close proximity to the skin to create improved fit, a more aesthetically pleasing, clothing-like design and improved leakage protection.

Further, achieving such aesthetically pleasing, clothing-like absorbent article designs (e.g., by including folded outer cuff designs having finished edges) will generally result in articles that have a wider outermost-to-outermost elastic spacing. Because the outermost-to-outermost elastic cross dimensional length determines the effective width of the chassis, one drawback of these designs is that the effective crotch width is greater when compared to traditional absorbent articles. Articles with wider effective crotch widths tend to fit lower in the crotch, and the extra material creates a "c" shape cupping around the crotch area. Accordingly, the "c" shape cupping around the crotch area is larger for absorbent articles with folded outer cuff designs having finished edges versus traditional outer cuff designs. Moms often view the larger "c" shape cupping negatively as sagging and/or poor fitting in the crotch area.

Accordingly, it is of continued interest to provide an economically viable disposable absorbent article with the ability to minimize the negative effects of bodily extrudate leaks, while also reducing the appearance of sagging. To that end, it is of continued interest to provide a disposable absorbent article having sufficient retention capability to safely and cleanly retain bodily extrudate away from the wearer's clothing and/or skin throughout the expected time of article use, while also maintaining the desired appearance of a proper fit on the body.

SUMMARY OF THE INVENTION

In one aspect, a disposable absorbent article for wearing about the lower torso of a wearer includes a first waist region, a second waist region, a crotch region disposed between the first and second waist regions, a first waist edge and a second waist edge, and a first longitudinal edge and a second longitudinal edge, the disposable absorbent article including a chassis that includes a topsheet, a backsheet, and an absorbent core disposed between the topsheet and the backsheet; the disposable absorbent article further including a leg gasketing system, wherein the leg gasketing system comprises a web of material forming an inner cuff and an outer cuff; wherein the inner cuff comprises an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge; wherein at least a portion of the web of material between the outer cuff folded edge and the outer cuff material edge is attached to the chassis in the first waist region, the second waist region and the crotch region; and at least a portion of the web of material between the inner cuff folded edge and the outer cuff folded edge is attached to the chassis in the crotch region and the first waist region; and the web of material between the inner cuff folded edge and the outer cuff folded edge is unattached to the chassis in at least a portion of the second waist region, forming a leg gasketing system pocket with an opening on an inboard longitudinal edge of the leg gasketing system pocket; and wherein the absorbent core comprises superabsorbent polymer enclosed within a core wrap, wherein the superabsorbent polymer is disposed on an absorbent material deposition area within the core wrap and the absorbent material deposition area comprises at least one channel which is at least partially oriented in the longitudinal direction of the disposable absorbent article.

In another aspect, a disposable absorbent article for wearing about the lower torso of a wearer includes a first waist region, a second waist region, a crotch region disposed between the first and second waist regions, a first waist edge and a second waist edge, and a first longitudinal edge and a second longitudinal edge, the disposable absorbent article including a chassis that includes a topsheet, a backsheet, an absorbent core disposed between the topsheet and the backsheet, and a liquid management system adjacent to the absorbent core; wherein the disposable absorbent article further comprises a leg gasketing system; wherein the leg gasketing system comprises a web of material forming an inner cuff and an outer cuff; wherein the inner cuff comprises an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge; wherein at least a portion of the web of material between the outer cuff folded edge and the outer cuff material edge is attached to the chassis in the first waist region, the second waist region and the crotch region; and at least a portion of the web of material between the inner cuff folded edge and the outer cuff folded edge is attached to the chassis in the crotch region and the first waist region; and the web of material between the inner cuff folded edge and the outer cuff folded edge is unattached to the chassis in at least a portion of the second waist region, forming a leg gasketing system pocket with an opening on an inboard longitudinal edge of the leg gasketing system pocket; wherein the absorbent core comprises superabsorbent polymer enclosed within a core wrap, wherein the superabsorbent polymer is disposed on an absorbent material deposition area within the core wrap and the absorbent material deposition area comprises at least one channel which is at least partially oriented in the longitudinal direction of the disposable absorbent article; and wherein the liquid management system comprises at least one liquid management system channel, and wherein the at least one channel of the absorbent core aligns with the at least one liquid management system channel.

In another aspect, a disposable absorbent articles include a first waist region, a second waist region, a crotch region disposed between the first and second waist regions, a first waist edge and a second waist edge, and a first longitudinal edge and a second longitudinal edge, the disposable absorbent articles further including a chassis that includes a topsheet, a backsheet, and an absorbent core disposed between the topsheet and the backsheet; wherein the disposable absorbent article further comprises a leg gasketing system; wherein the leg gasketing system comprises a web of material forming an inner cuff and an outer cuff; wherein the inner cuff comprises an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge; wherein the leg gasketing system extends from the first waist edge to the second waist edge; and at least a portion of the web of material between the outer cuff folded edge and the outer cuff material edge is attached to the chassis in the first waist region, the second waist region and the crotch region; and at least a portion of the web of material between the inner cuff folded edge and the outer cuff folded edge is attached to the chassis in the crotch region and the first waist region; wherein the outer cuff comprises an elastics adhesive and at least one longitudinally oriented elastic member running parallel to the outer cuff folded edge, the elastics adhesive and at least one elastic member disposed between 1) the web of material between the outer cuff folded edge and the outer cuff material edge and 2) the web of material between the outer cuff folded edge and the inner cuff folded edge; wherein in at least a portion of the second waist region, the outer cuff is free of elastics adhesive and elastic members, thus forming a leg gasketing system pocket between 1) the web of material between the outer cuff folded edge and the outer cuff material edge and 2) the web of material between the outer cuff folded edge and the inner cuff folded edge, the leg gasketing system pocket having an outboard longitudinal edge at the outer cuff folded edge; wherein the leg gasketing system pocket comprises an opening on an inboard longitudinal edge of the leg gasketing system pocket; and wherein the absorbent core comprises superabsorbent polymer enclosed within a core wrap, wherein the superabsorbent polymer is disposed on an absorbent material deposition area within the core wrap and the absorbent material deposition area comprises at least one channel which is at least partially oriented in the longitudinal direction of the disposable absorbent article.

The disposable absorbent articles described herein comprise leg gasketing systems that may comprise one web or multiple webs of material. The description and claims herein may refer to leg gasketing systems that are formed from "a web of material." The recitation of "a web of material" encompasses a single continuous web of material, multiple webs of material that are joined together to become one web of material, or multiple distinct webs of material that are separate from the disposable absorbent article chassis, and form part of the leg gasketing system. The leg gasketing systems described herein may comprise N-fiber material or other non-woven materials.

BRIEF DESCRIPTION OF THE DRAWINGS

FIG. 2 is a schematic cross sectional view of the leg gasketing system of FIG. 1, taken along the lateral centerline. The leg gasketing system is shown in a flat, uncontracted state.

FIG. 3 is a schematic cross sectional view of the leg gasketing systems and topsheet of FIG. 1, the cross section taken along the lateral centerline. The leg gasketing systems are shown in a flat, uncontracted state.

DETAILED DESCRIPTION OF THE INVENTION

Definitions

Figure 1:
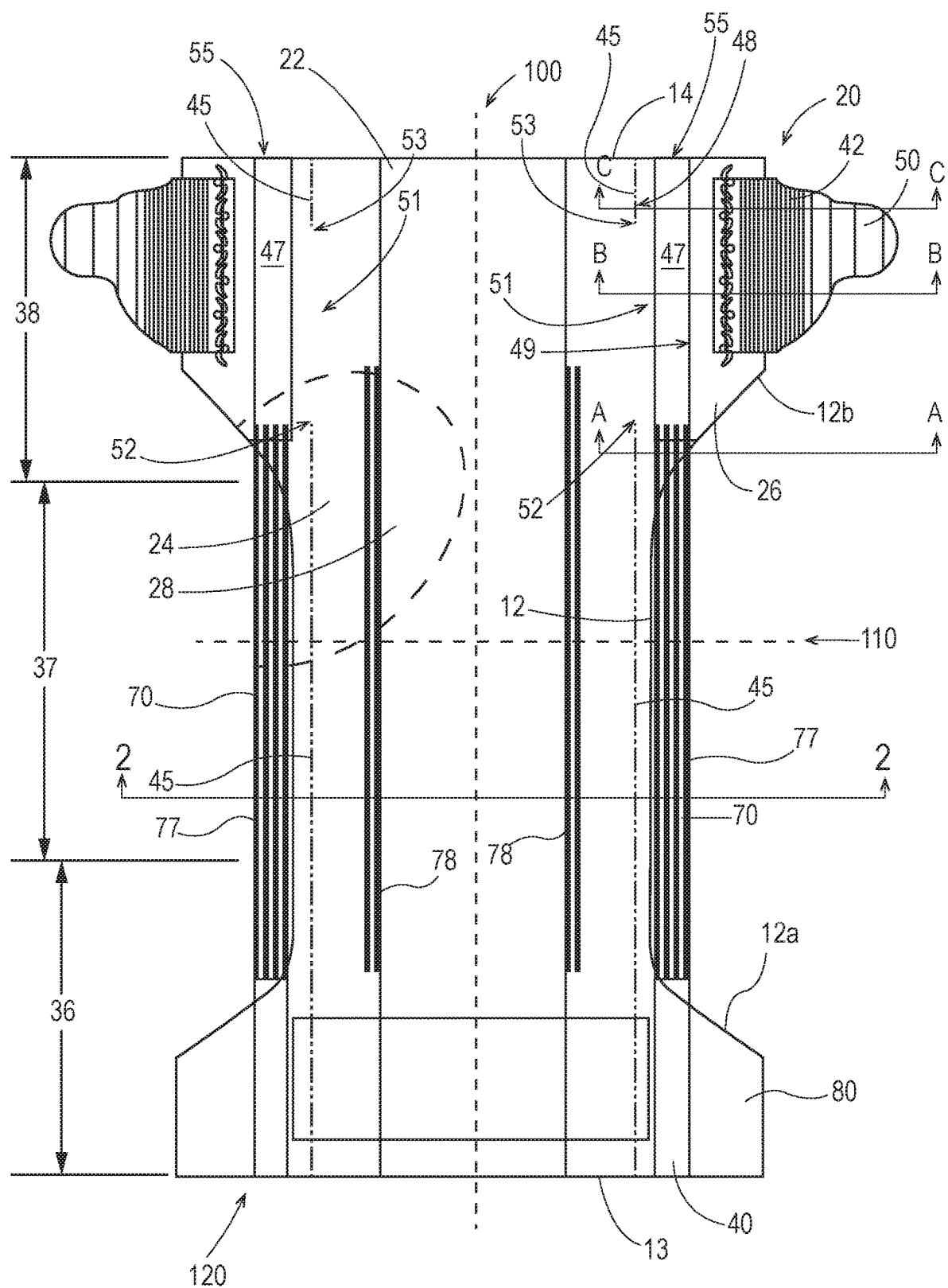
FIG. 1 is a schematic plan view of an absorbent article as detailed herein.

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable."

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Elastomeric material" is a material exhibiting elastic properties. Elastomeric materials may include elastomeric films, scrims, nonwovens, and other sheet-like structures.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Channel" refers to a region or zone in a material layer that has a substantially lower basis weight (e.g., less than 50%, less than 70%, less than 90%) than the surrounding material in the material layer. The channel may be a region in a material layer that is substantially material-free (e.g., 90% material-free, 95% material-free, or 99% material-free, or completely material-free). A channel may extend through one or more material layers. The channels generally have a lower bending modulus than the surrounding regions of the material layer, enabling the material layer to bend more easily and/or contain more bodily exudates within the channels than in the surrounding areas of the material layer. Thus, a channel is not merely an indentation in the material layer that does not create a reduced basis weight in the material layer in the area of the channel.

Absorbent Article:

The present disclosure is directed to a disposable absorbent article with a leg gasketing system that comprises a folded outer cuff having neatly finished outer cuff folded edges that creates an aesthetically pleasing design that is garment like. The absorbent article also may include a leg gasketing system pocket with an opening towards the interior of the article, wherein the pocket reduces runny bowel movement leaks. The folded outer cuff design is advantageous in preventing penetration and adhesive bleedthrough without the use of a polymeric film layer in the elasticized region. The absorbent article may comprise an opacity strengthening patch to provide the strength needed to prevent the article from extending excessively during application and wearing, and provide the opacity at the sides and waist to prevent the skin of the user from showing through the article. The absorbent article may comprise one or more waistbands on the lateral edges of the absorbent article. The absorbent article may comprise a channeled absorbent core that provides rigidity to the absorbent article when loaded with urine and/or runny bowel movement.

An absorbent article design with the synergistic combination of both neatly finished outer leg cuff folded edges and a channeled absorbent core may combat some and/or all of the issues detailed in the background (e.g., saggy and/or poor fitting appearance). Accordingly, absorbent articles with both neatly finished outer leg cuff folded edges and a channeled absorbent core may provide a more garment like diaper appearance that maintains a good fitting appearance even after loaded with bodily fluids from the wearer.

FIG. 1 is a plan view of an absorbent article 20 as described herein in a flat, uncontracted state. The garment-facing surface 120 of the absorbent article 20 is facing the viewer. The absorbent article 20 includes a longitudinal centerline 100 and a lateral centerline 110. The absorbent article 20 may comprise a chassis 22. The absorbent article 20 and chassis 22 are shown to have a first waist region 36, a second waist region 38 opposed to the first waist region 36, and a crotch region 37 located between the first waist region 36 and the second waist region 38. The waist regions 36 and 38 generally comprise those portions of the absorbent article 20 which, when worn, encircle the waist of the wearer. The waist regions 36 and 38 may include elastic elements (e.g., a waistband) such that they gather about the waist of the wearer to provide improved fit and containment. The crotch region 37 is the portion of the absorbent article 20 which, when the absorbent article 20 is worn, is generally positioned between the legs of the wearer.

The outer periphery of chassis 22 is defined by longitudinal edges 12 and waist edges (first waist edge 13 in first waist region 36 and second waist edge 14 in second waist region 38). The longitudinal edges 12 may be subdivided into a front longitudinal edge 12a, which is the portion of the longitudinal edge 12 in the first waist region 36, and a rear longitudinal edge 12b, which is the portion of the longitudinal edge 12 in the rear waist region 38. The chassis 22 may have opposing longitudinal edges 12 that are oriented generally parallel to the longitudinal centerline 100. However, for better fit, longitudinal edges 12, 12a and 12b of the chassis 22 may be curved or angled to produce, for example, an "hourglass" shape diaper when viewed in a plan view. As seen in FIGS. 1, 4-9 and 12-14, when viewed in plan view, absorbent articles may have the hourglass shaped chassis that is wider in the front and back waist regions 36, 38 and narrower in the crotch region 37. The leg gasketing systems 70 overhang the edge of the chassis 22 in the crotch region 37 and in portions of the front and back waist regions 36, 38. Accordingly, as seen in FIGS. 1, 4-9 and 12-14, in the crotch region 37 and in portions of the front and back waist regions 36, 38 nearer the crotch region 37, the outboard edge of the leg gasketing systems 70 (i.e., the outer cuff folded edge 75) is outboard of the outboard edge of the chassis 22; and in the portions of the front and back waist regions 36, 38 away from the crotch region 37 (i.e., nearer the lateral edges 13, 14), the outboard edge of the leg gasketing systems 70 (i.e., the outer cuff folded edge 75) is inboard of the outboard edge of the chassis 22. And between the regions where the outboard edge of the leg gasketing systems 70 (i.e., the outer cuff folded edge 75) is outboard of the outboard edge of the chassis 22, and the region where the outboard edge of the leg gasketing systems 70 (i.e., the outer cuff folded edge 75) is inboard of the outboard edge of the chassis 22, there are two points (one in the front waist region 36 and one in the rear waist region 38) where the outboard edge of the leg gasketing systems 70 (i.e., the outer cuff folded edge 75) is coterminous with the outboard edge of the chassis 22. The chassis 22 may also have opposing lateral edges 13, 14 that are oriented generally parallel to the lateral centerline 110.

The chassis 22 may comprise a liquid permeable topsheet 24, a backsheet 26, and an absorbent core 28 between the topsheet 24 and the backsheet 26. For absorbent articles that include one or more opacity strengthening patches 80, the chassis 22 also comprises the opacity strengthening patch(s). The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. The absorbent article may also comprise a liquid management system ("LMS") 150 (shown in FIGS. 19 and 21) which in the example represented comprises a distribution layer 154 and an acquisition layer 152, which will be further detailed below. The acquisition layer 152 may instead distribute bodily exudates and the distribution layer 154 may instead acquire bodily exudates or both layers may distribute and/or acquire bodily exudates. The LMS 150 may also be provided as a single layer or two or more layers.

The absorbent core 28 may comprise 75% to 100%, at least 80%, at least 85%, at least 90%, at least 95%, or at least 99%, all by weight, of absorbent material (specifically reciting all 0.1% increments within the above-specified ranges and all ranges formed therein or thereby) and a core wrap enclosing the absorbent material. The core wrap may typically comprise two materials, substrates, or nonwoven materials 116 and 116' for the top side and bottom side of the core. The core may comprise one or more channels. Additionally or alternatively, the LMS 150 may comprise one or more channels. The channels of the LMS 150 may be positioned within the absorbent article 20 such they aligned with, substantially aligned with, overlap, or at least partially overlap, the channels of the absorbent core 28. These and other components of the absorbent articles will now be discussed in more details.

Topsheet:

The topsheet 24 is generally a portion of the absorbent article 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, Tenn. as supplier code 055SLPV09U. The topsheet 24 may be apertured.

Any portion of the topsheet 24 may be coated with a lotion or skin care composition as is known in the art. Non-limiting examples of suitable lotions include those described in U.S. Pat. Nos. 5,607,760; 5,609,587; 5,635, 191; and 5,643,588. The specific examples are not limiting, as any lotion or skin care composition known in the art may be utilized. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

Backsheet:

The backsheet 26 is generally positioned such that it may be at least a portion of the garment-facing surface 120 of the absorbent article 20. Backsheet 26 may be designed to prevent the exudates absorbed by and contained within the absorbent article 20 from soiling articles that may contact the absorbent article 20, such as bed sheets and undergarments. The backsheet 26 may be substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially liquid-impermeable film. The outer cover and an inner layer may be joined together by adhesive or any other suitable material or method. A particularly suitable outer cover is available from Corovin GmbH, Peine, Germany as supplier code A18AHO, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

Ears/Fasteners:

The absorbent article 20 may include front ears 40 and/or back ears 42. The ears 40, 42 may be extensible, inextensible, elastic, or inelastic. The ears 40, 42 may be formed from nonwoven webs, woven webs, knitted fabrics, polymeric and elastomeric films, apertured films, sponges, foams, scrims, and combinations and laminates thereof. The ears 40, 42 may be formed of a stretch laminate such as a nonwoven/elastomeric material laminate or a nonwoven/elastomeric material/nonwoven laminate. Stretch laminates may be formed by any method known in the art. For example, the ears 40, 42 may be formed as a zero strain stretch laminate, which includes at least a layer of non-woven material and an elastomeric element. The elastomeric element is attached to the layer of non-woven material while in a relaxed or substantially relaxed state, and the resulting laminate is made stretchable (or more stretchable over a further range) by subjecting the laminate to an activation process which elongates the nonwoven layer permanently, but the elastomeric element temporarily. The nonwoven layer may be integral with at least a portion of the chassis 22, in which case the elastomeric element may be attached to the nonwoven layer and the non-woven/elastomeric element laminate is subsequently activated. Alternatively, the non-woven layer may be a separate component, in which case the elastomeric element is attached to the nonwoven layer to form the laminate, which is then coupled to the main portion. If one or more layers of the side panel are provided separately, the laminate may be activated either before or after attachment to the main portion. The zero strain activation processes is further disclosed in U.S. Pat. Nos. 5,167,897 and 5,156,793. A suitable elastic ear may be an activated laminate comprising an elastomeric film (such as is available from Tredegar Corp, Richmond, Va., as supplier code X25007) disposed between two nonwoven layers (such as is available from BBA Fiberweb, Brentwood, Tenn. as supplier code FPN332).

The ears 40, 42 may be discrete or integral. A discrete ear is formed as separate element which is joined to the chassis 22. An integral ear is a portion of the chassis 22 that projects laterally outward from the longitudinal edge 12. The integral ear may be formed by cutting the chassis form to include the shape of the ear projection.

The absorbent article 20 may also include a fastening system 50. When fastened, the fastening system 50 interconnects the first waist region 36 and the rear waist region 38 resulting in a waist circumference that may encircle the wearer during wear of the absorbent article 20. The fastening system 50 may comprises a fastener such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; and 5,591,152.

Absorbent Core:

As used herein, the term "absorbent core" refers to the individual component of the absorbent article having the most absorbent capacity and may comprise an absorbent material. The absorbent core may comprise a core wrap enclosing the absorbent material. The term "absorbent core" does not include the liquid management system or any other component of the absorbent article which is not either integral part of the core wrap or placed within the core wrap. The absorbent core may comprise, consist essentially of, or consist of, a core wrap, absorbent material as defined below, and glue enclosed within the core wrap. The absorbent core periphery, which may be the periphery of the core wrap, may define any suitable shape, such as a "T," "Y," "hour-glass," or "dog-bone" shape, for example. An absorbent core periphery having a generally "dog bone" or "hour-glass" shape may taper along its width towards the middle or "crotch" region of the core. In this way, the absorbent core may have a relatively narrow width in an area of the absorbent core intended to be placed in the crotch region of an absorbent article.

The absorbent core 28 of the present disclosure may comprise an absorbent material with a high amount of superabsorbent polymers (herein abbreviated as "SAP") enclosed within a core wrap. The SAP content may represent 70% to 100% or at least 70%, 75%, 80%, 85%, 90%, 95%, 99%, or 100% by weight of the absorbent material contained in the core wrap. The core wrap is not considered as absorbent material for the purpose of assessing the percentage of SAP in the absorbent core.

"Absorbent material" means a material which has some absorbency property or liquid retaining properties, such as SAP, cellulosic fibers as well as synthetic fibers. Typically, glues used in making absorbent cores have no absorbency properties and are not considered as absorbent material. The SAP content may be higher than 80%, for example at least 85%, at least 90%, at least 95%, at least 99%, and even up to and including 100% of the weight of the absorbent material contained within the core wrap, as stated above. This provides a relatively thin core compared to conventional cores typically comprising between 40-60% SAP, for example, and high content of cellulose fibers. The absorbent material may comprise less than 15% or less than 10% weight percent of natural or synthetic fibers, less than 5% weight percent, less than 3% weight percent, less than 2% weight percent, less than 1% weight percent, or may even be substantially free of, or free of, natural and/or synthetic fibers, specifically reciting all 0.1% increments within the specified ranges and all ranges formed therein or thereby. The absorbent material may advantageously comprise little or no airfelt (cellulose) fibers, in particular the absorbent core may comprise less than 15%, 10%, 5%, 3%, 2%, 1% airfelt (cellulose) fibers by weight, or may even be substantially free of, or free of, cellulose fibers, specifically reciting all 0.1% increments within the specified ranges and all ranges formed therein or thereby.

Figure 14:
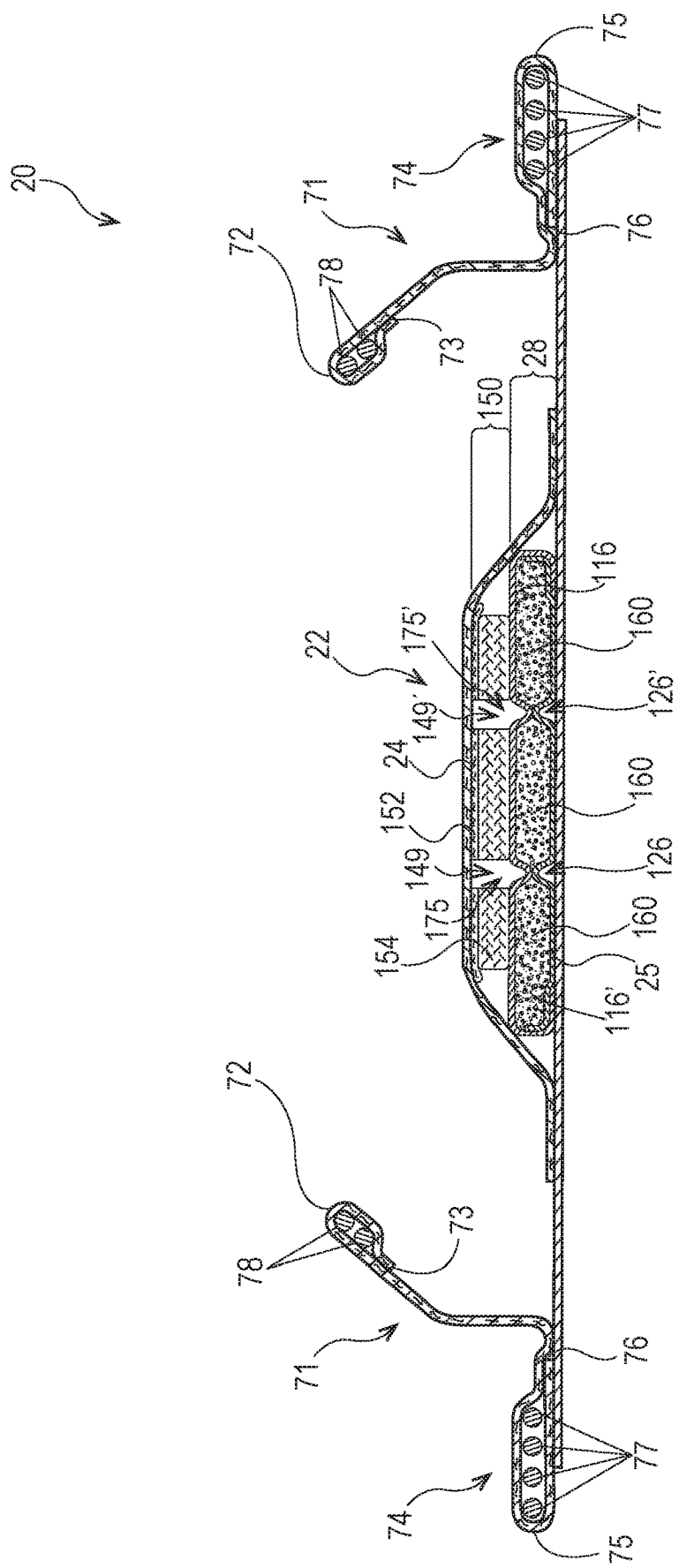
FIG. 14 is a cross-sectional view taken about line 2-2 of the absorbent article of FIG. 1.
Figure 15:
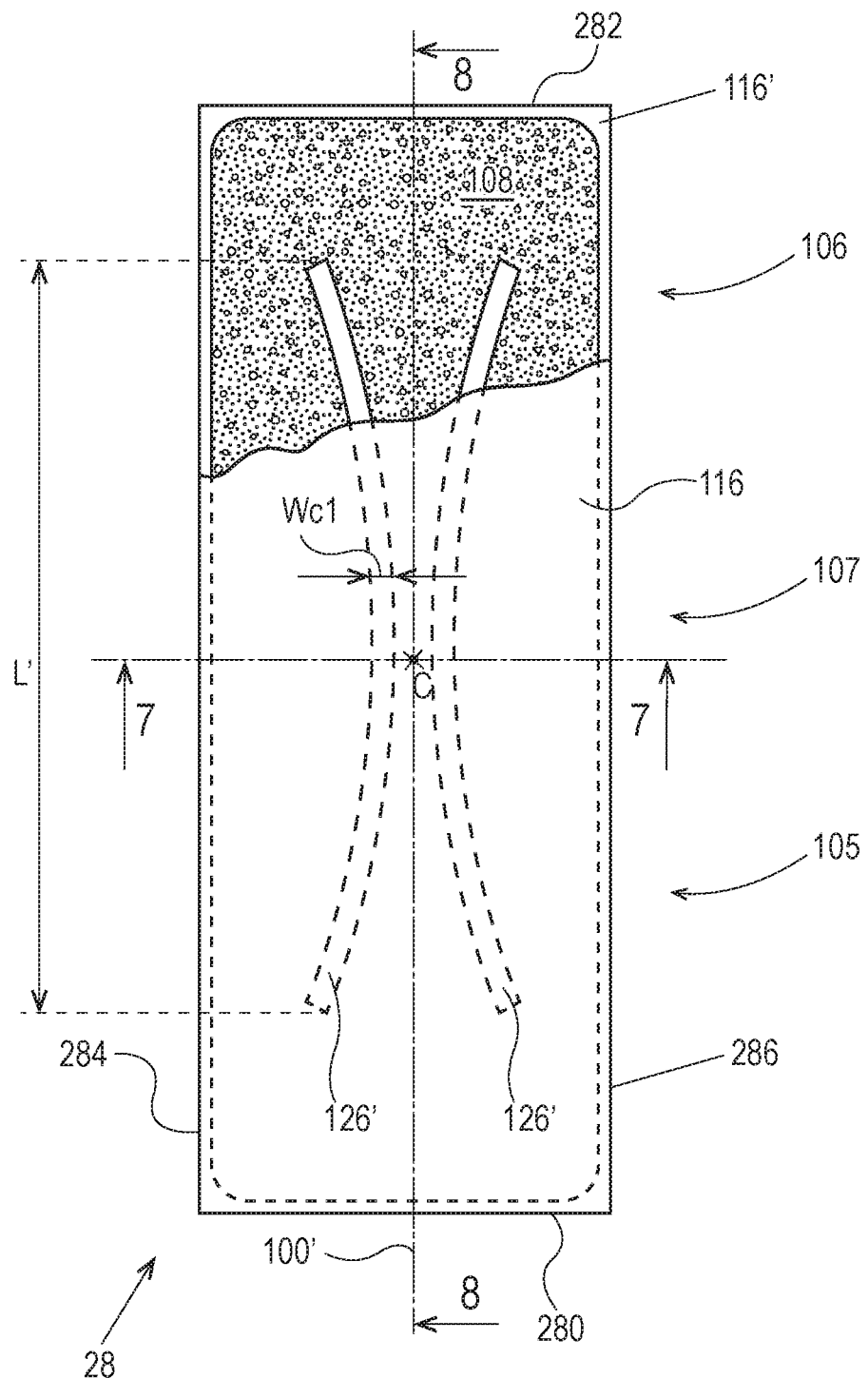
FIG. 15 is a top view of an absorbent core of the absorbent article of FIG. 1 with some layers partially removed.
Figure 16:
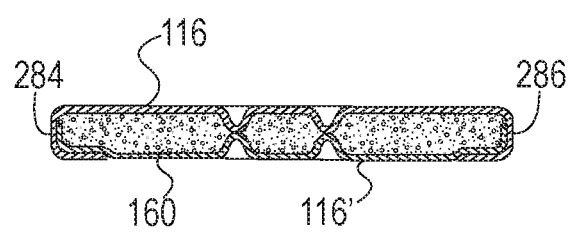
FIG. 16 is a cross-sectional view taken about line 7-7 of the absorbent core of FIG. 15.
Figure 17:
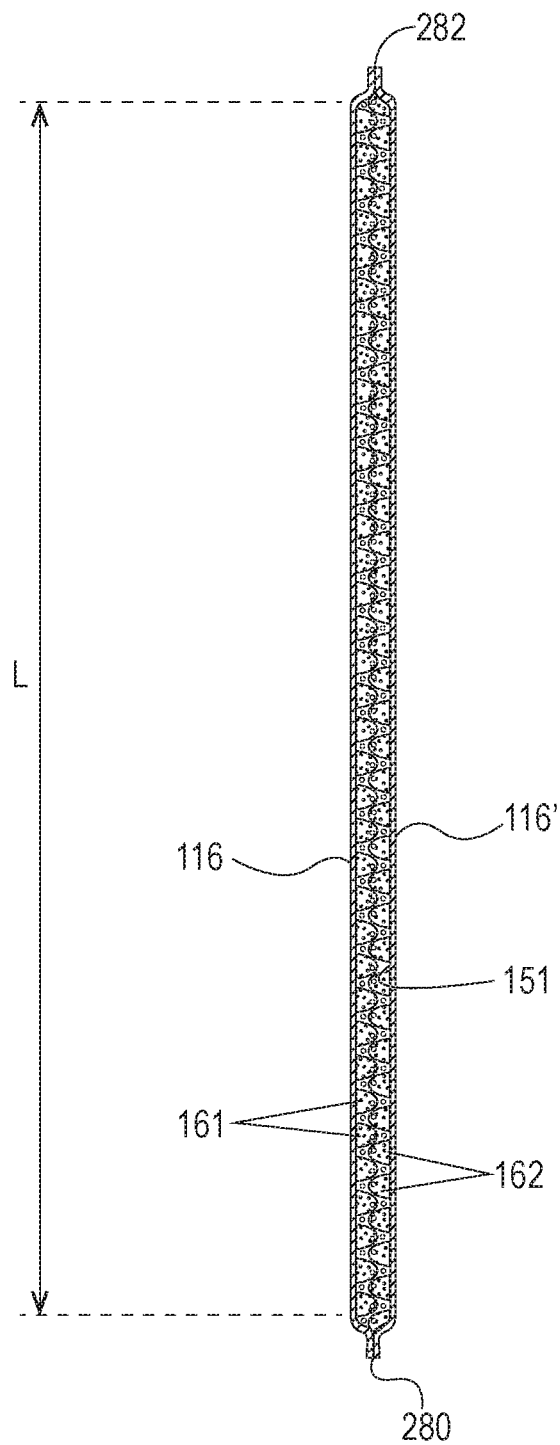
FIG. 17 is a cross-sectional view taken about line 8-8 of the absorbent core of FIG. 15.

The example absorbent core 28 of the absorbent article of FIG. 14 is shown in isolation in FIGS. 15-17. The absorbent core 28 may comprises a front side 280, a rear side 282, and two longitudinal sides 284, 286 joining the front side 280 and the rear side 282. The absorbent core may also comprise a generally planar top side and a generally planar bottom side. The front side 280 of the core 28 is the side of the core 28 intended to be placed towards the first waist edge 13 of the absorbent article. The core 28 may have a longitudinal axis 100' corresponding substantially to the longitudinal axis 100 of the absorbent article, as seen from the top in a planar view as in FIG. 1. The absorbent material may be distributed in higher amount towards the front side than towards the rear side as more absorbency may be required at the front in particular articles. Alternately, the absorbent material may have a non-uniform basis weight or a uniform basis weight across any portion of the core. The front and rear sides of the core may be shorter than the longitudinal sides of the core. The core wrap may be formed by two nonwoven materials, substrates, laminates, or other materials, 116, 116' which may be at least partially sealed along the sides of the absorbent core. The core wrap may be at least partially sealed along its front side 280, rear side 282, and two longitudinal sides 284, 286 so that substantially no absorbent material leaks out of the absorbent core wrap. The first material, substrate, or nonwoven 116 may at least partially surround the second material, substrate, or nonwoven 116' to form the core wrap, as illustrated in FIG. 16. The first material 116 may surround a portion of the second material 116' proximate to the first and second side edges 284 and 286.

The absorbent core of the present disclosure may comprise adhesive, for example, to help in immobilizing the SAP within the core wrap and/or to ensure integrity of the core wrap, in particular when the core wrap is made of two or more substrates. The core wrap may extend to a larger area than strictly needed for containing the absorbent material within.

Cores comprising relatively high amount of SAP with various core designs are disclosed in U.S. Pat. No. 5,599,335 (Goldman), EP 1,447,066 (Busam), WO 95/11652 (Tanzer), U.S. Pat. Publ. No. 2008/0312622A1 (Hundorf), and WO 2012/052172 (Van Malderen).

The absorbent material may be one or more continuous layers present within the core wrap. The absorbent material may be comprised of individual pockets or stripes of absorbent material enclosed within the core wrap. In the first case, the absorbent material may be, for example, obtained by the application of a single continuous layer of absorbent material. The continuous layer of absorbent material, in particular of SAP, may also be obtained by combining two or more absorbent layers having discontinuous absorbent material application pattern, wherein the resulting layer is substantially continuously distributed across the absorbent particulate polymer material area, as disclosed in U.S. Pat. Appl. Publ. No. 2008/0312622A1 (Hundorf), for example. The absorbent core 28 may comprise a first absorbent layer and a second absorbent layer. The first absorbent layer may comprise the first material 116 and a first layer 161 of absorbent material, which may be 100% or less of SAP. The second absorbent layer may comprise the second material 116' and a second layer 162 of absorbent material, which may also be 100% or less of SAP. The absorbent core 28 may also comprise a fibrous thermoplastic adhesive material 151 at least partially bonding each layer of absorbent material 161, 162 to its respective material 116 or 116'. This is illustrated in FIGS. 16-17, as an example, where the first and second SAP layers have been applied as transversal stripes or "land areas" having the same width as the desired absorbent material deposition area on their respective substrate before being combined. The stripes may comprise different amount of absorbent material (SAP) to provide a profiled basis weight along the longitudinal axis of the core 100'. The first material 116 and the second material 116' may form the core wrap.

The fibrous thermoplastic adhesive material 151 may be at least partially in contact with the absorbent material 161, 162 in the land areas and at least partially in contact with the materials 116 and 116' in the junction areas. This imparts an essentially three-dimensional structure to the fibrous layer of thermoplastic adhesive material 151, which in itself is essentially a two-dimensional structure of relatively small thickness, as compared to the dimension in length and width directions. Thereby, the fibrous thermoplastic adhesive material may provide cavities to cover the absorbent material in the land area, and thereby immobilizes this absorbent material, which may be 100% or less of SAP.

The thermoplastic adhesive material 151 may comprise, in its entirety, a single thermoplastic polymer or a blend of thermoplastic polymers, having a softening point, as determined by the ASTM Method D-36-95 "Ring and Ball", in the range between 50° C. and 300° C., and/or the thermoplastic adhesive material may be a hotmelt adhesive comprising at least one thermoplastic polymer in combination with other thermoplastic diluents such as tackifying resins, plasticizers and additives such as antioxidants.

The thermoplastic adhesive used for the fibrous layer may have elastomeric properties, such that the web formed by the fibers on the SAP layer is able to be stretched as the SAP swell. Elastomeric, hot-melt adhesives of these types are described in more detail in U.S. Pat. No. 4,731,066 issued to Korpman on Mar. 15, 1988. The thermoplastic adhesive material may be applied as fibers.

Superabsorbent Polymer (SAP)

"Superabsorbent polymers" ("SAP"), as used herein, refer to absorbent materials which are cross-linked polymeric materials that can absorb at least 10 times their weight of an aqueous 0.9% saline solution as measured using the Centrifuge Retention Capacity (CRC) test (EDANA method WSP 241.2-05E). The SAP used may have a CRC value of more than 20 g/g, more than 24 g/g, from 20 to 50 g/g, from 20 to 40 g/g, or from 24 to 30 g/g, specifically reciting all 0.1 g/g increments within the above-specified ranges and any ranges created therein or thereby. The SAP useful with the present disclosure may include a variety of water-insoluble, but water-swellable polymers capable of absorbing large quantities of fluids.

The superabsorbent polymer may be in particulate form so as to be flowable in the dry state. Particulate absorbent polymer materials may be made of poly(meth)acrylic acid polymers. However, starch-based particulate absorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. The superabsorbent polymer may be polyacrylates and polyacrylic acid polymers that are internally and/or surface cross-linked. Suitable materials are described in the PCT Patent Application Nos. WO 07/047598, WO 07/046052, WO2009/155265, and WO2009/155264, for example. Wuitable superabsorbent polymer particles may be obtained by generally known production processes as described in WO 2006/083584, for example.

The SAP useful for the present disclosure may be of numerous shapes. The term "particles" refers to granules, fibers, flakes, spheres, powders, platelets and other shapes and forms known to persons skilled in the art of superabsorbent polymer particles. The SAP particles may be in the shape of fibers, i.e., elongated, acicular superabsorbent polymer particles. The superabsorbent polymer particles fibers may have a minor dimension (i.e., diameter of the fiber) of less than about 1 mm, usually less than about 500 μm, or less than 250 μm down to 50 μm, specifically reciting all 1 μm increments within the above-specified ranges and any ranges formed therein or thereby. The length of the fibers may be about 3 mm to about 100 mm, specifically reciting all 1 mm increments within the above-specified range and any ranges formed therein or thereby. The fibers may also be in the form of a long filament that may be woven.

SAP may be spherical-like particles. In contrast to fibers, "spherical-like particles" have a longest and a smallest dimension with a particulate ratio of longest to smallest particle dimension in the range of 1-5, where a value of 1 would equate a perfectly spherical particle and 5 would allow for some deviation from such a spherical particle. The superabsorbent polymer particles may have a particle size of less than 850 μm, from 50 to 850 μm, from 100 to 710 μm, or from 150 to 650 μm, specifically reciting all 1 μm increments within the above-specified ranges and any ranges formed therein or thereby, as measured according to EDANA method WSP 220.2-05. SAP having a relatively low particle size may help to increase the surface area of the absorbent material which is in contact with liquid exudates and therefore supports fast absorption of liquid exudates.

The SAP may have a particle size in the range from 45 μm to 4000 μm, more specifically a particle size distribution within the range of from 45 μm to about 2000 μm, or from about 100 µm to about 1000, 850 or 600 µm, specifically reciting all 1 µm increments within the above-specified ranges and any ranges formed therein or thereby. The particle size distribution of a material in particulate form can be determined, for example, by means of dry sieve analysis (EDANA 420.02 "Particle Size distribution). The surface of the SAP may be coated, for example, with a cationic polymer. Certain cationic polymers may include polyamine or polyimine materials. The absorbent core may comprise one or more types of SAP.

For most absorbent articles, liquid discharges from a wearer occur predominately in the front half of the absorbent article, in particular for a diaper. The front half of the absorbent article (as defined by the region between the front edge and the lateral axis 110) may therefore comprise most of the absorbent capacity of the core). Thus, at least 60% of the SAP, or at least 65%, 70%, 75%, 80%, or 85% of the SAP may be present in the front half of the absorbent article, the remaining SAP being disposed in the rear half of the absorbent article. The SAP distribution may be uniform through the core or may have other suitable distributions.

The total amount of SAP present in the absorbent core may also vary according to expected user. Diapers for newborns may require less SAP than infant, child, or adult incontinence diapers. The amount of SAP in the core may be about 5 to 60 g or from 5 to 50 g, specifically reciting all 0.1 increments within the specified ranges and any ranged formed therein or thereby. The average SAP basis weight within the (or "at least one", if several are present) deposition area 8 of the SAP may be at least 50, 100, 200, 300, 400, 500 or more g/m$^2$. The areas of the channels (e.g., 27, 27') present in the absorbent material deposition area 8 are deduced from the absorbent material deposition area to calculate this average basis weight.

Core Wrap

The core wrap may be made of a single substrate, material, or nonwoven folded around the absorbent material, or may comprise two (or more) substrates, materials, or nonwovens which are attached to another. Typical attachments are the so-called C-wrap and/or sandwich wrap. In a C-wrap, as illustrated, for example, in FIGS. 12, 14 and 16, the longitudinal and/or transversal edges of one of the substrates are folded over the other substrate to form flaps. These flaps are then bonded to the external surface of the other substrate, typically by gluing. Other techniques may be used to form a core wrap. For example, the longitudinal and/or transversal edges of the substrates may be bonded together and then folded underneath the absorbent core 28 and bonded in that position.

The core wrap may be formed by any materials suitable for receiving and containing the absorbent material. Typical substrate materials used in the production of conventional cores may be used, in particular paper, tissues, films, wovens or nonwovens, or laminates or composites of any of these. The core wrap may be formed by a nonwoven web, such as a carded nonwoven, spunbond nonwoven ("S") or meltblown nonwoven ("M"), and laminates of any of these. For example, spunmelt polypropylene nonwovens may be suitable, in particular those having a laminate web SMS, or SMMS, or SSMMS, structure, and having a basis weight range of about 5 gsm to about 15 gsm. Suitable materials are disclosed in U.S. Pat. No. 7,744,576, U.S. Pat. Publ. No. 2011/0268932A1, U.S. Pat. Publ. No. 2011/0319848A1, and U.S. Pat. Publ. No. 2011/0250413A1. Nonwoven materials provided from synthetic fibers may also be used, such as PE, PET, and/or PP, for example.

If the core wrap comprises a first substrate, nonwoven or material 116 and a second substrate, nonwoven, or materials 116' these may be made of the same type of material, may be made of different materials, or one of the substrates may be treated differently than the other to provide it with different properties. As the polymers used for nonwoven production are inherently hydrophobic, they may be coated with hydrophilic coatings if placed on the fluid receiving side of the absorbent core. It may be advantageous that the top side of the core wrap, i.e., the side placed closer to the wearer in the absorbent article, be more hydrophilic than the bottom side of the core wrap. A possible way to produce nonwovens with durably hydrophilic coatings is via applying a hydrophilic monomer and a radical polymerization initiator onto the nonwoven, and conducting a polymerization activated via UV light resulting in monomer chemically bound to the surface of the nonwoven. An alternative possible way to produce nonwovens with durably hydrophilic coatings is to coat the nonwoven with hydrophilic nanoparticles, e.g., as described in WO 02/064877.

Permanently hydrophilic nonwovens are also useful. Surface tension, as described in U.S. Pat. No. 7,744,576 (Busam et al.), can be used to measure how permanently a certain hydrophilicity level is achieved. Liquid strike through, as described in U.S. Pat. No. 7,744,576, may be used to measure the hydrophilicity level. The first and/or second substrate may have a surface tension of at least 55, at least 60, or at least 65 mN/m or higher when wetted with saline solution. The substrate may also have a liquid strike through time of less than 5 seconds for a fifth gush of liquid. These values can be measured using the test methods described in U.S. Pat. No. 7,744,576B2: "Determination of Surface Tension" and "Determination of Strike Through" respectively.

Hydrophilicity and wettability are typically defined in terms of contact angle and the strike through time of the fluids, for example, through a nonwoven fabric. This is discussed in detail in the American Chemical Society publication entitled "Contact angle, wettability and adhesion", edited by Robert F. Gould (Copyright 1964). A substrate having a lower contact angle between the water and the surface of substrate may be said to be more hydrophilic than another.

The substrates may also be air-permeable. Films useful herein may therefore comprise micro-pores. The substrate may have an air-permeability of from 40 or from 50, to 300 or to 200 m$^3$/(m$^2$×min), as determined by EDANA method 140-1-99 (125 Pa, 38.3 cm$^2$). The material of the core wrap may alternatively have a lower air-permeability, e.g., being non-air-permeable, for example, to facilitate handling on a moving surface comprising vacuum.

The core wrap may be at least partially sealed along all the sides of the absorbent core so that substantially no absorbent material leaks out of the core. By "substantially no absorbent material" it is meant that less than 5%, less than 2%, less than 1%, or about 0% by weight of absorbent material escape the core wrap. The term "seal" is to be understood in a broad sense. The seal does not need to be continuous along the whole periphery of the core wrap but may be discontinuous along part or the whole of it, such as formed by a series of seal points spaced on a line. A seal may be formed by gluing and/or thermal bonding.

If the core wrap is formed by two substrates 116, 116', four seals may be used to enclose the absorbent material 160 within the core wrap. For example, a first substrate 116 may be placed on one side of the core (the top side as represented in the Figures) and extend around the core's longitudinal edges to at least partially wrap the opposed bottom side of the core. The second substrate 116' may be present between the wrapped flaps of the first substrate 116 and the absorbent material 160. The flaps of the first substrate 116 may be glued to the second substrate 116' to provide a strong seal. This so called C-wrap construction may provide benefits such as improved resistance to bursting in a wet loaded state compared to a sandwich seal. The front side and rear side of the core wrap may then also be sealed by gluing the first substrate and second substrate to another to provide complete encapsulation of the absorbent material across the whole of the periphery of the core. For the front side and rear side of the core, the first and second substrates may extend and may be joined together in a substantially planar direction, forming for these edges a so-called sandwich construction. In the so-called sandwich construction, the first and second substrates may also extend outwardly on all sides of the core and be sealed flat, or substantially flat, along the whole or parts of the periphery of the core typically by gluing and/or heat/pressure bonding. Neither the first nor the second substrates need to be shaped, so that they can be rectangularly cut for ease of production but other shapes are within the scope of the present disclosure.

The core wrap may also be formed by a single substrate which may enclose as in a parcel wrap the absorbent material and be sealed along the front side and rear side of the core and one longitudinal seal.

SAP Deposition Area

The absorbent material deposition area 108 may be defined by the periphery of the layer formed by the absorbent material 160 within the core wrap, as seen from the top side of the absorbent core. The absorbent material deposition area 108 may have various shapes, in particular, a so-called "dog bone" or "hour-glass" shape, which shows a tapering along its width towards the middle or "crotch" region of the core. In this way, the absorbent material deposition area 108 may have a relatively narrow width in an area of the core intended to be placed in the crotch region of the absorbent article. This may provide better wearing comfort. The absorbent material deposition area 108 may thus have a width (as measured in the transversal direction) at its narrowest point which is less than about 100 mm, 90 mm, 80 mm, 70 mm, 60 mm, or even less than about 50 mm. This narrowest width may further be at least 5 mm, or at least 10 mm, smaller than the width of the deposition area 8 at its largest point in the front and/or rear regions deposition area 108. The absorbent material deposition area 108 may also be generally rectangular, for example as shown in FIG. 15, but other deposition areas, such as a "T," "Y," "hour-glass," or "dog-bone" shapes are also within the scope of the present disclosure.

Figure 18:
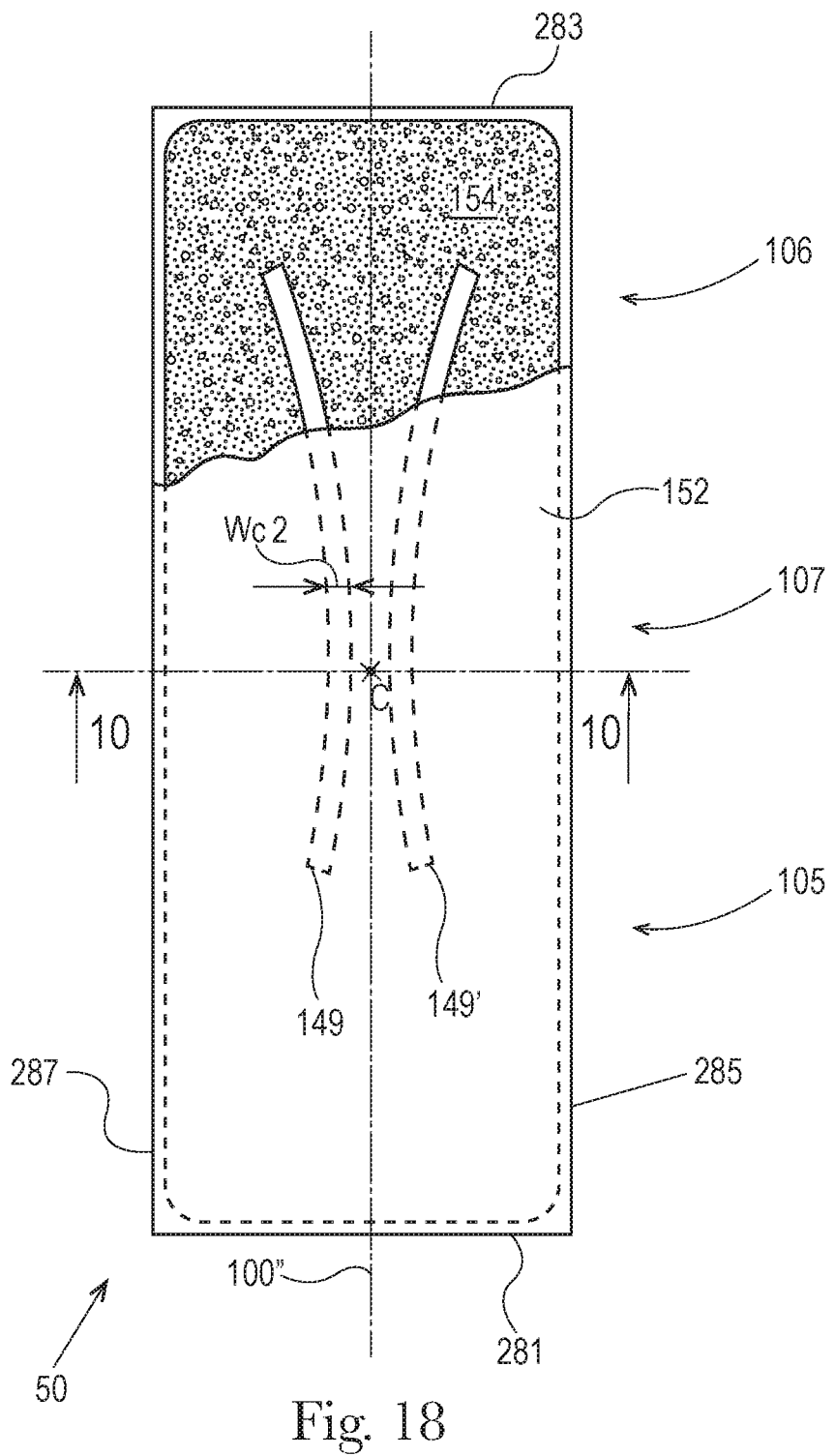
FIG. 18 is a top view of a liquid management system of the absorbent article of FIG. 1 with some layers partially removed.

The basis weight (amount deposited per unit of surface) of the SAP may also be varied along the deposition area 108 to create a profiled distribution of absorbent material, in particular SAP, in the longitudinal direction, in the transversal direction, or both directions of the core. Hence, along the longitudinal axis of the core, the basis weight of absorbent material may vary, as well as along the transversal axis, or any axis parallel to any of these axes. The basis weight of SAP in areas of relatively high basis weight may thus be at least 10%, 20%, 30%, 40%, or 50% higher than in an area of relatively low basis weight. The SAP present in the absorbent material deposition area 108 at the level of the crotch point C, as illustrated in FIG. 18, may have more SAP per unit of surface deposited as compared to another area of the absorbent material deposition area 108.

The absorbent material may be deposited using known techniques, which may allow relatively precise deposition of SAP at relatively high speed. In particular, the SAP printing technology as disclosed in U.S. Pat. Publ. No. 2008/0312617 and U.S. Pat. Publ. No. 2010/0051166A1 (both to Hundorf et al.) may be used. This technique uses a printing roll to deposit SAP onto a substrate disposed on a grid of a support which may include a plurality of cross bars extending substantially parallel to and spaced from one another so as to form channels extending between the plurality of cross-bars. This technology allows high-speed and precise deposition of SAP on a substrate. The channels of the absorbent core may be formed for example by modifying the pattern of the grid and receiving drums so that no SAP is applied in areas corresponding to the channels. EP application number 11169396.6 discloses this modification in more details Channels in the Absorbent Core The absorbent material deposition area 108 may comprise at least one channel 126 free of, or substantially free of, absorbent material, wherein the at least one channel is at least partially oriented in the longitudinal direction of the absorbent article 100 (i.e., has a longitudinal vector component). Other channels may be at least partially oriented in the lateral direction (i.e., has a lateral vector component) or in any other direction. If the following, the plural form "channels" will be used to mean "at least one channel". The channels may have a length L' projected on the longitudinal axis 100 of the absorbent article that is at least 10% of the length L of the absorbent article. The channels may also be circular, oblong, or be in the shape of a variety of other closed polygons. The channels may be formed in various ways. For example, the channels may be formed by zones within the absorbent material deposition area 108 which may be substantially free of, or free of, absorbent material, in particular, SAP. In addition or alternatively, the channel(s) may also be formed by continuously or discontinuously bonding the top side of the core wrap to the bottom side of the core wrap through the absorbent material deposition area 108. The channels may be continuous but it is also envisioned that the channels may be intermittent. The liquid management system 150, or another layer of the absorbent article, may also comprise channels, which may or not correspond to the channels of the absorbent core, as described in more detail below.

The channels may be present at least at the same longitudinal level as the crotch point C or the lateral axis 110 in the absorbent article, as represented in FIG. 15 with the two longitudinally extending channels 126, 126'. When forming part of the absorbent article, the channels may also extend from the crotch region 107 or may be present in the front waist region 105 and/or in the rear waist region 106 of the absorbent article. When the absorbent core 28 is disposed in the absorbent article 20, the crotch region 37 of the absorbent article 20 generally is aligned with the crotch region 107 of the absorbent core 28, the first waist region 36 of the absorbent article generally is aligned with the front waist region 105 of the absorbent core, and the second waist region 38 of the absorbent article generally is aligned with the rear waist region 106 of the absorbent core.

The absorbent core 28 may also comprise more than two channels, for example, at least 3, at least 4, at least 5, or at least 6 or more. Shorter channels may also be present in the absorbent core, for example in the front waist region 105 or the rear waist region 106 of the absorbent core. The channels may comprise one or more pairs of channels symmetrically arranged, or otherwise arranged relative to the longitudinal axis 100'.

The channels may be particularly useful in the absorbent core when the absorbent material deposition area is rectangular, as the channels may improve the flexibility of the core to an extent that there is less advantage in using a non-rectangular (shaped) core. Of course channels may also be present in a layer of SAP having a shaped deposition area.

The channels may extend substantially longitudinally, which means that each channel extends more in the longitudinal direction than in the transverse direction, or at least twice as much in the longitudinal direction than in the transverse direction (as measured after projection on the respective axis). The channels may extend substantially laterally, which means that each channel extends more in the lateral direction than in the longitudinal direction, or at least twice as much in the transverse direction than in the longitudinal direction (as measured after projection on the respective axis).

The channels may be completely oriented longitudinally and parallel to the longitudinal axis or completely oriented transversely and parallel to the lateral axis, but also may be curved. Some or all of the channels of the core, in particular the channels present in the crotch region 107, may be concave towards the longitudinal axis 100, as, for example, represented in FIG. 15 for the pair of channels 126, 126', such that they bend towards the longitudinal axis 100'. The channels 126, 126' may also be convex, such they bend away from the longitudinal axis 100', or have any other suitable arrangement. The radius of curvature may typically be at least equal (and may be at least 1.5 or at least 2.0 times this average transverse dimension) to the average transverse dimension of the absorbent layer; and also straight but under an angle of (e.g., from 5°) up to 30°, up to 20°, up to 10° with a line parallel to the longitudinal axis. The radius of curvature may be constant for a channel, or may vary along its length. This may also include channels with an angle therein, provided the angle between two parts of a channel is at least 120°, at least 150°; and in any of these cases, provided the longitudinal extension of the channel is more than the transverse extension. The channels may also be branched. For example, a central channel superposed with the longitudinal axis in the crotch region 107 which branches towards the second waist edge 14 and/or towards the first waist edge 13 of the absorbent article.

There may be a channel coinciding with the longitudinal axis 100 of the absorbent article 100 or the core 100', while alternately, there may not be a channel that coincides with the longitudinal axis 100, 100'. When present as symmetrical pairs relative to the longitudinal axis 100, 100', the channels may be spaced apart from one another over their whole longitudinal dimension. The smallest spacing distance may be at least 5 mm, at least 10 mm, or at least 15 mm, for example.

Furthermore, in order to reduce the risk of fluid leakages, the longitudinal main channels may not extend up to any of the edges of the absorbent material deposition area 108, and may therefore be fully encompassed within the absorbent material deposition area 108 of the core. The smallest distance between a channel and the closest edge of the absorbent material deposition area 108 may be at least 5 mm.

The channels may have a width Wc1 along at least part of its length which is at least 2 mm, at least 3 mm, at least 4 mm, up to for example 20 mm, 16 mm, or 12 mm, for example. The width of the channel may be constant through substantially the whole length of the channel or may vary along its length. When the channels are formed by absorbent material-free zones within the absorbent material deposition area 108, the width of the channels is considered to be the width of the material-free zones, disregarding the possible presence of the core wrap within the channels. If the channels are not formed by absorbent material-free zones, for example mainly through bonding of the core wrap through the absorbent material zone, the width of the channels is the width of this bonding.

At least some or all of the channels may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the upper side and lower side of the core wrap (e.g., the first substrate 116 and the second substrate 116') and/or the topsheet 24 to the backsheet 26 together through the channels. Typically, an adhesive may be used to bond both sides of the core wrap or the topsheet and the a backsheet through the channels, but it is possible to bond via other known processes, such as pressure bonding, ultrasonic bonding, heat bonding, or combination thereof. The core wrap or the topsheet 24 and the backsheet 26 may be continuously bonded or intermittently bonded along the channels. The channels may advantageously remain or become visible at least through the topsheet and/or backsheet when the absorbent article is fully loaded with a fluid. This may be obtained by making the channels substantially free of SAP, so they will not swell, and sufficiently large so that they will not close when wet. Furthermore, bonding the core wrap to itself or the topsheet to the backsheet through the channels may be advantageous.

The absorbent core 28 may comprise at least three channels or four channels. These channels may be free of, or substantially free of (e.g., less than 10%, less than 5%, less than 3%, less than 2%, or less than 1%), superabsorbent polymers and may be at least partially oriented in the longitudinal direction and/or may be at least partially oriented in the lateral direction. The longitudinal lengths of the channels 126 and 126' about the longitudinal axis 100' may be the same, substantially the same (e.g., within 2 mm or less of each other), or different. The average lateral width over the longitudinal lengths of the channels 126 and 126' may be the same, substantially the same, or may be different. The average lateral width of the channels 126, 126' may be the same, substantially the same, or different.

In addition to the first and second channels 126 and 126', an absorbent core 28 may comprise a pocket (not shown) in the crotch region 107 and/or the rear waist region 106 and one or more channels in the rear waist region 106 and/or the crotch region 107. Alternately, a pocket may be in the crotch region 107 and/or the front waist region 105 and the one or more channels may be in the crotch region 107 and/or the front waist region 105. The pocket and the one or more channels may be BM pockets or channels and/or urine management pockets and/or channels.

Liquid Management System:

The LMS 150 of the present disclosure may sometimes be referred to as acquisition-distribution system ("ADS") or an acquisition system. One function of the LMS 150 is to quickly acquire the fluid and distribute it to the absorbent core in an efficient manner. The LMS 150 may comprise one, two or more layers, which may form a unitary layer or may remain as discrete layers which may be attached to each other. The LMS 150 may comprise two layers: a distribution layer 154 and an acquisition layer 152 disposed between the absorbent core and the topsheet.

The LMS 150 may comprise SAP as this may slow the acquisition and distribution of the fluid. The LMS may be substantially free (e.g., 80%, 85%, 90%, 95%, or 99% free of) or completely free of SAP. The LMS may also comprise one or more of a variety of other suitable types of materials, such as opened-cell foam, air-laid fibers, or carded, resin bonded nonwoven materials, for example. Suitable example LMSs are described in WO 2000/59430 (Daley), WO 95/10996 (Richards), U.S. Pat. No. 5,700,254 (McDowall), and WO 02/067809 (Graef), for example. Any of the example LMSs 150 disclosed herein may be positioned in an absorbent article: (1) intermediate a liquid pervious material or topsheet or secondary topsheet and an absorbent core; (2) intermediate an absorbent core and a liquid impervious material or backsheet; (3) intermediate an absorbent core and a liquid distribution layer; (4) intermediate a liquid distribution layer and a liquid impervious material or backsheet, or may be otherwise located within the absorbent article. More than one LMS 150 may be provided in an absorbent article. The one or more LMSs 150 may be provided above and/or below one or more absorbent cores.

Distribution Layer

The LMS 150 may comprise a distribution layer 154. The distribution layer 154 may comprise at least 50% by weight of cross-linked cellulose fibers, for example. The cross-linked cellulosic fibers may be crimped, twisted, or curled, or a combination thereof including crimped, twisted, and curled. This type of material is disclosed in U.S. Pat. Publ. No. 2008/0312622 A1 (Hundorf). The cross-linked cellulosic fibers provide higher resilience and therefore higher resistance to the first absorbent layer against the compression in the product packaging or in use conditions, e.g., under baby weight. This provides the core with a higher void volume, permeability, and liquid absorption, and hence reduced leakage and improved dryness.

Example chemically cross-linked cellulosic fibers suitable for a distribution layer are disclosed in U.S. Pat. Nos. 5,549,791, 5,137,537, WO 9534329, or U.S. Pat. App. Publ. No. 2007/118087. Example cross-linking agents include polycarboxylic acids such as citric acid and/or polyacrylic acids such as acrylic acid and maleic acid copolymers.

The distribution layer 154 comprising cross-linked cellulose fibers of the present disclosure may comprise other fibers, but this layer may advantageously comprise at least 50%, or 60%, or 70%, or 80%, or 90%, or even up to 100%, by weight of the layer, of cross-linked cellulose fibers (including the cross-linking agents). Examples of such mixed layer of cross-linked cellulose fibers may comprise about 70% by weight of chemically cross-linked cellulose fibers, about 10% by weight polyester (PET) fibers, and about 20% by weight untreated pulp fibers. In another example, the layer of cross-linked cellulose fibers may comprise about 70% by weight chemically cross-linked cellulose fibers, about 20% by weight lyocell fibers, and about 10% by weight PET fibers. In another example, the layer may comprise about 68% by weight chemically cross-linked cellulose fibers, about 16% by weight untreated pulp fibers, and about 16% by weight PET fibers. In another example, the layer of cross-linked cellulose fibers may comprise from about 90-100% by weight chemically cross-linked cellulose fibers.

The distribution layer 154 may be a material having a water retention value of from 25 to 60 or from 30 to 45, measured as indicated in the procedure disclosed in U.S. Pat. No. 5,137,537.

The distribution layer may typically have an average basis weight of from 30 to 400 g/m$^2$ or from 100 to 300 g/m$^2$, specifically reciting all 1.0 g/m$^2$ increments within the above-specified ranges and any ranges formed therein or thereby. The density of the distribution layer may vary depending on the compression of the absorbent article, but may be between 0.03 to 0.15 g/cm3 or 0.08 to 0.10 g/cm3, specifically reciting all 1.0 g/cm3 increments within the above-specified ranges and any ranges formed therein or thereby, measured at 0.30 psi (2.07 kPa)

Acquisition Layer

The LMS 150 may alternatively or additionally comprise an acquisition layer 152. The acquisition layer 152 may be disposed, for example, between the distribution layer 154 and the topsheet 24. The acquisition layer 152 may be or may comprise a non-woven material, such as an SMS or SMMS material, comprising a spunbonded, a melt-blown and a further spunbonded layer or alternatively a carded chemical-bonded nonwoven. The acquisition layer 152 may comprise air or wet-laid cellulosic, cross-linked cellulosic, or synthetic fibers, or blends thereof. The acquisition layer 152 may comprise a roll-stock web of synthetic fibers (which may be processed to increase void space, such as by solid state formation), or a combination of synthetic and cellulosic fibers, bonded together to form a highloft material. Alternatively, the acquisition layer 152 may comprise absorbent open cell foam. The nonwoven material may be latex bonded. Example acquisition layers are disclosed in U.S. Pat. No. 7,786,341. Carded, resin-bonded nonwovens may be used, in particular where the fibers used are solid round or round hollow PET staple fibers (50/50 or 40/60 mix of 6 denier and 9 denier fibers). An example binder is a butadiene/styrene latex. Nonwovens have the advantage that they can be manufactured outside the converting line and stored and used as a roll of material. The acquisition layer 152 may be stabilized by a latex binder, for example a styrene-butadiene latex binder (SB latex).

A further acquisition layer may be used in addition to a first acquisition layer described above. For example, a tissue, nonwoven, or other layer may be placed between the first acquisition layer and the distribution layer. The tissue may have enhanced capillarity distribution properties compared to the acquisition layer described above. The tissue, nonwoven, or other layer and the first acquisition layer may be of the same size or may be of a different size. For example, the tissue, nonwoven, or other layer may extend further in the rear of the absorbent article than the first acquisition layer. An example of hydrophilic tissue is a 13-15 gsm high wet strength made of cellulose fibers from supplier Havix.

The composition used to form fibers for the base substrate of the acquisition layer 152 may comprise thermoplastic polymeric and non-thermoplastic polymeric materials. The thermoplastic polymeric material must have rheological characteristics suitable for melt spinning. The molecular weight of the polymer must be sufficient to enable entanglement between polymer molecules and yet low enough to be melt spinnable. For melt spinning, thermoplastic polymers have molecular weights below about 1,000,000 g/mol; from about 5,000 g/mol to about 750,000 g/mol; from about 10,000 g/mol to about 500,000 g/mol; and from about 50,000 g/mol to about 400,000 g/mol. Unless specified elsewhere, the molecular weight indicated is the number average molecular weight.

The thermoplastic polymeric materials are able to solidify relatively rapidly, preferably under extensional flow, and form a thermally stable fiber structure, as typically encountered in known processes such as a spin draw process for staple fibers or a spunbond continuous fiber process. Polymeric materials may comprise, but are not limited to, polypropylene and polypropylene copolymers, polyethylene and polyethylene copolymers, polyester and polyester copolymers, polyamide, polyimide, polylactic acid, polyhydroxyalkanoate, polyvinyl alcohol, ethylene vinyl alcohol, polyacrylates, and copolymers thereof and mixtures thereof. Other suitable polymeric materials include thermoplastic starch compositions as described in detail in U.S. Pat. App. Publ. No. 2003/0109605A1 and 2003/0091803. Other suitable polymeric materials include ethylene acrylic acid, polyolefin carboxylic acid copolymers, and combinations thereof. The polymers described in U.S. Pat. Nos. 6,746,766, 6,818,295, and 6,946,506 and U.S. patent application Ser. No. 03/009,2343. Common thermoplastic polymer fiber grade materials may be used, such as polyester based resins, polypropylene based resins, polylactic acid based resin, polyhydroxyalkonoate based resin, and polyethylene based resin and combination thereof. Some articles use polyester and polypropylene based resins.

Nonlimiting examples of thermoplastic polymers suitable for use in the present disclosure include aliphatic polyesteramides; aliphatic polyesters; aromatic polyesters including polyethylene terephthalates (PET) and copolymer (coPET), polybutylene terephthalates and copolymers; polytrimethylene terephthalates and copolymers; polypropylene terephthalates and copolymers; polypropylene and propylene copolymers; polyethylene and polyethylene copolymers; aliphatic/aromatic copolyesters; polycaprolactones; poly (hydroxyalkanoates) including poly(hydroxybutyrate-co-hydroxyvalerate), poly(hydroxybutyrate-co-hexanoate), or other higher poly(hydroxybutyrate-co-alkanoates) as referenced in U.S. Pat. No. 5,498,692 to Noda; polyesters and polyurethanes derived from aliphatic polyols (i.e., dialkanoyl polymers); polyamides; polyethylene/vinyl alcohol copolymers; lactic acid polymers including lactic acid homopolymers and lactic acid copolymers; lactide polymers including lactide homopolymers and lactide copolymers; glycolide polymers including glycolide homopolymers and glycolide copolymers; and mixtures thereof. Additional examples include aliphatic polyesteramides, aliphatic polyesters, aliphatic/aromatic copolyesters, lactic acid polymers, and lactide polymers.

Suitable lactic acid and lactide polymers include those homopolymers and copolymers of lactic acid and/or lactide which have a weight average molecular weight generally ranging from about 10,000 g/mol to about 600,000 g/mol; from about 30,000 g/mol to about 400,000 g/mol; or from about 50,000 g/mol to about 200,000 g/mol. An example of commercially available polylactic acid polymers includes a variety of polylactic acids that are available from the Chronopol Incorporation located in Golden, Colo., and the polylactides sold under the tradename EcoPLAO. Examples of suitable commercially available polylactic acid are NATUREWORKS from Cargill Dow and LACEA from Mitsui Chemical. Homopolymers or copolymers of poly lactic acid having a melting temperature from about 160° to about 175° C. may be used. Modified poly lactic acid and different stereo configurations may also be used, such as poly L-lactic acid and poly D,L-lactic acid with D-isomer levels up to 75%. Optional racemic combinations of D and L isomers to produce high melting temperature PLA polymers may be used. These high melting temperature PL polymers are special PLA copolymers (with the understanding that the D-isomer and L-isomer are treated as different stereo monomers) with melting temperatures above 180° C. These high melting temperatures are achieved by special control of the crystallite dimensions to increase the average melting temperature.

Depending upon the specific polymer used, the process, and the final use of the fiber, more than one polymer may be desired. The polymers of the present disclosure are present in an amount to improve the mechanical properties of the fiber, the opacity of the fiber, optimize the fluid interaction with the fiber, improve the processability of the melt, and improve attenuation of the fiber. The selection and amount of the polymer will also determine if the fiber is thermally bondable and affect the softness and texture of the final product. The fibers of the present disclosure may comprise a single polymer, a blend of polymers, or be multicomponent fibers comprising more than one polymer. The fibers in the present disclosure are thermally bondable.

Multiconstituent blends may be desired. For example, blends of polyethylene and polypropylene (referred to hereafter as polymer alloys) can be mixed and spun using this technique. Another example would be blends of polyesters with different viscosities or monomer content. Multicomponent fibers can also be produced that contain differentiable chemical species in each component. Non-limiting examples would include a mixture of 25 melt flow rate (MFR) polypropylene with 50MFR polypropylene and 25MFR homopolymer polypropylene with 25MFR copolymer of polypropylene with ethylene as a comonomer.

The polymeric materials may have melting temperatures above 110° C., above 130° C., above 145° C., above 160° C. or above 200° C. Polymers with high glass transition temperatures may be desired. Glass transition temperatures in the end-use fiber form may be used that are above −10° C., which are above 0° C., which are above 20° C., or that are above 50° C. This combination of properties produces fibers that are stable at elevated temperatures. Examples of materials of this type are polypropylene, polylactic acid based polymers, and polyester terephthalate (PET) based polymer systems.

Channels in Liquid Management System

The LMS 150 of the absorbent article 20 may comprise channels that may generally enable better conformation of the absorbent article to the wearer's anatomy, leading to increased freedom-of-movement and reduced gapping. One or more of the channels of the LMS 150 may be configured to work in concert with various channels in the absorbent core 28, as discussed above. Furthermore, channels in the LMS 150 may also provide increased void space to hold and distribute urine, feces or other body exudates within the absorbent article, leading to reduced leakage and skin contact. Channels in the LMS 150 may also provide internal serviceable indicia, especially when highlighted via physical differences in texture, color and/or pattern, to facilitate achieving the correct alignment of the absorbent article on a wearer. Thus, such physical differences may be, for example, visually and/or tactilely noticeable.

Similar to the channels in the absorbent core 28, a channel in the LMS 150 may be any region in a layer, or extending through more than one layer, that has a substantially lower basis weight or thickness than the surrounding material, as set forth in the definition of "channel" above. The channels in the LMS 150 may also serve to reduce the tension forces to enable controlled bending and maintain the LMS 150 in close proximity to the absorbent core 28. Thus, the presence of channels in the LMS 150, which may or may not be aligned with any channels in an underlying absorbent core 28, may generally function as hinges to allow for a more flexible composite structure. In some cases, for example, the channels of the LMS 150 allow for the LMS 150 to move toward the absorbent core 28 in a controlled bending arrangement, thereby limiting the separation between the LMS 150 and the absorbent core 28. Moreover, a channel in the LMS 150 may assist in the routing of fluid or other bodily exudates from one region of the absorbent article 20 to another region of the absorbent article 20. Such routing may desirably improve the overall distribution of fluid through the absorbent article 20 and may lead to increase in comfort, wearability, or longevity of the article.

For multi-layered LMSs, the channels may be present in one or more layers of the LMS 150 and may vary in their dimensions in all three planes of reference. The width of a given channel in the LMS 150 may vary in the longitudinal direction (i.e., in a direction substantially parallel to the longitudinal axis of the absorbent article). A channel may also have a different width, length, and/or volume in front of a lateral axis or lateral separation element of the absorbent article than behind the lateral axis or lateral separation element. The channels of the LMS 150 may have a range of widths, lengths, shapes, volumes, and patterns, similar to the channels described above with regard to the absorbent core 28.

A channel in the LMS 150 of the back portion of an absorbent article may be referred to as a bowel movement "BM" channel or BM pocket and may be generally aligned with and overlapping the longitudinal centerline in the back portion of the absorbent article or may be otherwise located. A portion of the channel may be positioned in the LMS 150 such that is generally aligns with the wearer's ischium and may have a width in the range of about 10 mm to about 30 mm, for example. Rearward of this location, the channel width may or may not increase gradually or abruptly to about 25 mm to about 150 mm, for example. The width of the channel may decrease again as it approaches the rear waist region of the absorbent article. The volume of the channel may be in the range of about 10 cm$^3$ to about 200 cm$^3$, for example. The ratio of the maximum channel width to the width at the wearer's ischium may range from about 1.5 to about 15. At least about 60%, at least about 70%, at least about 75%, at least about 80%, or at least about 85% of the total volume of all the channels in the LMS may lie rearward of the lateral centerline. At least about 60% to about 85% of the total volume of all the channels in the LMS may lie rearward of the lateral centerline.

One or more channels in the LMS 150 may at least partially overlap, or fully overlap, a channel in the absorbent core 28, creating a deeper recess in the overlapping regions. For articles where the LMS 150 includes more than one layer, the layer closest to the absorbent core 28 may include a channel. One or more layers in the structure, such as the topsheet 24, an acquisition layer 152, distribution layer 154, or other layers, may be bonded to an element of the absorbent core 28 in this region to increase the depth of the combined channel. The channel in the acquisition layer 152 of the LMS 150 and the channel in the absorbent core 28 may be coincident such that the channels are completely overlapping. Alternately, channels in the LMS and storage layers may have no overlapping area. Other articles have a vertical overlap between the channels in the two layers that encompass the intervening range such that they partially overlap. Example channel arrangements are described in more detail below with regard to FIGS. 28-42.

Where the topsheet 24 includes apertures, the apertures may be fully or partially aligned or overlapping with at least one channel in the LMS 150, whereas in other articles, the apertures may not align with any channel in the LMS 150.

At least one layer on or proximate to the garment-facing side and/or the wearer-side of the absorbent article 20 may include a pattern, image, color, or tint resulting in an increased visual distinctiveness of the channel of the LMS 150 and serve as an internal serviceable indicia to facilitate more accurate alignment of the absorbent article on the wearer during the application process.

Referring again to FIGS. 12-14, the LMS 150 in the illustrated article is shown defining two channels 149, 149'. The channels 149, 149' are at least partially oriented in the longitudinal direction of the absorbent article 100 (i.e., has a longitudinal vector component). Other channels in the LMS may be at least partially oriented in the lateral direction (i.e., has a lateral vector component) or in any other direction and the channels in the LMS 150 may be continuous or intermittent. Some channels in the LMS may be round, oblong, square, rectangular, triangular or any other suitable shape. The channels may have a length projected on the longitudinal axis 100 of the absorbent article that is at least 10% of the length L of the absorbent article. The channels may be formed in various ways. For example, the channels may be formed by zones within the LMS 150 which may be substantially free of, or free of, acquisition or distribution material.

Figure 12:
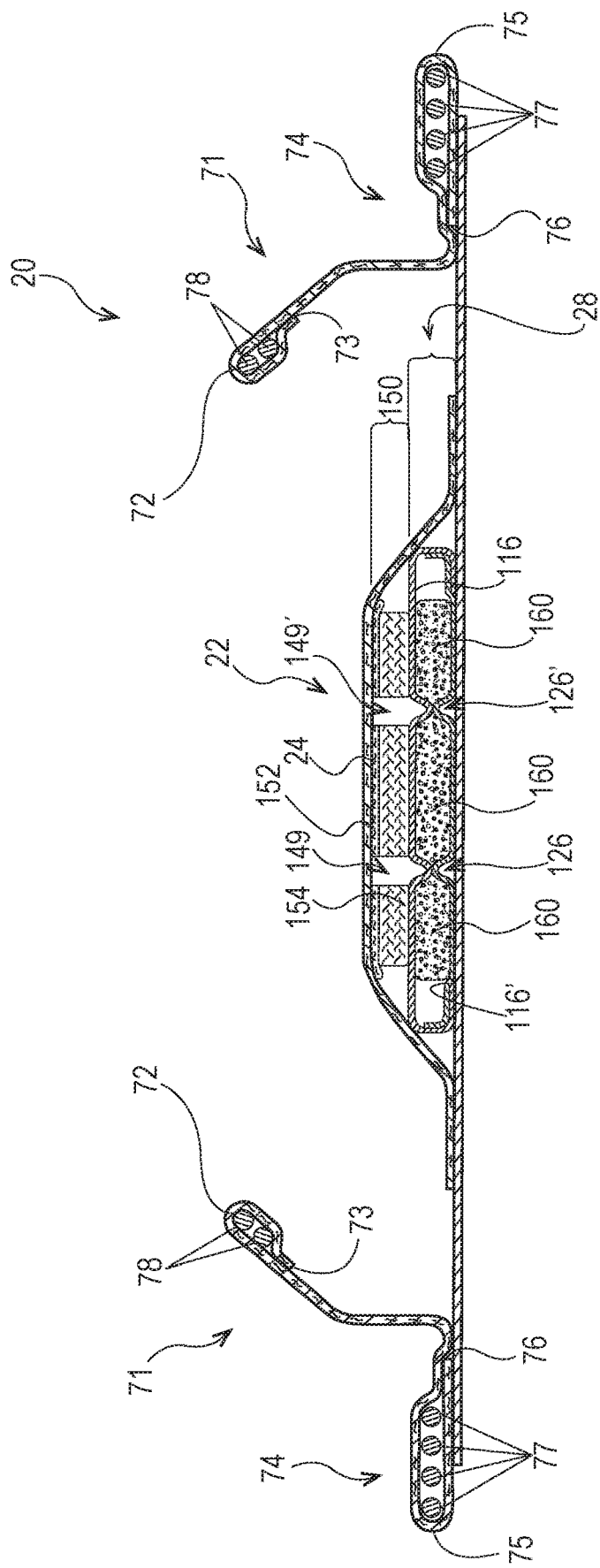
FIG. 12 is a cross-sectional view taken about line 2-2 of the absorbent article of FIG. 1.
Figure 13:
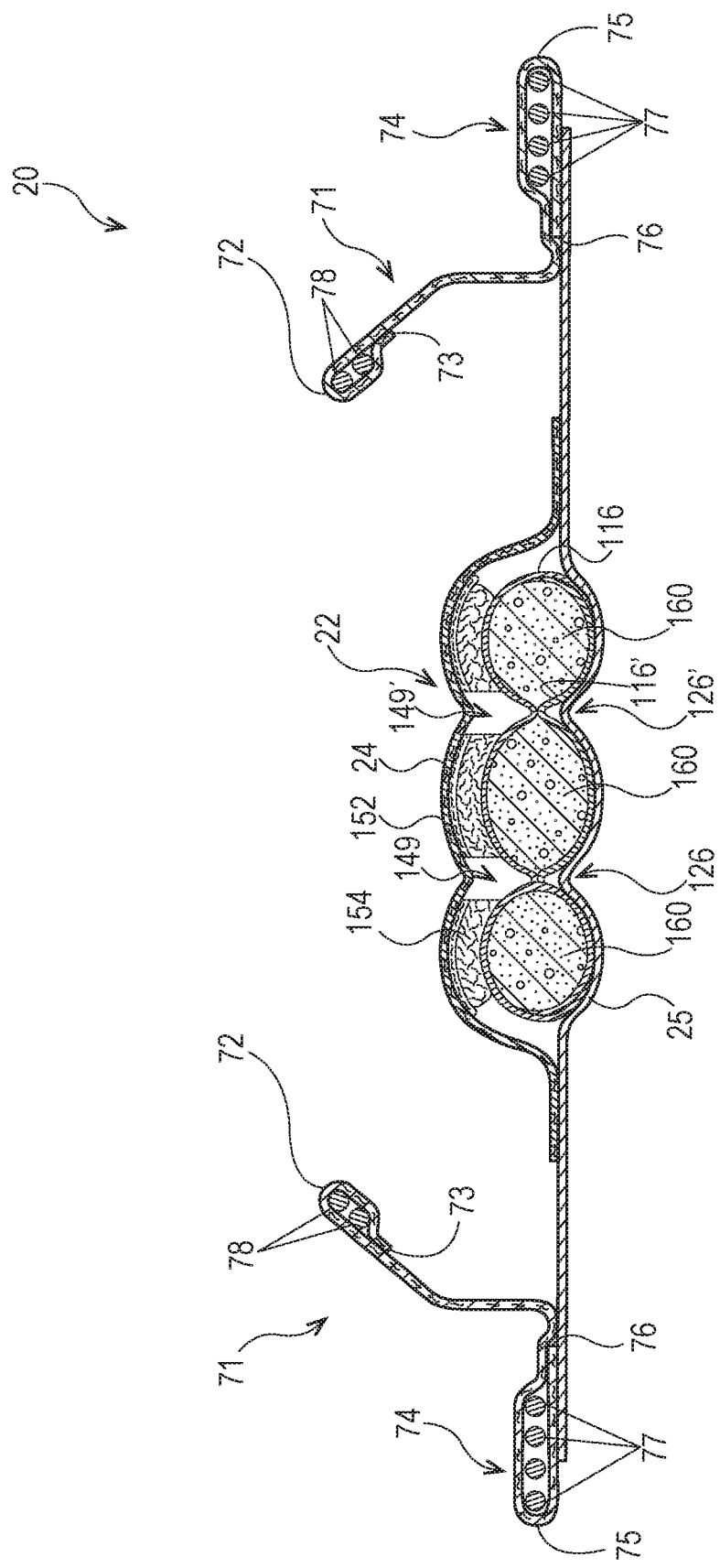
FIG. 13 is a view of the absorbent article of FIG. 12 where the absorbent article has been loaded with fluid.

The channels of the LMS 150 may be present at least at the same longitudinal level as the crotch point C or the lateral axis 110 in the absorbent article. The channels may also extend from the crotch region 107 or may be present in the front waist region 105 and/or in the rear waist region 106 of the absorbent article. In FIGS. 12-14, the channels 149, 149' are generally coincident with channels 126, 126', with channels 126, 126' having a longer length in the longitudinal direction towards the first waist edge 13 of the absorbent article 20.

The LMS 150 may define any suitable number of channels, such as at least one, more than two channels, at least three, at least four, at least five, or at least six or more. Shorter channels may also be present, for example in the rear waist region 106 or the front waist region 105 of the LMS 150. The channels of the LMS 150 may comprise one or more pairs of channels symmetrically arranged, or otherwise arranged relative to the longitudinal axis 100 and/or the lateral axis 110, or other transverse axis.

The channels of the LMS 150 may extend substantially longitudinally, which means that each channel extends more in the longitudinal direction than in the transverse direction, or at least twice as much in the longitudinal direction than in the transverse direction (as measured after projection on the respective axis). The channels of the LMS 150 may extend substantially laterally, which means that each channel extends more in the lateral direction than in the longitudinal direction, or at least twice as much in the transverse direction than in the longitudinal direction (as measured after projection on the respective axis).

Similar to the channels in the absorbent core, the channels of the LMS 150 may be completely oriented longitudinally and parallel to the longitudinal axis or completely oriented transversely and parallel to the lateral axis, but also may be curved or have a combination of curved and linear components. Some or all the channels, in particular the channels of the LMS 150 present in the crotch region 107, may be concave with respect to the longitudinal axis 100, such that they bend towards the longitudinal axis 100. The channels 149, 149' may also be convex, such they bend away from the longitudinal axis 100, or have any other suitable arrangement. The channels 149, 149' may generally align with the channels 126, 126' in the absorbent core, although this disclosure is not so limited. The radius of curvature may typically be at least equal (and may be at least 1.5 or at least 2.0 times this average transverse dimension) to the average transverse dimension of the absorbent layer; and also straight but under an angle of (e.g., from 5°) up to 30°, up to 20°, up to 10° with a line parallel to the longitudinal axis. The radius of curvature may be constant for a channel, or may vary along its length. This may also include channels with an angle therein, provided the angle between two parts of a channel is at least 120°, at least 150°; and in any of these cases, provided the longitudinal extension of the channel is more than the transverse extension. The channels of the LMS 150 may also be branched. For example, a central channel superposed with the longitudinal axis in the crotch region 107 which branches towards the second waist edge 14 and/or towards the first waist edge 13 of the absorbent article. There may be no channel in the LMS 150 that coincides with the longitudinal axis 100 of the absorbent article. When present as symmetrical pairs relative to the longitudinal axis 100, the channels may be spaced apart from one another over their whole longitudinal dimension. The smallest spacing distance may be at least 5 mm, at least 10 mm, or at least 15 mm, for example.

Furthermore, in order to reduce the risk of fluid leakages, the channels of the LMS 150 may therefore be fully encompassed within the LMS 150. The smallest distance between a channel and the closest edge of the LMS 150 may be at least 5 mm.

Figure 19:
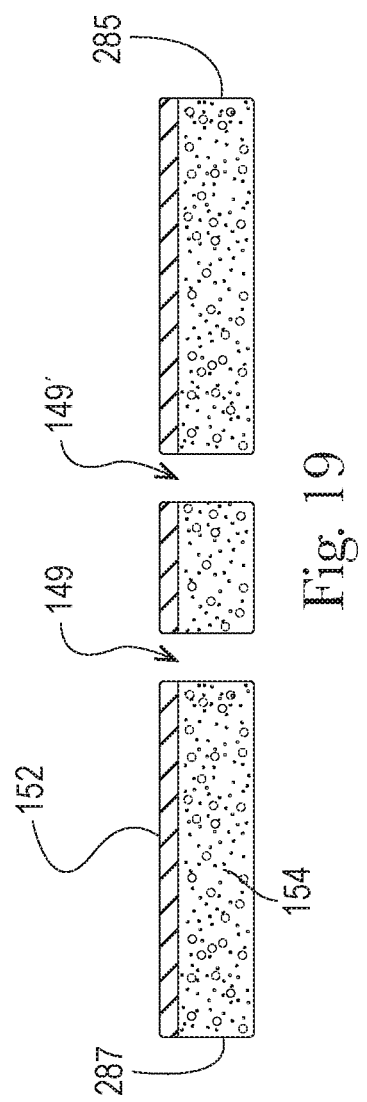
FIG. 19 is a cross-sectional view taken about line 10-10 of the liquid management system of FIG. 18.
Figure 20:
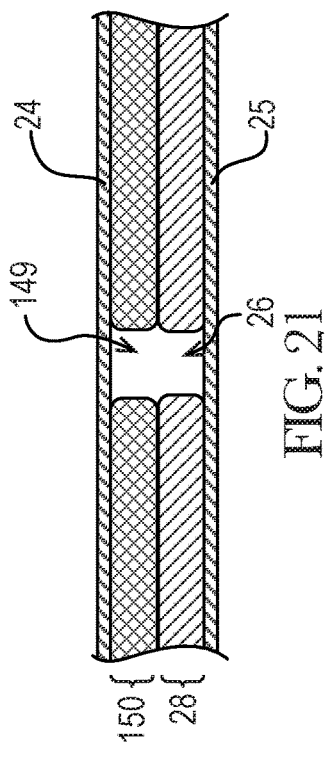
FIGS. 20-35 are partial cross-sectional views of absorbent articles comprising channels in a liquid management system.
Figure 21:
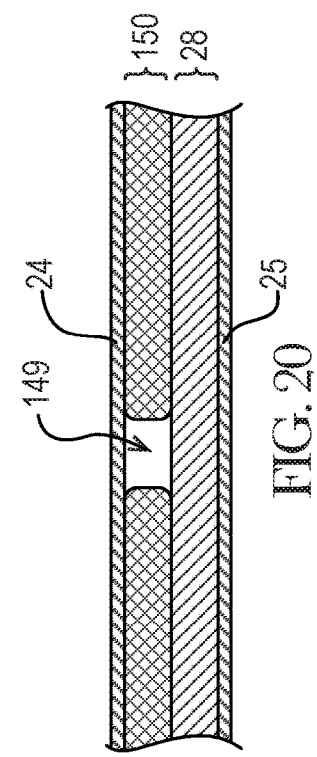

The channels of the LMS 150 may have a width Wc2 along at least part of its length which is at least 2 mm, at least 3 mm, at least 4 mm, up to for example 20 mm, 16 mm, or 12 mm, for example. The width of the channel may be constant through substantially the whole length of the channel or may vary along its length. The channels of the LMS 150 may have similar or different widths Wc2 than the widths Wc1 of channels within the absorbent core 28. As illustrated in FIGS. 19-21, while Wc1 is substantially equal to Wc2, the length of the channels in the absorbent core 28 may exceed the length of the channels in the LMS 150 such that the channels 126, 126' extend closer to the first waist edge 13. However, the channels 149, 149' may extend closer to the waist edge opposite the first waist edge 13.

When the channels within the LMS 150 are formed by material-free zones, the width of the channels (Wc2) is considered to be the width of the material-free zone, disregarding the possible presence of the topsheet 24, or other layers, within the channels. If the channels are formed by zones of reduced basis weight, the width of the channels may be the width of the zones of reduced basis weight.

At least some or all of the channels in the LMS 150 may be permanent channels, meaning their integrity is at least partially maintained both in the dry state and in the wet state. Permanent channels may be obtained by provision of one or more adhesive materials, for example, the fibrous layer of adhesive material or construction glue that helps adhere a substrate with an absorbent material within the walls of the channel. Permanent channels may also be formed by bonding the topsheet 24 to the backsheet 26 together through a channel of the LMS 150. Typically, an adhesive may be used to bond the topsheet 24 and the backsheet 26 through the channels, but it is possible to bond via other known processes, such as pressure bonding, ultrasonic bonding, heat bonding, or combination thereof. The topsheet 24 and the backsheet 26 may be continuously bonded or intermittently bonded along or within portions of or all of the channels. The channels may remain or become visible at least through the topsheet and/or backsheet when the absorbent article is fully loaded with a fluid. Channels of the LMS 150 may align with channels of the absorbent core 28, such that the channels are visible through a garment-facing surface when they contain urine or feces or when a bodily exudate is at least proximate to the channels (such as when a bodily exudate is on the topsheet 24 but not yet within a channel). Such channels may provide a visual indication to a caregiver that the absorbent article should be changed. A graphical indicator or merely a graphic may be printed on an outer surface or other layer of the absorbent article proximate to, over, or partially over the channels to visually obscure the bodily exudates contained within the channels.

An indicator may be included on one or more of the backsheet, a backsheet film, and/or a nonwoven dusting layer, for example, to visually indicate when a change of the absorbent article is required. The indicator may be configured to switch states in the presence of urine and/or feces. The indicator may be, for example, a line or graphic that changes from white or clear to blue. The indicator may also be a word, such a "dry", that disappears once urine is present in the channels. The indicator may be the word "wet" that appears in the presence of urine. Any other suitable indicator or a plurality of indicators may also be utilized.

Referring to FIGS. 12-14, the LMS 150 may comprise at least two channels (e.g., 149, 149'). These channels may be free of, or substantially free of (e.g., less than 10%, less than 5%, less than 3%, less than 2%, or less than 1%), non-woven material or cross-linked cellulose fibers and may be at least partially oriented in the longitudinal direction and/or may be at least partially oriented in the lateral direction. The longitudinal lengths of the channels 149 and 149' about the longitudinal axis 100 may be the same, substantially the same (e.g., within 2 mm or less of each other), or different and the longitudinal lengths of the channels 149 and 149' about the longitudinal axis 100 may be the same, substantially the same, or different. The average lateral width over the longitudinal lengths of the channels 149 and 149' may be the same, substantially the same, or may be different.

The example LMS 150 of the absorbent article of FIG. 12 is shown in isolation in FIGS. 18-19 where FIG. 19 is a cross-sectional view of the LMS 150 taken about line 10-10 of FIG. 18. The LMS 150 may comprises a front side 281, a rear side 283, and two longitudinal sides 285, 287 joining the front side 281 and the rear side 283. The LMS 150 may also comprise a generally planar top side and a generally planar bottom side. The front side 281 of the LMS is the side of the LMS intended to be placed towards the first waist edge 13 of the absorbent article. The LMS 150 may have a longitudinal axis 100" corresponding substantially to the longitudinal axis 100 of the absorbent article, as seen from the top in a planar view as in FIGS. 1 and 18. The LMS 150 may comprise one or more layers. As illustrated, the LMS 150 may comprise a distribution layer 154 and an acquisition layer 152 which cooperate to define the channels 149, 149'. Alternately, less than all of the layers of the LMS 150 may define the channel such that at least one layer of the LMS 150 is continuous while another layer of the LMS 150 is discontinuous.

The LMS 150 may comprise a wrap or bag that is similar to the core wrap described above that is configured to hold particulates. In one example, the wrap may contain Functional Absorbent Materials ("FAM's") that generally function as a wicking/acquisition material. The FAM may comprise an open-celled foam, in the form of a coherent web or sheet or in particulate form, prepared from High Internal Phase Emulsions (hereinafter referred to as "HIPEs"), as illustrated in (U.S. Pat. No. 5,331,015 (DesMarais et al.)

issued Jul. 19, 1994, U.S. Pat. No. 5,260,345 (DesMarais et al.) issued Nov. 9, 1993, U.S. Pat. No. 5,268,224 (DesMarais et al.) issued Dec. 7, 1993, U.S. Pat. No. 5,632,737 (Stone et al.) issued May 27, 1997, U.S. Pat. No. 5,387,207 (Dyer et al.) issued Feb. 7, 1995, U.S. Pat. No. 5,786,395 (Stone et al.) Jul. 28, 1998, U.S. Pat. No. 5,795,921 (Dyer et al.) issued Aug. 18, 1998), (U.S. Pat. No. 5,770,634 (Dyer et al.) issued Jun. 23, 1998, U.S. Pat. No. 5,753,359 (Dyer et al.) issued May 19, 1998, and U.S. Pat. No. 5,633,291 (Dyer et al.) issued May 27, 1997), (Bhumgara, Z. Filtration & Separation 1995, March, 245-251; Walsh et al. J. Aerosol Sci. 1996, 27, 5629-5630; published PCT application W/O 97/37745, published on Oct. 16, 1997, in the name of Shell Oil Co.).

While portions of the channels 126, 126' of the absorbent core 28 and the channels 149, 149' of the LMS 150 shown in FIGS. 12-14 are generally aligned, this disclosure is not so limited. In fact, as is to be appreciated, particular arrangements of the channels in an LMS 150 and/or an absorbent core 28 may vary. FIGS. 20-35 are simplified partial cross-sectional views of example absorbent articles that illustrate example configurations of the topsheet 24, the backsheet 26, the LMS 150 and the absorbent core 28. While FIGS. 20-35 illustrate a wide variety of channel arrangements, such arrangements are merely example arrangements and are not to be limiting, as a number of other channel arrangements are within the scope of the present disclosure. Further, various aspects of some of the figures may be incorporated into the arrangements of other figures without departing from the scope of the present disclosure.

Referring first to FIG. 20, an example channel arrangement is illustrated in which the LMS 150 defines a channel 149 and the absorbent core 28 does not define any channels. It is noted that while the LMS 150 is illustrated as a single-layer system in FIG. 20, among other figures, other articles may comprise a multi-layer LMS without departing from the scope of this disclosure.

Figure 28:
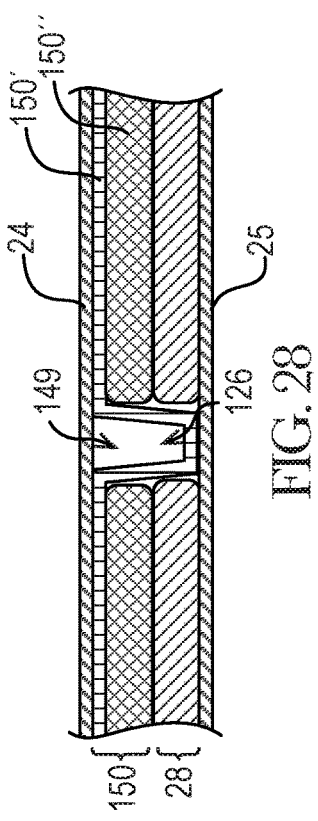

FIG. 21 illustrates another example channel arrangement in which the channel 149 of the LMS 150 is generally aligned with the channel 126 of the absorbent core 28. While the channel 149 and the channel 126 are illustrated as having similar widths, the widths of the two channels may differ. For example, the width of the channel 149 may be wider or narrower than the width of the channel 126 along the entire aligned portion in the longitudinal direction. The width of at least one of the channel 149 and the channel 126 may vary along the longitudinal direction, such that at some points along the overlapping portion, the channel 149 and the channel 126 have similar widths (as shown in FIG. 28), while at other points along the overlapping portion, the channels have different widths. For example, the channel 149 may have the same width along its entire longitudinal length while the channel 126 may have portions that are tapered or flared, or vice versa. The channel 149, or at least portions of the channel 149, of the LMS 150 may not overlap the channel 126 of the absorbent core 28. In such cases, the channel width of the channel 149 may be the same or different as the channel width of the channel 126. Additionally, the relative similarities or differences of the channel widths may vary along respective longitudinal lengths of the channels 149, 126.

Figure 22:
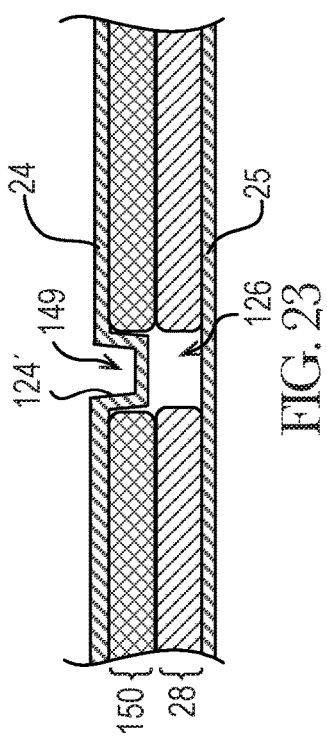

FIG. 22 illustrates an article in which a portion of the topsheet 24 is recessed into the channel 149 defined by the LMS 150 and the channel 126 defined by the absorbent core 28. The topsheet 24 may be intermittently or continually bonded to the backsheet 26 along the channel to form a recess or groove that is visible from the wearer-facing side of the absorbent article. An adhesive may be used to bond the topsheet 24 and the backsheet 26 through the channels, although other known processes may be used to form the bond, such as pressure bonding, ultrasonic bonding, heat bonding, or combinations thereof.

Figure 23:
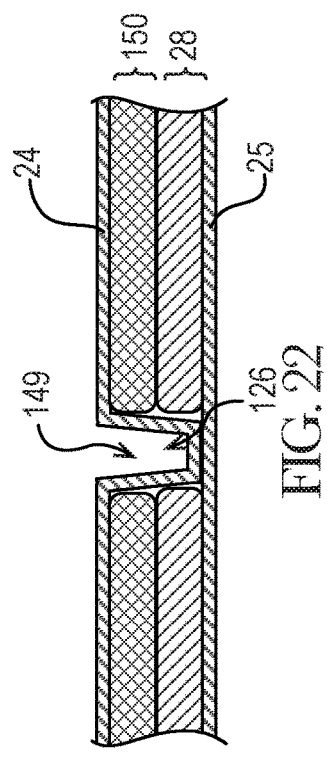

FIG. 23 illustrates an article in which the topsheet 24 comprises a contoured element 24' that generally aligns with the channel 149 defined by the LMS 150. The contoured element 24' may be any suitable three-dimensional structure, such as a groove, ridge, or other element formed into the topsheet 24. The contoured element 24' of the topsheet 24 may have a different thickness or basis weight than other regions of the topsheet 24. Other layers of the absorbent article, such as the LMS 150 and/or the absorbent core 28 additionally or alternatively may comprise a three-dimensional structure generally aligned with a channel in the absorbent article. By way of comparison to FIG. 22, for example, the contoured element 24' of FIG. 23 does not necessarily have to be bonded to backsheet 26 to maintain its relative placement within the channel 149. The contoured element 24' may be deeper than the illustrated example such that it is recessed into both the channel 149 and the channel 126. Both the topsheet 24 and the backsheet 26 may include countered elements that are recessed into channel 126 and channel 149 of the LMS 150 and the absorbent core 28, respectively.

Figure 24:
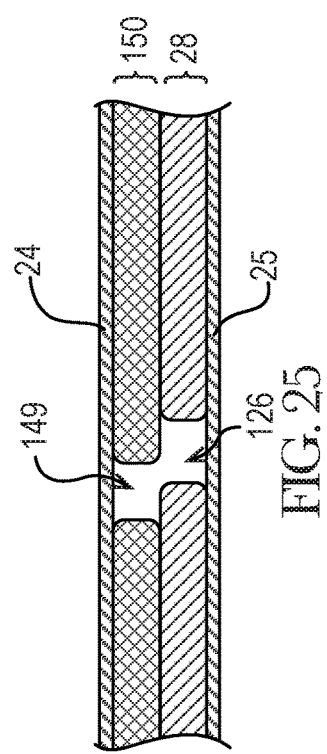

FIG. 24 illustrates an article in which both the topsheet 24 and the backsheet 26 are recessed into channels defined by the LMS 150 and the absorbent core 28, respectively. Similar to the article illustrated in FIG. 22, the topsheet 24 may be intermittently or continually bonded to the backsheet 26 along the channel. Any suitable technique or combination of techniques may be used to bond the topsheet 24 and the backsheet 26. Furthermore, while the topsheet 24 and backsheet 26 may be bonded proximate to the interface between the LMS 150 and the absorbent core 28, this disclosure is not so limited. In other words, the topsheet 24 may be recessed further into the channels than the backsheet 26 or the backsheet 26 may be recessed further into the channels than the topsheet 24.

Figure 25:
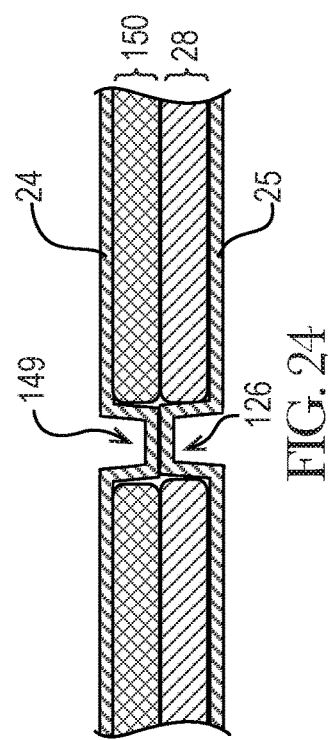
Figure 26:
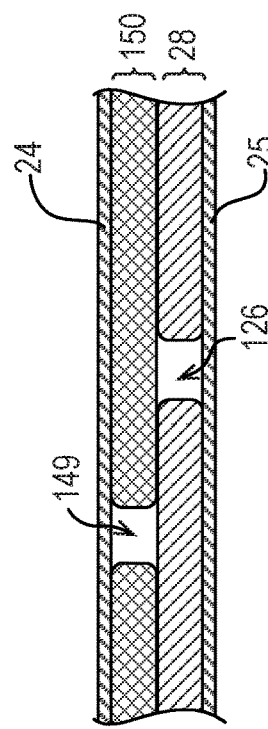
Figure 27:
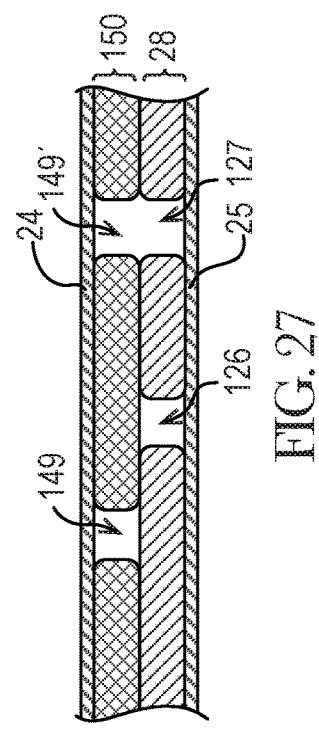

FIG. 25 illustrates an article in which the channel 149 and the channel 126 are only partially aligned. Only a portion of the channel 149 may overlap with a portion of the channel 126. Such partially overlapping arrangement may continue along the longitudinal direction. Alternatively, the channels 149 and the channel 126 may become vertically aligned along the longitudinal direction or the channels may laterally deviate in direction such that there is no overlapping portion. An example configuration in which there is no overlapping portion between the channel 149 and the channel 126 is illustrated in FIG. 26. FIG. 27 illustrates yet another article in which each of the LMS 150 and the absorbent core 28 defines two channels, 149, 149',126, 127. As illustrated, channel 149 and channel 126 do not overlap with any other channels, while channel 149' of the LMS 150 overlaps, and in this case is completely aligned, with channel 127.

Figure 29:
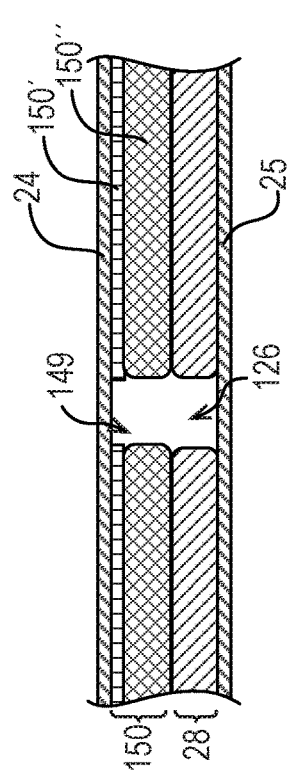

FIG. 28 illustrates an article with a multi-layer LMS 150 having a first layer 150' and a second layer 150". The first layer 150' may comprise a nonwoven material and the second layer 150" comprises cross-linked cellulose fibers. In the illustrated arrangement, the absorbent core 28 defines a channel 126 and various layers of the LMS 150 collectively define a channel 149. The first layer 150' is recessed into both the channel 149 and the channel 126 and bonded to the backsheet 26 thereby forming a void between the first layer 150' and the topsheet 24. FIG. 29 illustrates another article with an LMS 150 having a first layer 150' and a second layer 150″. In the illustrated arrangement, the absorbent core 28 defines a channel 126 and an absence of both the first layer 150′ and the second layer 150″ LMS 150 defines a channel 149. One or more layers of the LMS 150 may not be recessed into the channel 149, or one or more layers of the LMS 150 may be recessed into the channel 149, but not into the channel 126.

Figure 30:
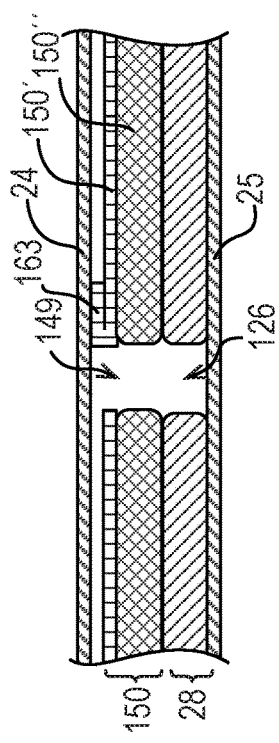

FIG. 30 illustrates an article of a multi-layer LMS 150 in which the first layer 150′ is cut and folded along the channel 149 to form a flap 163 that extends along the longitudinal direction of the channel 149. The flap 163 may be sandwiched between the first layer 150′ and the topsheet 24 during the manufacturing of the absorbent article. Alternatively, the flap 163 may be folded downward toward the backsheet 26 such that it is received by the channel 149 and positioned along its wall. Flaps may be present on either lateral side of the channel 149 which may be formed by slicing the first layer 150′ along the longitudinal centerline of the channel 149 and then folding the flap to expose the channel.

Figure 31:
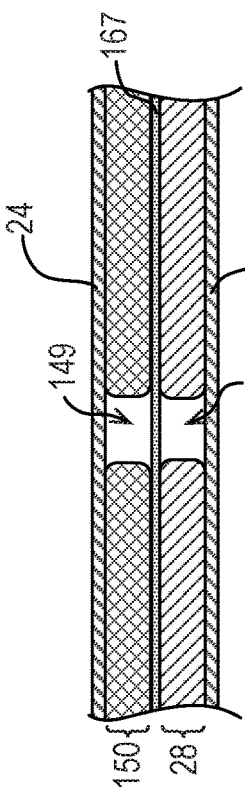
Figure 32:
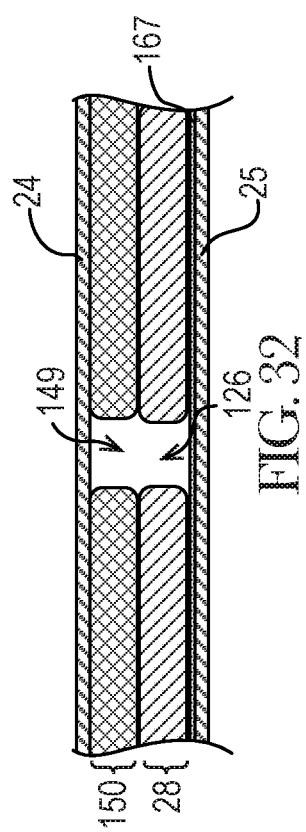

It may be desirable to provide a visual indication of the channels. Such visual indication may be provided using any suitable technique. FIG. 31 illustrates an article comprising a visually distinct layer 167. The visually distinct layer 167 may be a layer on the garment-facing side of the LMS 150 that includes a pattern, image, color and/or tint that is different than that of other layers in the LMS 150. The visually distinct layer 167 is visible through at least one of the topsheet 24 and the backsheet 26 to provide an increased visual distinctiveness of the channel 149. The increased visual distinctiveness may serve as an internal serviceable indicia to facilitate more accurate alignment of the absorbent article on the wearer during the application process. FIG. 32 illustrates another article having the visually distinct layer 167. In the illustrated article, the visually distinct layer 167 is positioned between the absorbent core 28 and the backsheet 26. The visually distinct layer 167 may also be provided at other locations within the absorbent article.

Figure 33:
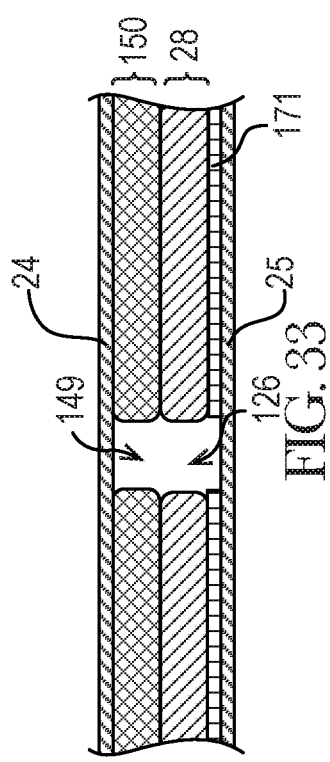
Figure 34:
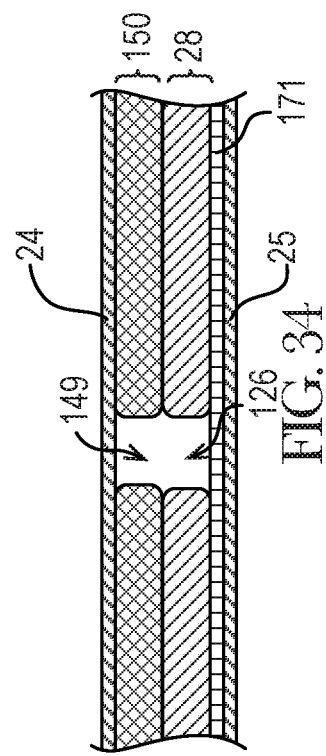
Figure 35:
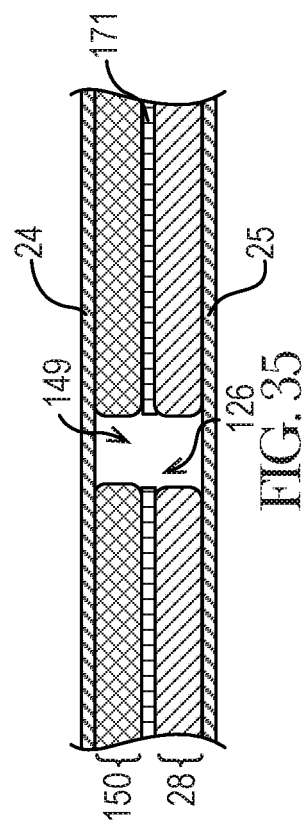

In addition to the LMS 150 and the absorbent core 28, it may be desirable to include additional layers in the absorbent article, such as a liquid distribution layer. FIGS. 33-35 illustrate articles comprising a liquid distribution layer 171 that comprises a liquid distribution material. The liquid distribution material may be a fibrous or foamed material, for example. The liquid distribution layer 171 may be discontinuous, as shown in FIGS. 33 and 35, or may be continuous, as shown in FIG. 34. Thus, the liquid distribution layer 171 may help to define a channel within the absorbent article or may span a channel defined by the LMS 150 and/or the absorbent core 28. Furthermore, the liquid distribution layer 171 may be positioned at any suitable layer of the absorbent article to achieve the desired liquid distribution. As shown in FIGS. 33 and 34, for example, the liquid distribution layer 171 is positioned between the absorbent core 28 and the backsheet 26. By comparison, in FIG. 35, the liquid distribution layer 171 is positioned between the LMS 150 and the absorbent core 28. A liquid distribution layer may be positioned between the topsheet 24 and the LMS 150. Some articles may have a plurality of liquid distribution layers.

Figure 4:
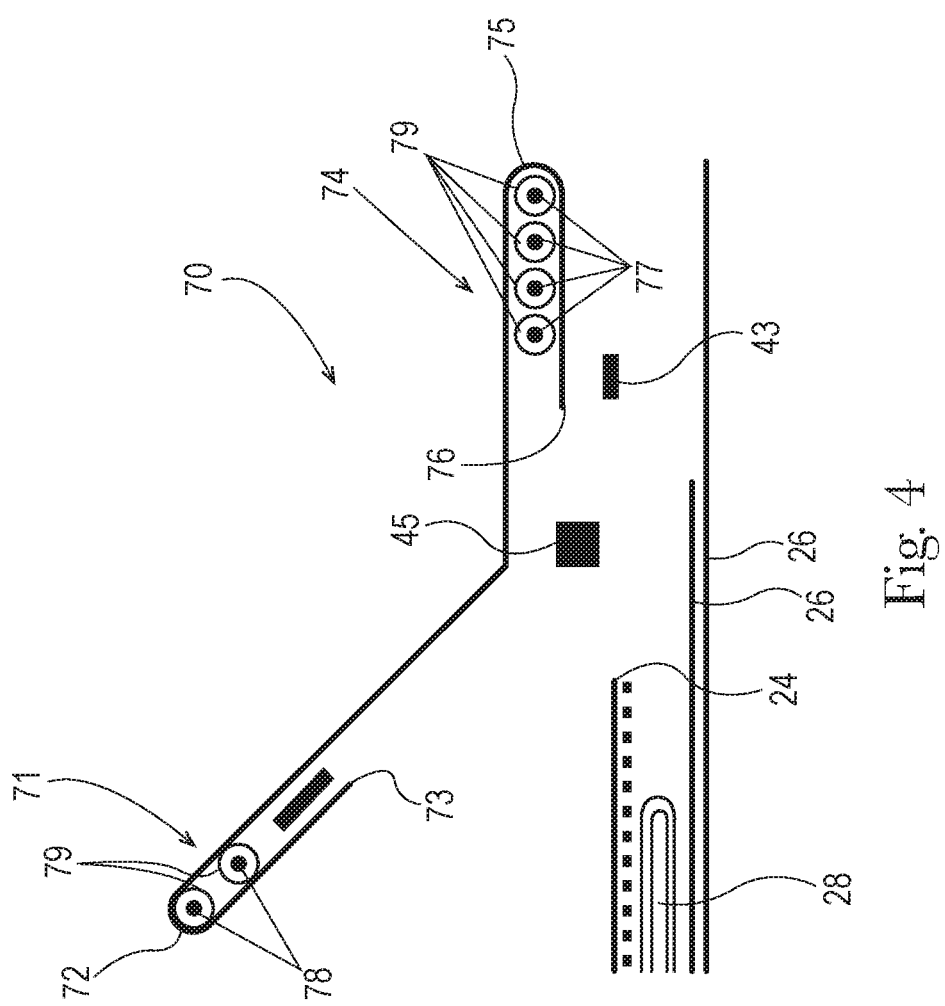
FIG. 4 is a schematic cross sectional view of the absorbent article of FIG. 1, the cross section taken along the line A-A.
Figure 5:
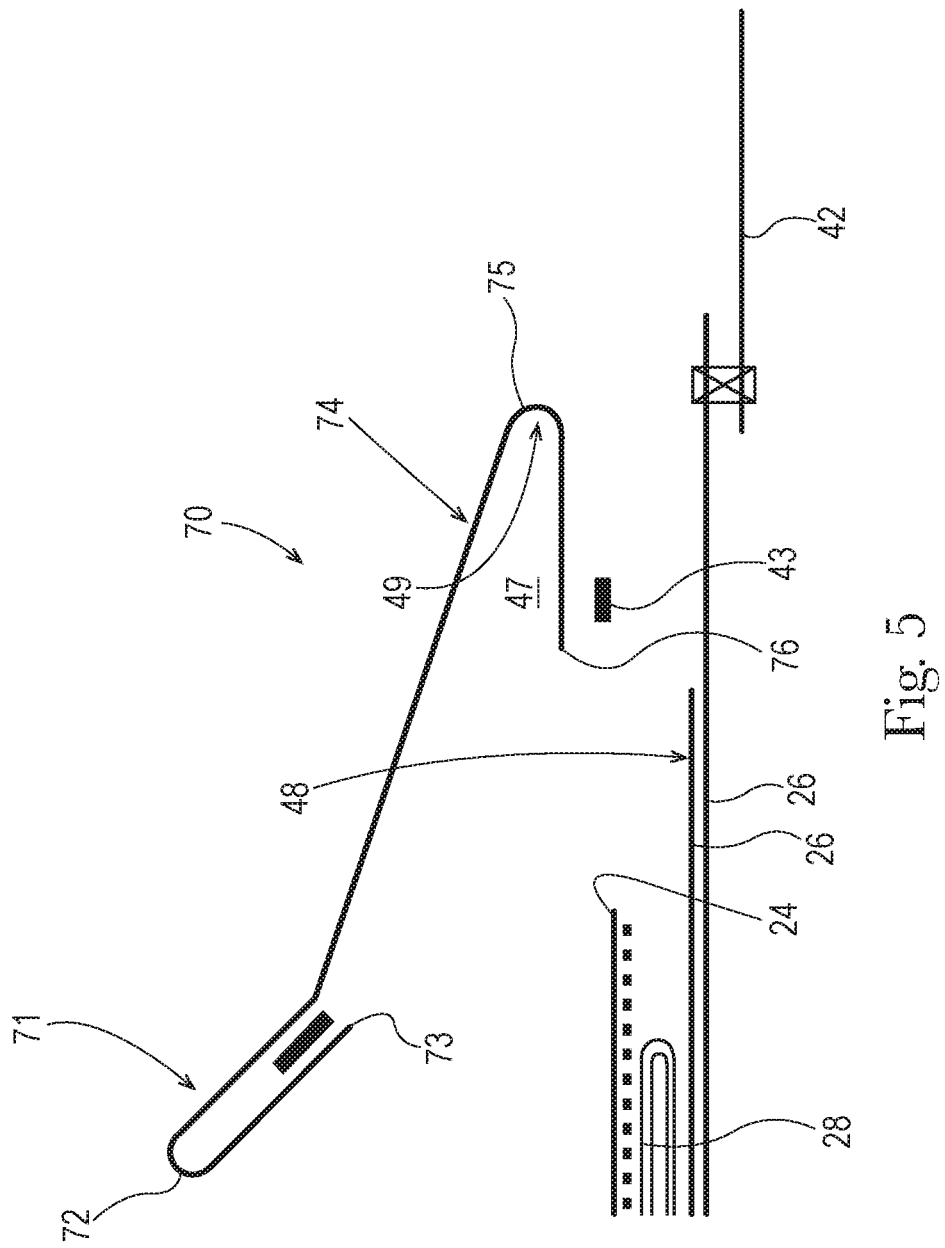
FIG. 5 is a schematic cross sectional view of the absorbent article of FIG. 1, the cross section taken along the line B-B.
Figure 6:
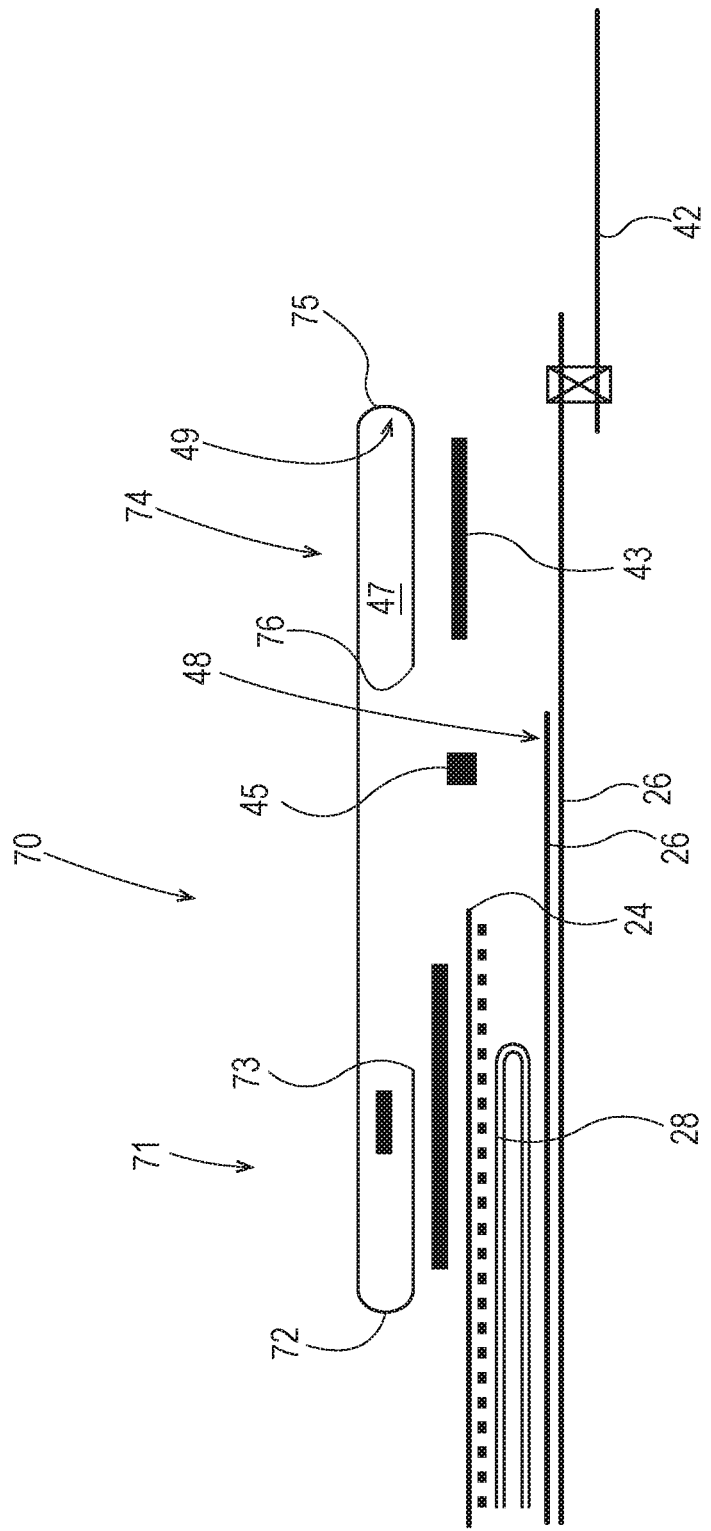
FIG. 6 is a schematic cross sectional view of the absorbent article of FIG. 1, the cross section taken along the line C-C.
Figure 7:
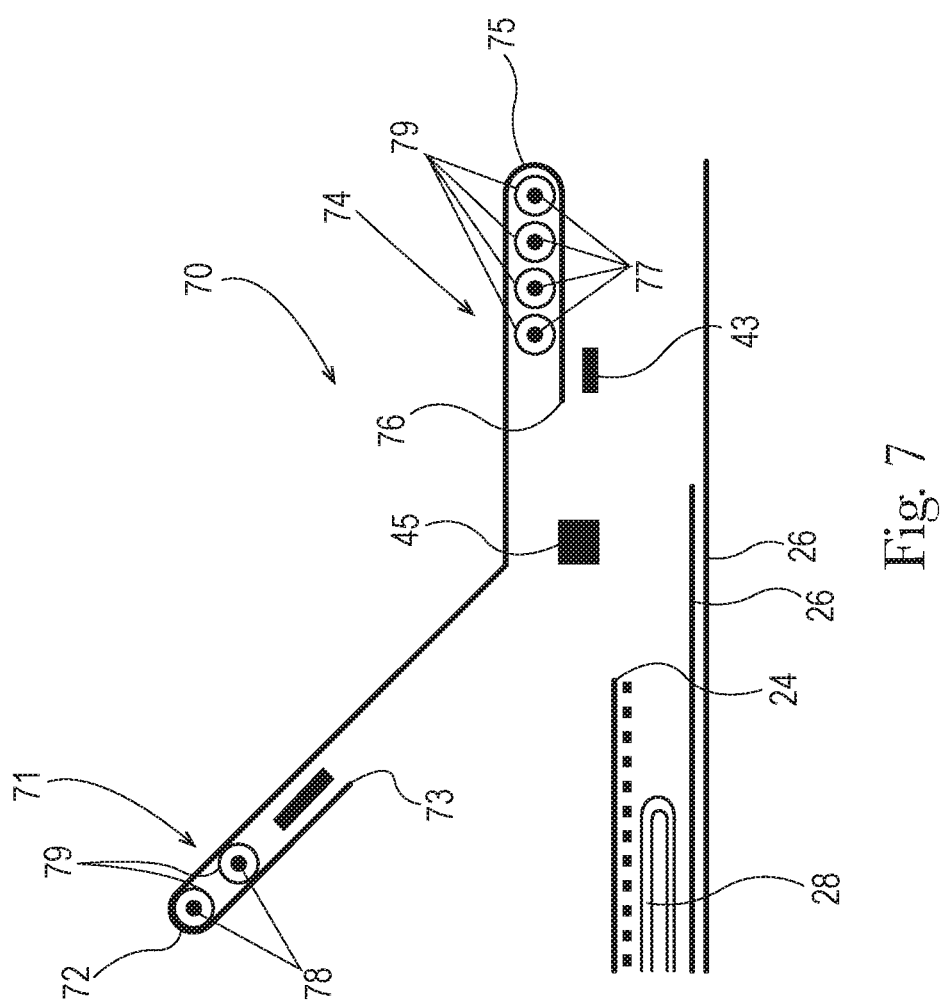
FIG. 7 is a schematic cross sectional view of the absorbent article of FIG. 1 with an opacity strengthening patch, the cross section taken along the line A-A.
Figure 8:
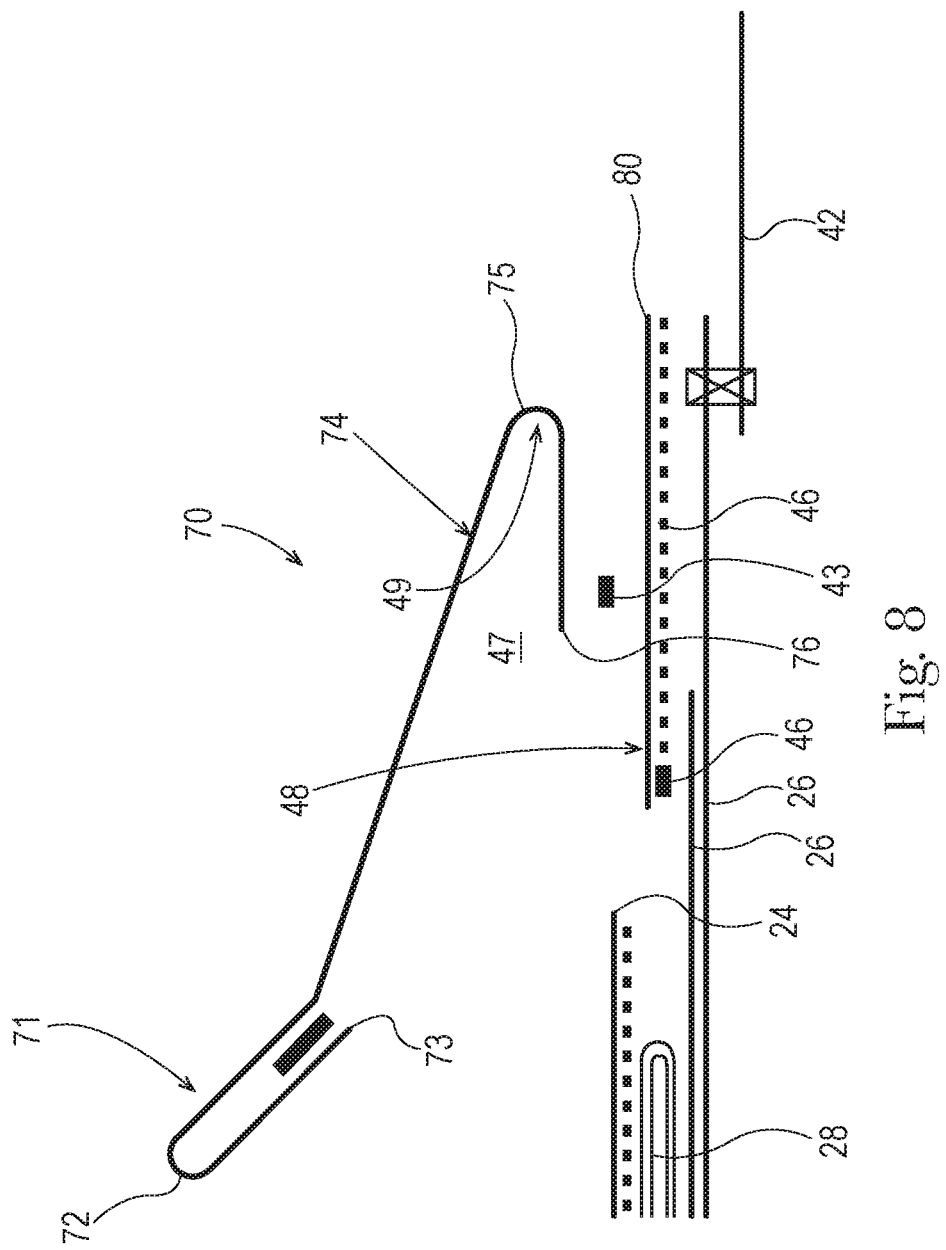
FIG. 8 is a schematic cross sectional view of the absorbent article of FIG. 1 with an opacity strengthening patch, the cross section taken along the line B-B.
Figure 9:
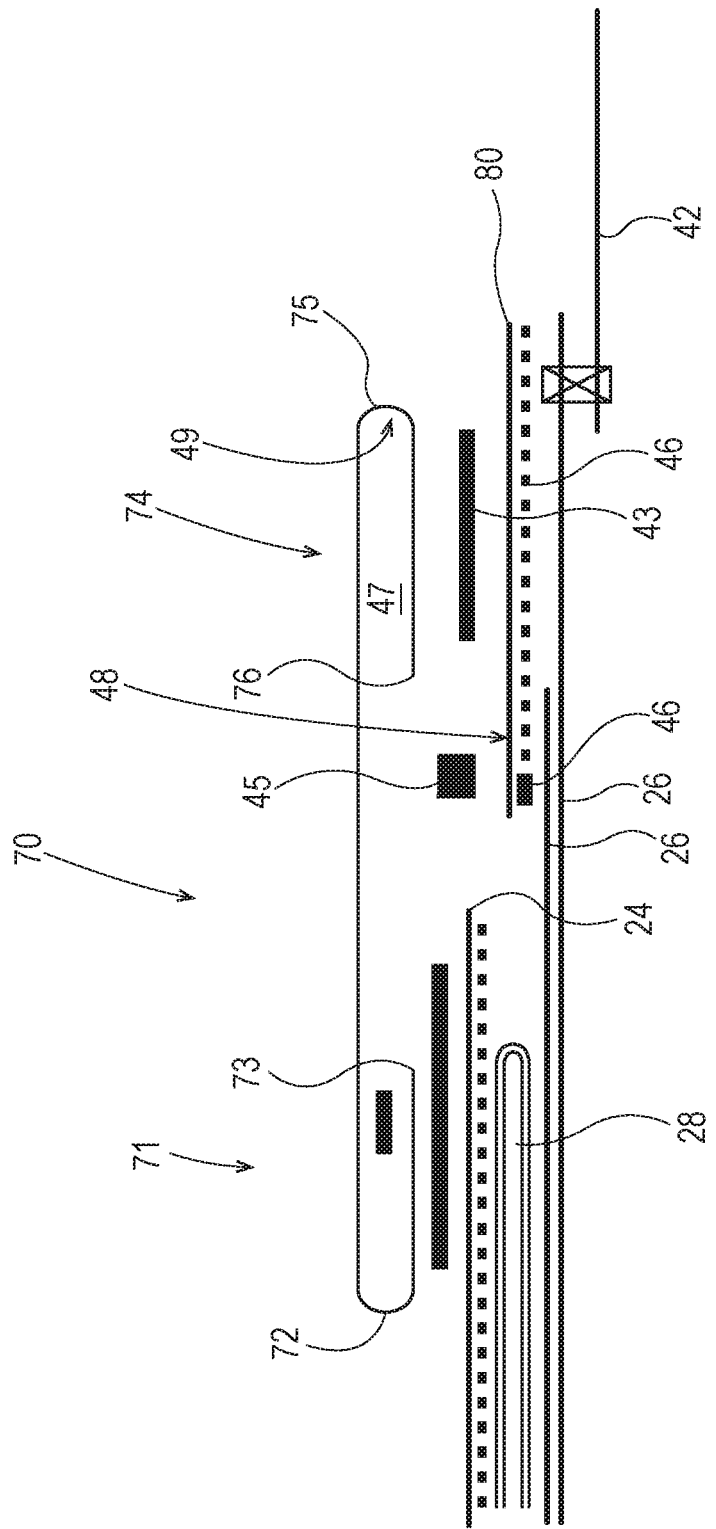
FIG. 9 is a schematic cross sectional view of the absorbent article of FIG. 1 with an opacity strengthening patch, the cross section taken along the line C-C.

Leg Gasketing System:

The absorbent article 20 may include a leg gasketing system 70 that is attached to the chassis 22. FIGS. 2 and 3 depict schematic cross sectional views of the leg gasketing systems of FIG. 1 in a flat, uncontracted state, the views taken through the lateral centerline 110 (FIG. 2 is a schematic cross section of the left leg gasketing system, and FIG. 3 is a schematic cross section of both leg gasketing systems in relation to the topsheet). FIGS. 4-9 also depict schematic cross sectional views of the leg gasketing system 70 of FIG. 1. FIGS. 4-6 are cross sections of the disposable absorbent article of FIG. 1 without an opacity strengthening patch 80, and FIGS. 7-9 are cross sections of the disposable absorbent article of FIG. 1 with an opacity strengthening patch 80. In the absorbent articles of FIGS. 7-9, the opacity strengthening patches 80 are located in the four corners of the diaper chassis 22, overlapping portions of both the polymeric film inner layer of the backsheet 26 and the ears 40, 42. FIGS. 4 and 7 are schematic cross sectional views through line A-A of FIG. 1. FIGS. 5 and 8 are schematic cross sectional views through line B-B of FIG. 1. FIGS. 6 and 9 are schematic cross sectional views through line C-C of FIG. 1. The leg gasketing system 70 may include an inner cuff 71 that has an inner cuff folded edge 72 and an inner cuff material edge 73. The leg gasketing system 70 may further include an outer cuff 74 that has an outer cuff folded edge 75 and an outer cuff material edge 76.

Each leg gasketing system 70 may comprise a single, continuous web of material. A leg gasketing system having a single web of material may provide a cost advantage over leg gasketing systems having more than one web of material. Further, a leg gasketing system formed from one web of material may have fewer leaks, as there are no holes created by bonding more than one web of material. Also, a leg gasketing system having one web of material may be more aesthetically pleasing, as few mechanical bonds are visible. The leg gasketing system 70 may be formed from more than one web of material (e.g., multiple webs of material that are joined together to become one web of material, or multiple distinct webs of material that are separate from the disposable absorbent article chassis and form part of the leg gasketing system). Herein, locations (e.g., folded edge, material edge, etc.) on the leg gasketing system 70 are detailed in reference to "a web of material" or "a portion of the web of material." The recitations of "a web of material" or "the web of material" refer to leg gasketing systems that may be formed from a single, continuous web of material, multiple webs of material that are joined together to become one web of material, or multiple distinct webs of material that are separate from the disposable absorbent article chassis and form part of the leg gasketing system. All such leg gasketing systems are contemplated.

The leg gasketing system 70 may include an inner cuff 71 that has an inner cuff folded edge 72 and an inner cuff material edge 73. The leg gasketing system 70 may further include an outer cuff 74 that has an outer cuff folded edge 75 and an outer cuff material edge 76. The web of material may be folded laterally inward (toward the longitudinal centerline 100 of the absorbent article 20) to form the outer cuff folded edge 75 and folded laterally outward (away from the longitudinal centerline 100 of the absorbent article 20) to form the inner cuff folded edge 72.

At least a portion of the web of material between the outer cuff folded edge 75 and the outer cuff material edge 76 may be attached to the chassis 22 (e.g., the topsheet 24, the backsheet 26, and/or the opacity strengthening patch 80) in the first waist region 36, the second waist region 38 and the crotch region 37. The attachment to the chassis 22 is made through utilization of one or more cuff attachment bonds 43. One or more of the cuff attachment bonds 43 may be continuous, or substantially continuous (e.g., in a continuously intermittent pattern) from the first waist edge 13 to the second waist edge 14. As seen in FIGS. 3-6, a cuff attachment bond 43 may attach at least a portion of the web of material between the outer cuff folded edge 75 and the outer cuff material edge 76 to the backsheet 26 (inner or outer backsheet layer). Further, in FIGS. 3-6, a single cuff attachment bond 43 is shown, but absorbent articles having multiple cuff attachment bonds 43 are contemplated. As seen in FIGS. 7-9, a cuff attachment bond 43 may attach at least a portion of the web of material between the outer cuff folded edge 75 and the outer cuff material edge 76 to the opacity strengthening patch 80 in a portion of the first waist region 36 and a portion of the second waist region 38. The opacity strengthening patch is attached to the inner layer of backsheet 26 (e.g., backsheet film) by at least one OSP bond(s) 46. In the crotch region 37 and in a portion of the first waist region 36 and in a portion of the second waist region 38, at least a portion of the web of material between the outer cuff folded edge 75 and the outer cuff material edge 76 is attached to the backsheet 26 (inner or outer backsheet layer) through the cuff attachment bond 43. In other words, from first waist edge 13 to second waist edge 14, at least a portion of the web of material between the outer cuff folded edge 75 and the outer cuff material edge 76 is attached to either the backsheet 26 or to the opacity strengthening patch 80 through at least one continuous or substantially continuous cuff attachment bond 43. In FIGS. 7-9, a single cuff attachment bond 43 is shown, but absorbent articles having multiple cuff attachment bonds 43 are contemplated. The cuff attachment bonds 43 and the OSP bonds 46 may take the form of glue, heat bond, pressure bond, CPW bonds, or any other bonding method known in the art. In the absorbent articles of FIGS. 3-9, the cuff attachment bonds 43 and the OSP bonds 46 take the form of a glue bond.

Further, at least a portion of the web material between the inner cuff folded edge 72 and the outer cuff folded edge 75 is attached to the chassis 22 in at least the crotch region 37 and the first waist region 36. The attachment of the web of material between the inner cuff folded edge 72 and the outer cuff folded edge 75 to the chassis 22 in at least the crotch region 37 and the first waist region 36 is made through utilization of one or more cuff separation bonds 45. As seen in FIGS. 1-6, the cuff separation bond 45 attaches at least a portion of the web material between the inner cuff folded edge 72 and the outer cuff folded edge 75 to the inner layer of the backsheet 26 in the crotch region 37, the first waist region 36, and a portion of the second waist region 38. As seen in FIGS. 1-3 and 7-9, the cuff separation bond 45 attaches at least a portion of the web of material between the outer cuff folded edge 75 and the inner cuff folded edge 72 to the opacity strengthening patch 80 in a portion of the first waist region 36 and a portion of the second waist region 38. The opacity strengthening patch is attached to the inner layer of backsheet 26 (e.g., backsheet film) by at least one OSP bond(s) 46. In the crotch region 37 and in a portion of the first waist region 36 and in a portion of the second waist region 38, at least a portion of the web of material between the outer cuff folded edge 75 and the inner cuff folded edge 72 is attached to the backsheet 26 (inner or outer backsheet layer). In other words, from first waist edge 13 to second waist edge 14, at least a portion of the web of material between the outer cuff folded edge 75 and the inner cuff folded edge 72 is attached to either the backsheet 26 or to the opacity strengthening patch 80 except in the area where an opening 51 to the leg gasketing system pocket 47 is located. The cuff separation bond 45 may take the form of glue, heat bond, pressure bond, CPW bonds, or any other bonding method known in the art. In the absorbent articles of FIGS. 3-9, the cuff separation bond 45 takes the form of a glue bond.

As illustrated in FIGS. 1 and 4-9, the web of material between the inner cuff folded edge 72 and the outer cuff folded edge 75 is unattached to the chassis 22 in at least a portion of the second waist region 38. Due to the web of material between the inner cuff folded edge 72 and the outer cuff folded edge 75 being unattached to the chassis 22 in at least a portion of the second waist region 38, a leg gasketing system pocket 47 is formed in at least a portion of the second waist region of the leg gasketing system 70. The leg gasketing system pocket 47 includes an inboard longitudinal edge 48 and an outboard longitudinal edge 49, which define lateral dimensions of the leg gasketing system pocket. The inboard longitudinal edge 48 of the leg gasketing system pocket 47 may be coterminous with a line that the cuff separation bond 45 runs along in the longitudinal direction. The outboard longitudinal edge 49 may be coterminous with the outer cuff folded edge 75. The outboard longitudinal edge 49 may be coterminous with the most outboard bond of the outer cuff 74.

The leg gasketing system pocket 47 may include an opening 51 which runs a distance along the inboard longitudinal edge 48 of the leg gasketing system pocket 47. The opening 51 is created by a break in the cuff separation bond 45. Referring to FIG. 1, the cuff separation bond 45 runs in the longitudinal direction of the absorbent article, and is continuous, or substantially continuous (e.g., in a continuously intermittent pattern) in the first waist region 36 and the crotch region 37. The continuous cuff separation bond 45 continues into the second waist region 38, but then stops for a defined distance and then starts again along the same longitudinal line. The distance in which the cuff separation bond 45 stops along that longitudinal line is the distance in which the web material between the inner cuff folded edge 72 and the outer cuff folded edge 75 is unattached to the chassis 22 (either backsheet 26 or opacity strengthening patch 80, depending on the particular location). Accordingly, this distance is the length of the opening 51 which runs along the inboard longitudinal edge 48 of the leg gasketing system pocket 47. The opening 51 has an inboard lateral edge 52 and an outboard lateral edge 53 where the cuff separation bond 45 starts and stops along the longitudinal line that the cuff separation bond 45 runs along. As illustrated in FIG. 1, the length of the opening 51 can be determined by measuring the distance between inboard lateral edge 52 and outboard lateral edge 53, taken along the longitudinal line that the cuff separation bond 45 runs along.

The leg gasketing system pocket 47 may include an opening 51 which again runs a distance along the inboard longitudinal edge 48 of the leg gasketing system pocket 47. The opening 51 is created by a series of breaks in the cuff separation bond 45. Referring to FIG. 1, the cuff separation bond 45 runs in the longitudinal direction of the absorbent article, and is continuous in the first waist region 36 and the crotch region 37. The continuous cuff separation bond 45 continues into the second waist region 38, but then becomes an intermittent bond pattern (e.g., stop-start-stop-start) for a defined distance and then becomes continuous again along the same longitudinal line. The distance in which the cuff separation bond 45 becomes an intermittent bond pattern along that longitudinal line is the distance in which the web material between the inner cuff folded edge 72 and the outer cuff folded edge 75 is intermittently attached to the chassis 22. This intermittent pattern for a distance of the cuff separation bond 45 creates series of small pockets, together referred to herein as a leg gasketing system pocket.

The pocket and opening can occur in the first waist region, the second waist region, or in the crotch region as needed for the specific type of exudates and the particular situation where leakage prevention is desired. For instance, a wearer who sleeps on their belly (front) may benefit from the pocket and opening being located in the front waist region, as to stop urine leakage out of the front waist during sleep. Likewise, it may be important to create the opening on the crotch region for users wearing the article in the standing position as to contain exudates that are likely to locate centrally in the article due to the force of gravity when in a standing position.

The opening 51 may measure between about 5 mm and about 100 mm in the longitudinal direction, or any range or distance within the range of about 5 mm to about 100 mm; the opening may measure about 75 mm or about 50 mm; and the opening may measure between about 1 mm and about 20 mm. The length of opening 51 may be between about 1% and about 75% of the overall longitudinal length of the leg gasketing system pocket 47 (or any range or percentage within the range of about 1% to about 75%). The overall longitudinal length of the leg gasketing system pocket 47 is the distance from the furthest longitudinally inboard portion of the pocket to the furthest longitudinally outboard portion of the pocket. For the absorbent article shown in FIG. 1, the overall longitudinal length of the leg gasketing system pocket 47 is the distance from the inboard lateral edge 52 of the opening 51 to the second waist edge 14 of the absorbent article 20, taken along the longitudinal line that the cuff separation bond 45 runs along. In other words, for the absorbent article shown in FIG. 1, the longitudinal dimensions of the leg gasketing system pocket 47 are defined by the inboard lateral edge 52 of the opening 51 and the second waist edge 14. The overall longitudinal length of the leg gasketing system pocket 47 may measure between about 5 mm and about 200 mm in the longitudinal direction, or any range or distance within the range of about 5 mm to about 200 mm; about 100 mm, about 75 mm, or about 50 mm; and the overall longitudinal length may measure between about 1 mm and about 20 mm.

The overall lateral width of the leg gasketing system pocket 47 is the distance from the furthest laterally inboard portion of the pocket to the furthest laterally outboard portion of the pocket. For the absorbent article shown in FIG. 1, the overall lateral width of the leg gasketing system pocket 47 is the distance from the inboard longitudinal edge 48 of the leg gasketing system pocket to the outboard longitudinal edge 49 of the leg gasketing system pocket, taken along a line that is parallel to the second waist edge 14 and centered in the middle of the opening 51 of the leg gasketing system pocket. In other words, for the absorbent article shown in FIG. 1, the lateral dimension of the leg gasketing system pocket 47 (i.e., the width) is defined by inboard and outboard longitudinal edges 48, 49 of the leg gasketing system pocket 47. The overall lateral width of the leg gasketing system pocket 47 may measure between about 5 mm and about 60 mm in the lateral direction, or any range or distance within the range of about 5 mm to about 60 mm; or about 30 mm, about 25 mm, or about 20 mm; and the overall lateral width measures between about 1 mm and about 20 mm. The overall lateral width of the leg gasketing system pocket 47 may be between about 1% and about 75% of the overall longitudinal length of the leg gasketing system pocket 47 (or any range or percentage within the range of about 1% to about 75%). The length of opening 51 may be between about 20% and about 100% of the overall lateral width of the leg gasketing system pocket 47 (or any range or percentage within the range of about 20% to about 100%).

When a wearer of an absorbent article has a runny bowel movement, many times the runny bowel movement spreads upon defecation and leaks out of the absorbent article in an area between the leg cuffs and wearer's legs, or in an area between the waist region and the wearer's back. Leaks of this type often happen because the snug fit between user's body and the attached absorbent article do not allow enough room for the runny bowel movement to remain contained within the absorbent article during the wearer's movement. One advantage of the leg gasketing system pocket 47 as detailed herein, in combination with the leg gasketing system(s) as detailed herein, are the additional pocketed areas that provide extra void volumes within the leg cuffs for containment of bodily extrudate (e.g., fecal material). When the wearer moves, a portion of the bodily extrudate will migrate into the leg gasketing system pocket 47 for containment and be held/trapped between two layers of nonwoven within the leg gasketing system before it can leak out in an area between the wearer's back and the back waist region of the absorbent article or an area between the leg cuffs and wearer's legs of the absorbent article. Thus, the leg gasketing system pocket 47 detailed herein reduces leaks. Moreover, leg gasketing system pocket 47 provides additional void volume within the leg cuffs to receive the fecal material which helps in isolating the fecal material from wearer's skin, and restricts the flow towards the front by the separate sheet.

The leg gasketing system pocket 47 may be free of elastic members 77. The leg gasketing system pocket 47 may contain one or more snap back elastic members. The leg gasketing system pocket 47 may have a second opening 55 along the second waist edge 14 of the absorbent article. The leg gasketing system pocket 47 may be sealed along the second waist edge 14.

At least a portion of the web of material between the outer cuff folded edge 75 and the outer cuff material edge 76 may be attached to the chassis 22 (e.g., topsheet 24, backsheet 26, and/or opacity strengthening patch 80) in the first waist region 36, the second waist region 38 and the crotch region 37; and at least a portion of the web of material between the inner cuff folded edge 72 and the outer cuff folded edge 75 may be attached to the chassis 22 in the crotch region 37 and the first waist region 36; wherein the outer cuff includes an elastics adhesive 79 and at least one longitudinally oriented elastic member running parallel to the outer cuff folded edge 75, the elastics adhesive 79 and at least one elastic member disposed between 1) the web of material between the outer cuff folded edge 75 and the outer cuff material edge 76 and 2) the web of material between the outer cuff folded edge 75 and the inner cuff folded edge 72; wherein in at least a portion of the second waist region, the outer cuff is free of elastics adhesive 79 and elastic members 77, thus forming a leg gasketing system pocket 47 between 1) the web of material between the outer cuff folded edge 75 and the outer cuff material edge 76 and 2) the web of material between the outer cuff folded edge 75 and the inner cuff folded edge 72, the leg gasketing system pocket 47 having an outboard longitudinal edge 49 at the outer cuff folded edge 75; wherein the leg gasketing system pocket 47 comprises an opening 51 on an inboard longitudinal edge 48 of the leg gasketing system pocket.

The pocket 47 may include a thermal or compression bond that defines at least a portion of the perimeter of the pocket (e.g., the entire perimeter of the pocket), such that the at least a portion of the pocket 47 (e.g., the entire pocket), can be made visible to a wearer or caregiver as to signal the functionality of the pocket 47 prior to use.

The pocket 47 may extend to the lateral edge of the chassis and creates channels for facilitating the flow of runny bowel movement. This open channel area can be sealed by any suitable bonding technique such as glue, mechanical bonds, thermal bonds, or the like.

The hydrophobic properties, such as Low Surface Tension Strikethrough or Hydro Head, can be increased in a least a portion of the pocket 47, in such a way that prevents exudates from leaking through the materials that comprise the pocket. Accordingly, this will maintain separation of the contained fecal material from the wearer. Increasing hydrophobic properties can be accomplished by applying hydrophobic coatings, inks, glues, silicones, additional materials, or any combination thereof, or by any other means known in the art.

The outer cuff 74 and inner cuff 71 may be the same color. The outer cuff 74 and inner cuff 71 may be different colors. There may be an additional printing on one or more of the cuffs of the leg gasketing system 70. In absorbent articles with printing on both the inner and outer cuffs, the printing may be the same or different on each cuff.

The leg gasketing system 70 may include a printed zone that outlines or defines at least a portion of the pocket 47 such that the benefit can be signaled prior to use.

The outer cuff 74 may comprise elastic members 77 positioned in a lateral array between the outer cuff folded edge 75 and outer cuff material edge 76. As illustrated in FIGS. 2-4, the elastics 77, 78 are attached to the portion of the web of material that forms the outer cuff by elastics adhesive 79. In such an absorbent article, the elastics are positioned between 1) the portion of the web of material between the outer cuff folded edge 75 and the outer cuff material edge 76, and 2) the portion of the web material between the outer cuff folded edge 75 and the inner cuff folded edge 72. The outer cuff 74 may comprise at least two elastic members 77, at least three elastic members 77, at least four elastic members 77, at least five elastic members 77, or at least six elastic members 77. The elastic members 77 may be disposed between the outer cuff folded edge 75 and the inner cuff material edge 73.

The inner cuff 71 may comprise an array of elastic members 78 positioned in a lateral array between the inner cuff folded edge 72 and the inner cuff material edge 73. The elastics attached to the portion of the web of material that forms the inner cuff by elastics adhesive 79. In such an absorbent article, the elastics are positioned between 1) the portion of the web of material between the inner cuff folded edge 72 and the inner cuff material edge 73, and 2) the portion of the web material between the inner cuff folded edge 72 and the outer cuff folded edge 75. The inner cuff 71 may comprise at least one elastic member 78, at least two elastic members 78, at least three elastic members 78, at least four elastic members 78, or at least five elastic members 78. The elastic members 78 may be disposed between the inner cuff folded edge 72 and the outer cuff material edge 76.

The outer cuff 74 may comprise at least one more elastic member 77 than the inner cuff 71 elastic member(s) 78. The inner cuff material edge 73 may be laterally outboard the outer cuff material edge 76.

The elastic members 77 and 78 may be spaced at least 2 mm apart from one edge of the member to the other edge of the member, optionally at least 3 mm apart; optionally at least 3.5 mm apart; optionally at least 4 mm apart; optionally at least 4.5 mm apart; optionally at least 5 mm apart; optionally at least 5.5 mm apart; optionally at least 6 mm apart; optionally at least 6.5 mm apart; optionally at least 7 mm apart; optionally at least 7.5 mm apart; optionally at least 8 mm apart; optionally at least 8.5 mm apart; optionally at least 9 mm apart; optionally at least 9.5 mm apart; optionally at least 10 mm apart; optionally at least 10.5 mm apart; optionally at least 11 mm apart; optionally at least 11.5 mm apart; optionally at least 12 mm apart. The outermost elastic members 77 and 78 may be less than about 2 mm from the outer cuff material edge 76 and inner cuff material edge 73; optionally less than about 1.5 mm, less than about 1 mm.

The outer cuff 74 may have four elastic members 77 that are about 4 mm apart. The outer cuff 74 may have four elastic members that are about 2 mm/7 mm/2 mm apart. The outer cuff 74 may have three elastic members 77 that are about 6 mm apart. The outer cuff 74 may have two elastic members that are about 12 mm apart. The outer cuff 74 may have two elastic members that are about 3 mm/6 mm/3 mm apart, as spaced from the outer cuff folded edge 75. The elastic members may be about 2 mm from the outer cuff folded edge 75, optionally about 0 mm from the outer cuff folded edge 75.

The leg gasketing system 70 may have an inner cuff 71 comprised of an inner cuff folded edge 72 and an inner cuff material edge 73. The leg gasketing system 70 may further comprise an outer cuff 74 comprising an outer cuff folded edge 75 and an outer cuff material edge 76. The leg gasketing system may comprise a first material comprising the inner cuff 71 and a second material comprising the outer cuff 74. The first and second material may overlap and be joined together along a longitudinal edge of each material by any suitable bonding means (i.e., a single web), or be separate webs of material. The web of material may be folded laterally inward to form the outer cuff folded edge 75 and folded laterally outward to form the inner cuff folded edge 72. The proximal edges of the outer cuff 74 may be coterminous. The proximal edges of the outer cuff 74 may be spaced greater than about 2 mm apart; greater than about 4 mm; greater than about 6 mm; greater than about 10 mm apart. The proximal material edges of the cuff may be both bonded to the inner cuff. Only one of the proximal material edges of the outer cuff 74 may be bonded to the inner cuff. The proximal material edges of the outer cuff may be held together with any suitable bonding means.

The leg gasketing system 70 may be spaced laterally inward of the chassis longitudinal edge 12 by about 10 mm, optionally about 20 mm, optionally about 30 mm, optionally about 60 mm or more. The laterally outboard edge of the chassis may be defined by the lateral edge of the outer cuff. The backsheet and/or polymeric film may be spaced laterally inward of the outer cuff edge by about 10 mm; optionally about 20 mm; optionally about 30 mm; optionally about 40 mm.

The laterally outboard edge of the leg gasketing system 70 may be disposed laterally inboard of at least a portion of the longitudinal edge of the article in at least one of the waist regions. Thus, the front ears 40 and/or back ears 42 may extend past the leg gasketing system 70.

The height of the inner cuff 71 may be at least about 10 mm, at least about 20 mm, a least about 30 mm, at least about 32 mm, at least about 35 mm, at least about 38 mm. The height of the outer cuff 74 may be at least about 15 mm, at least about 23 mm, at least about 25 mm, at least about 27 mm, at least about 30 mm. The height of the inner cuff is measured from inner cuff folded edge 72 to the first point of connection to a material beyond the inner cuff material edge 73 in the crotch region. The outer cuff height is measured from the outer cuff folded edge 75 to the first point of connection the inner cuff 72 has to a material beyond the inner cuff material edge 73 in the crotch region. Thus, the inner and outer cuffs are measured from their respective folded edges to the point where the inner cuff is connected to the first material beyond the inner cuff material edge.

One advantage of the leg gasketing system 70 detailed herein is that when a substantially liquid-impervious material is used in construction of the cuff, the polymeric film layer may be narrowed or not present at all, resulting in more cost effective designs. Utilizing adhesive technologies that are more reliably processed results in more reliable performance and creates substantially liquid impervious seals. This technology enables narrowing the film layer to be only slightly wider than the absorbent core by reducing the need for redundant seals.

The backsheet polymeric film may be less than about 50 mm wider than the absorbent core; optionally less than about 40 mm wider, less than about 30 mm wider. The backsheet polymeric film may be at least about 20 mm more narrow than the chassis width; optionally at least about 40 mm more narrow than the chassis width; optionally at least about 60 mm more narrow than the chassis width; optionally at least about 80 mm more narrow than the chassis width; optionally at least about 100 mm more narrow than the chassis width; optionally at least about 120 mm more narrow than the chassis width.

The leg cuff may be joined to the topsheet and/or backsheet by a slot coated adhesive. At least about 12 gsm of adhesive may be applied; optionally at least about 15 gsm of adhesive is applied; optionally at least about 20 gsm of adhesive is applied; optionally, at least about 25 gsm of adhesive is applied; optionally at least about 40 gsm of adhesive is applied; optionally at least about 60 gsm of adhesive is applied. The adhesive may be at least about 1 mm wide; optionally at least about 3 mm wide; optionally at least about 7 mm wide. The adhesive may be at least about 2 mm inboard of the outboard lateral edge of the film; optionally at least 4 mm inboard of the outboard lateral edge of the film; optionally at least about 6 mm inboard of the outboard lateral edge of the film. The leg cuff may be joined to the topsheet and/or backsheet by two overlapping and redundant spiral adhesive sprays; optionally three overlapping and redundant spiral adhesive sprays.

The descriptions of the invention including the pocket 47 and opening 51 that allow for trapping exudates can be used in conjunction with an article that does not contain an absorbent core. This is useful for a product that is designed to be used in the medical industry as it can enable the collection of exudates for analysis easier without the exudates being absorbed into the product.

Figure 11Q:
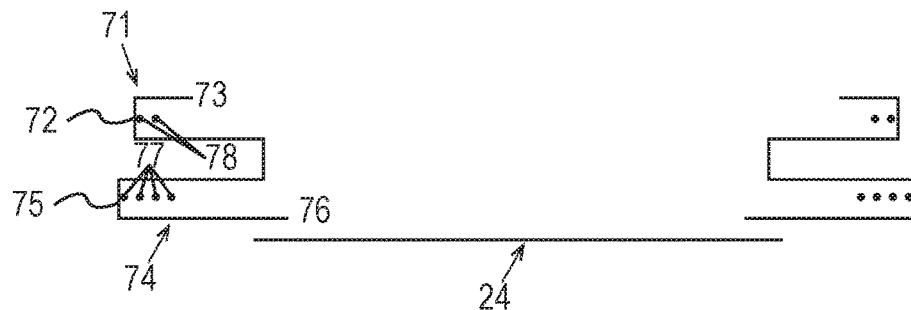
FIGS. 11a-t are schematic cross sectional views of additional leg gasketing systems suitable for use in the absorbent articles detailed herein.
Figure 11R:
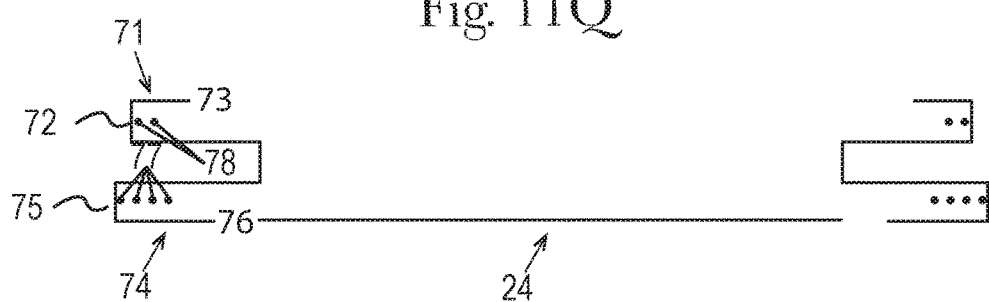
Figure 11S:
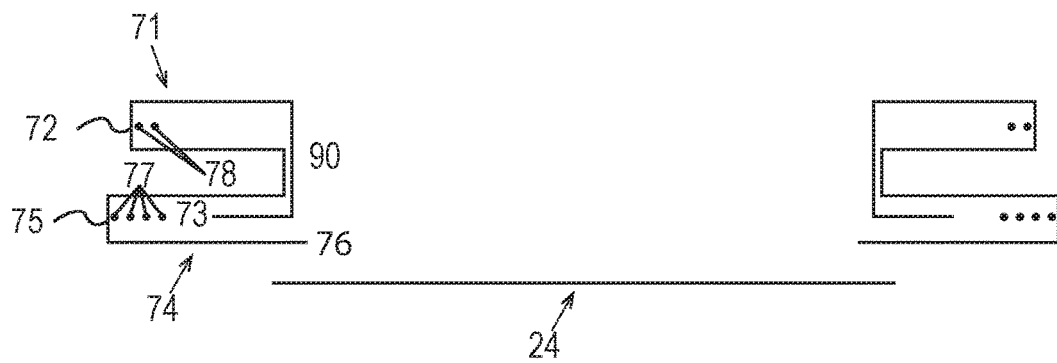
Figure 11T:
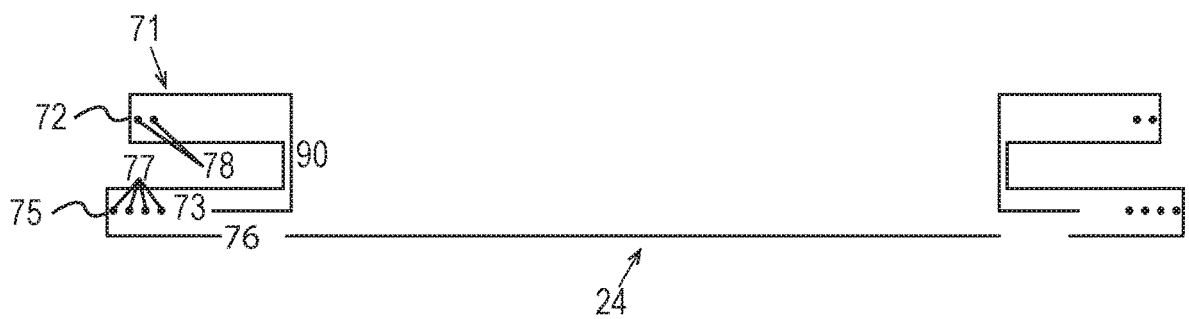

Additional leg gasketing systems 70 that are be useful in the absorbent articles detailed herein are shown in FIGS. 11a-11t of the accompanying drawings.

Opacity Strengthening Patch:

An opacity strengthening patch 80 may be included as part of the chassis 22. The opacity strengthening patch 80 is an additional layer of material. The opacity strengthening patch 80 may be connected to the leg gasketing system 70, the polymeric film layer, or the backsheet 26. The opacity strengthening patch 80 may be disposed between the backsheet 26 and leg gasketing system 70 in either the first waist region 36, the second waist region 38, or both the first waist region 36 and the second waist region 38 of the article; the opacity strengthening patch 80 may overlap at least one of the the leg gasketing system 70 and/or the polymeric film layer (i.e., inner layer of the backsheet 26). The opacity strengthening patch 80 may be attached to one or both of the leg gasketing system 70 or the polymer film layer using any suitable means such as glue, mechanical bonds, thermal bonds, or the like, so that loads generated during the application process or during wear can be transferred from the lateral edge of the article to the leg gasketing system 70 and/or the polymeric film layer. The opacity strengthening patch is useful in providing the strength needed to prevent the article from extending excessively during application and wearing; it also may provide opacity at the sides and waist to prevent the skin of the user from showing through the article. Thus, the patch 80 may be located at any portion of the chassis 22 where strength and opacity is desirable. Materials suitable to act as the opacity strengthening patch include materials having a basis weight of at least about 10 gsm, at least about 15 gsm, at least about 25 gsm. An opacity strengthening patch useful herein may exhibit the following tensile properties in the cross direction: at 2% engineering strain for a 1 inch wide sample, 0.4N; at 5% engineering strain for a 1 inch wide sample, 1.25N; at 10% engineering strain for a 1 inch wide sample, 2.5N. One opacity strengthening patch useful herein is available from Pegas, Znojmo, CZ, as supplier number 803968.

The opacity strengthening patch 80 may be discrete and is located in the front and back waist regions of the article. The opacity strengthening patch may be about 70 mm long in the front, optionally about 90 mm long in the front; optionally about 120 mm long in the front. The opacity strengthening patch may be about 70 mm long in the back, optionally about 100 mm long in the back, optionally about 140 mm long in the back. The opacity strengthening patch may be continuous and spans the entire length of the product.

The opacity strengthening patch may have a hunter color opacity of greater than about 15%, optionally greater than about 25%, optionally greater than about 40%, optionally greater than 60%.

The opacity strengthening patch may be laterally outboard of the polymeric film layer. The opacity strengthening patch may overlap the polymeric film layer in the lateral direction such that it can be affixed to the polymeric film in order to transmit laterally directed application and wearing forces from the opacity strengthening patch to the polymeric film layer. Any suitable bonding means known in the art may be used to affix the opacity strengthening patch to the polymeric film layer. The opacity strengthening patch may overlap the polymeric film layer by about 5 mm, optionally about 10 mm, optionally about 15 mm, optionally about 20 mm, optionally less than about 30 mm.

There may be a lateral gap between the opacity strengthening patch and the polymeric film layer and the opacity strengthening patch is affixed by any suitable bonding means to the leg gasketing system, and the leg gasketing system is affixed to the polymeric film layer by any suitable bonding means such that application and wearing loads can transmit from the opacity strengthening patch to the gasketing system and then from the gasketing system to the polymeric film layer. The gap may preferably be less than 30 mm, more preferably less than 20 mm, more preferably less than 10 mm.

There may be a lateral gap between the opacity strengthening patch and the polymeric film layer; the opacity strengthening patch may be affixed by any suitable bonding means to the leg gasketing system and the body facing and garment facing sides of the leg gasketing system may be affixed together by any suitable bonding means so that the loads from the opacity strengthening patch are shared by both layers of the leg gasketing system. The leg gasketing system may be affixed to the polymeric film layer by any suitable bonding means such that application and wearing loads can transmit from the opacity strengthening patch to the leg gasketing system and then from the leg gasketing system to the polymeric film layer.

The opacity strengthening patch may overlap the leg gasketing system in the lateral direction such that it can be affixed securely to the opacity strengthening patch layer by any suitable bonding means as a way to transmit application and wearing forces from the opacity strengthening patch to the leg gasketing system. The opacity strengthening patch may overlap the leg gasketing system by about 5 mm, optionally about 10 mm, optionally less than about 15 mm, optionally less than about 25 mm.

The leg gasketing system may have about the same lateral tensile strength properties as the opacity strengthening patch. The combined properties of the leg gasketing system and the backsheet nonwoven outer cover may have about the same lateral tensile strength as the opacity strengthening patch. Alternately, the outercover nonwoven may have very low lateral strength between about 0% and about 10% engineering strain. The outercover nonwoven may exhibit the following tensile properties: at 10% engineering strain for a 1 inch wide sample, 0.4N.

Waistband:

Waistbands utilized in the absorbent articles detailed herein may result in absorbent articles having increased comfort, fit, and improved leakage performance for the wearer. Certain waistbands may also provide improved product durability and strength. The waistbands detailed herein may also result an easier and improved absorbent article changing experience.

The absorbent articles detailed herein may have an improved gap closure in the first and/or second waist regions of the absorbent article than what is currently known in the art today. Having gap closure in the waist regions may create an article with better fit and containment, resulting in improved leakage performance. One way to achieve gap closure is to provide a waistband that is flush coterminous with the rear lateral edge of the absorbent article. Because there is variation in the application process, a waistband may be present in both the first and second waist regions of the absorbent article. However, while a highly contracted waistband is desirable for the back waist region to provide stretch, it may be more desirable to have a less contracted waistband in the front waist region to aid in application. Therefore, articles detailed herein may be directed to "differential contraction" or waistband laminates having different installed elongation strands in the front versus the back, such that only one waistband laminate is cut. Cutting of the waistband laminate is subsequent to the waistband application to the article; the waistband is applied such that it spans the intended article separation (cut) zone. Thus, the same waistband laminate can deliver different levels of contraction in the back and front, resulting in higher contraction in the back to help close the gap and lower contraction in the front.

The first and second waistbands may be comprised of a waistband laminate. The waistband laminate may be comprised of a nonwoven material. The waistband laminate may be comprised of a film. The waistband laminate may be comprised of at least two elastic strands, at least four elastic strands, at least six elastic strands, at least eight elastic strands, at least ten elastic strands, at least twelve elastic strands.

The first and second waistbands may be applied to the article at the same applied waistband strain. The first waistband and the second waistband may be applied to the disposable absorbent article at a strain of greater than about 30%, greater than about 50%, greater than about 70% as compared to the relaxed length. The first waistband and the second waistband may be applied to the disposable absorbent article at a strain of less than about 150%, less than about 125%, less than about 100%, less than about 75% as compared to the relaxed length. The first waistband and the second waistband may be applied to the disposable absorbent article at a strain of from about 70% to about 75% as compared to the relaxed length.

The waistband laminate may be comprised of a nonwoven material and at least two elastic strands, wherein each of the at least two elastic strands are different elastic materials. The elastic strands may have different diameters or cross-sectional geometry.

The waistband laminate may be cut after application to the article between the elastic strands such that a waistband laminate comprised of at least two elastic strands results in two waistbands each having one elastic strand; a waistband laminate comprised of at least four elastic strands results in two waistbands each having two elastic strands. A waistband laminate may be comprised of at least six elastic strands results in two waistbands each having three elastic strands when cut. Further, a waistband laminate comprised of at least eight elastic strands results in two waistbands each having four elastic strands, a waistband laminate comprised of at least ten elastic strands results in two waistbands each having five elastic strands, a waistband laminate comprised of at least twelve elastic strands results in two waistbands each having six elastic strands. The waistband laminate may be cut such that the two resulting waistbands have an unequal distribution of elastic strands or having no elastic strands on one side of the cut. For example, a waistband laminate having ten elastic strands may result in one waistband having six elastics and one waistband having four elastics. In another example, a waistband laminate having ten elastic strands may result in one waistband having ten elastics and one waistband having no elastics. The waistband laminate may be cut in the center to create the two waistbands. The waistband laminate may be cut off-center. The waistband laminate may have elastic strands spaced equally apart. The waistband laminate may have strands spaced closer together or further apart as compared to the other elastic strands in the laminate.

The waistband may have a length in the direction parallel to the longitudinal axis of the article of greater than about 12 mm, greater than about 15 mm, greater than about 20 mm. The waistband may have a length in the direction parallel to the longitudinal axis of the article of less than about 50 mm, less than about 45 mm, less than about 40 mm.

The waistband in a relaxed product may have a length in the direction parallel to the lateral axis of the article of greater than about 50 mm, greater than about 75 mm, greater than about 100 mm. The length in the direction parallel to the lateral axis of the article of the waistband in a relaxed product may be less than about 300 mm, less than about 250 mm, less than about 200 mm.

The CD Length Ratio of the waistband compared to the distance from one tape to the other tape may be less than about 2, less than about 1.5, about 1.

The waistband may be on the body-facing surface of the article. The waistband may be on the garment-facing surface of the article. The waistband may be sandwiched in between the layers of the absorbent article. The waistband may be on the garment-facing surface in either the first or second waist regions and on the body-facing surface in either the first or second waist regions. The waistband may be on both the body-facing surface and the garment-facing surface. The waistband may be on either the body-facing surface or the garment-facing surface and the surface not comprising the waistband is printed with a printed waistband feature.

The distance from one tape edge to the other tape edge may be at least about 50% the average length of the baby waist circumference for an average baby that wears the size of absorbent article; at least about 60% the average length; at least about 65% the average length.

The elastic strands of the waistband laminate may have different installed elongations within one laminate, thus, after being cut, resulting in a first waistband having a first installed elongation and a second waistband having a second installed elongation; both the first and second waistbands have the same applied waistband strain. The installed elongation is the strain at which the elastic is under relative to the second material that it is combined with (e.g. low basis weight nonwoven). For example, if the elastic is stretched from 100 mm to 250 mm when it is combined with the nonwoven, it would be said to be 150% installed elongation or ((250 mm/100 mm)−1)×100%. This laminate can then be allowed to relax and will return to about the original 100 mm, but with 250 mm of nonwoven. There can be more than one installed elongation within one waistband laminate if the elastics are strained to a different degree. For example, strand (1) is stretched from 100 mm to 250 mm when combined with the nonwoven or has 150% installed elongation while strand (2) is stretched from 90 mm to 250 mm when combined with the NW or has an installed elongation of about 178%.

The Applied Waistband Strain is the strain that the waistband laminate is under when combined with the absorbent article. For example if 100 mm of laminate is stretched to 170 mm when applied it would be considered to be 70% applied waistband strain or ((170 mm-100 mm)/100 mm×100%). The first installed elongation of any number of elastic strands may be about 100%, about 125%, about 140%, about 150%, about 160%, about 175%, about 200%. The second installed elongation of any number of elastic strands may be about 100%, about 125%, about 140%, about 150%, about 160%, about 175%, about 200%.

The delta between the first installed elongation and the second installed elongation may be greater than about 20%, greater than about 30%, greater than about 40%.

The resulting Front-to-Back Delta Chassis Contraction may be greater than about 5.0%, greater than about 9.0%, greater than about 9.5%, greater than about 12.5%, greater than about 15%, greater than about 20%.

The Front-to-Back Delta Chassis Contraction may be less than about 15%, less than about 12.5%, less than about 10%, less than about 9.5%, less than about 9% when either the front chassis contraction or the back chassis contraction is greater than about 18%, greater than about 20%.

Differential Contraction Examples:

| Products | Front Waist Relaxed Chassis Width (mm) RCFW | Front Stretched Chassis Width (mm) ECFW | Front Chassis Contraction (%) FCC | Back Waist Relaxed Chassis Width (mm) RCBW | Back Stretched Chassis Width (mm) ECBW | Back Chassis Contraction (%) BCC | Front-to-Back Delta in Chassis Contraction (%) Delta CC |
|---|---|---|---|---|---|---|---|
| Anerle Diaper (1) | 294 | 330 | 10.91 | 296 | 332 | 10.84 | 0.1 |
| Parents Choice Diaper (2) | 251 | 286 | 12.24 | 247 | 288 | 14.24 | 2.0 |
| Moony Diaper (3) | 202 | 232 | 12.93 | 197 | 238 | 17.23 | 4.3 |
| Huggies Baby Steps (4) | 296 | 340 | 12.94 | 299 | 335 | 10.75 | 2.2 |
| Huggies Supreme (5) | 251 | 270 | 6.91 | 231 | 270 | 14.34 | 7.4 |
| Drypers (6) | 300 | 350 | 14.29 | 284 | 332 | 14.46 | 0.2 |

(1) Anerle Taped Diaper from Philippines, Size L (9-13 kg), SKU 90324495220, Lot 20121009 WP071157C9236; green foam sandwiched waistband (2) Parents Choice Taped Diaper (2) from North America, Lot 9344 M02 1759 S-1855; white foam sandwiched waistband (3) Moony Taped Diaper from Japan, Lot 910193071; green foam sandwiched waistband (4) Huggies Baby Steps US, 1991, Size 4, Lot 3U251910248; white foam sandwiched waistband in blue film (5) Huggies Supreme 2001, Size 4, Lot NM127501F0755; green nonwoven waistband with small denier elastic strands in white film (6) Drypers, US, Size Large, Sep. 8, 1998; white foam sandwiched waistband white film

| Examples | Front Waist Relaxed Chassis Width (mm) RCFW | Front Stretched Chassis Width (mm) ECFW | Front Chassis Contraction (%) FCC | Back Waist Relaxed Chassis Width (mm) RCBW | Back Stretched Chassis Width (mm) ECBW | Back Chassis Contraction (%) BCC | Front-to-Back Delta Chassis Contraction (%) Delta CC |
|---|---|---|---|---|---|---|---|
| A | 171 | 212.2 | 24.1 | 160 | 212.4 | 32.8 | 8.7 |
| B | 175.2 | 212.6 | 21.3 | 165.2 | 212.6 | 28.7 | 7.3 |
| C | 179.6 | 212.6 | 18.4 | 166.2 | 212.6 | 27.9 | 9.5 |
| D | 179.4 | 212.4 | 18.4 | 164.2 | 212.8 | 29.6 | 11.2 |
| E | 191.2 | 212.4 | 11.1 | 163.6 | 212.4 | 29.8 | 18.7 |
| F | 184.6 | 212.2 | 15.0 | 170.6 | 212.6 | 24.6 | 9.7 |
| G | 199.4 | 212.2 | 6.4 | 163.6 | 212.6 | 30.0 | 23.5 |

-continued

| Examples | Front Waist Relaxed Chassis Width (mm) RCFW | Front Stretched Chassis Width (mm) ECFW | Front Chassis Contraction (%) FCC | Back Waist Relaxed Chassis Width (mm) RCBW | Back Stretched Chassis Width (mm) ECBW | Back Chassis Contraction (%) BCC | Front-to-Back Delta Chassis Contraction (%) Delta CC |
|---|---|---|---|---|---|---|---|
| H | 192.4 | 212.6 | 10.5 | 165 | 213 | 29.1 | 18.6 |
| I | 201.6 | 212.4 | 5.4 | 165 | 212.4 | 28.7 | 23.4 |
| J | 208.8 | 212.8 | 1.9 | 164.2 | 212.8 | 29.6 | 27.7 |

A—Installed Elongation: 150%; Waistband Strain: 150%; Delta Front/Back Installed Elongation: 0
B—Installed Elongation: 200%; Waistband Strain: 200%; Delta Front/Back Installed Elongation: 0
C—Installed Elongation: 150%; Waistband Strain: 130%; Delta Front/Back Installed Elongation: 20
D—Installed Elongation: 200%; Waistband Strain: 180%; Delta Front/Back Installed Elongation: 20
E—Installed Elongation: 150%; Waistband Strain: 110%; Delta Front/Back Installed Elongation: 40
F—Installed Elongation: 200%; Waistband Strain: 160%; Delta Front/Back Installed Elongation: 40
G—Installed Elongation: 150%; Waistband Strain: 100%; Delta Front/Back Installed Elongation: 50
H—Installed Elongation: 200%; Waistband Strain: 140%; Delta Front/Back Installed Elongation: 60
I—Installed Elongation: 200%; Waistband Strain: 120%; Delta Front/Back Installed Elongation: 80
J—Installed Elongation: 200%; Waistband Strain: 100%; Delta Front/Back Installed Elongation: 100

Another object of the absorbent articles detailed herein is to deliver a better balance of thickness (caliper)/cushion and contraction in a waistband than what is currently known in the art. Presently, most waistbands are either foam based which have good cushion/caliper for comfort and containment but are limited in the amount of contraction or the waistbands are a combination of elastic strands and nonwoven where the elastic strands are pulled at high strain which delivers high contraction, but very little caliper/cushion in use. Thus, one article disclosed herein is directed to "consolidation" which provides a waistband having the nonwoven material and the elastic strand(s) combined under a higher first strain (installed elongation) and the resulting waistband attached to the article under a lower applied waistband strain, such that the folded up nonwoven in the waistband provides a cushion/caliper in both the relaxed and stretched/in use states.

The waistband may be comprised of a laminate comprising a nonwoven material and at least one elastic strand, wherein the nonwoven material and the elastic strand(s) are combined under a first strain and the waistband is attached to the article under an applied waistband strain. The first strain, also referred to as the installed strand elongation, may be greater than about 50%, greater than about 75%, greater than about 100%, greater than about 150%, greater than about 200%, greater than about 225%, greater than about 250%, greater than about 300%, greater than about 350%, greater than about 375%. The applied waistband strain, also referred to as the waistband strain, may be greater than about 25%, greater than about 50%, greater than about 75%, greater than about 100%. The difference between the first strain and the applied waistband strain, also referred to as Consolidation, may be greater than about 0%, greater than about 65%, greater than about 75%, greater than about 100%, greater than about 150%, greater than about 200%, greater than about 225%, greater than about 250%, greater than about 300%.

The waistband may have a Full Waistband Consolidation greater than about 95%, greater than about 100%, greater than about 125%, greater than about 150%, greater than about 175%, greater than about 200%.

The waistband may have an Extended Waistband Consolidation greater than about 35%, greater than about 50%, greater than about 75%, greater than about 100%, greater than about 125%, greater than about 175%.

The waistband may be attached near the waist edge. The waistband may be attached within 20 mm of the waist edge. The waistband may be attached flush with the waist edge. The waistband may be present only at one waist edge. The waistband may be present at both the first and second waistband edges.

The nonwoven material and the elastic strand(s) may be combined with adhesive, mechanical bonds, or any other forms of attachment known in the art. The waistband may be attached to the article with adhesive, mechanical bonds, or any other forms of attachment known in the art.

The relaxed caliper of the waistband may be greater than about 1.60 mm, greater than about 2.00 mm, greater than about 2.25 mm, greater than about 2.50 mm.

The extended caliper of the waistband may be greater than about 0.80 mm, greater than about 1.00 mm, greater than about 1.25 mm.

Consolidation Examples:

| Products | Relaxed Caliper (mm) | Extended Caliper (mm) | Chassis Extended Length CEL (mm) | Relaxed Length RWL (mm) | Total Length EWL (mm) | Full Waistband Consolidation (%) | Extended Waistband Consolidation (%) |
|---|---|---|---|---|---|---|---|
| Huggies Snug & Dry (7) | 0.91 | 0.55 | 237 | 172 | 273 | 59 | −14 |
| Huggies Little Movers (8) | 1.08 | 0.61 | 223 | 155 | 241 | 56 | −14 |
| Huggies Overnight (9) | 1.45 | 0.70 | 220 | 131 | 253 | 93 | 33 |
| K | 1.64 | 0.40 | 205 | 125 | 201 | 60 | −1 |

-continued

| Products | Relaxed Caliper (mm) | Extended Caliper (mm) | Chassis Extended Length CEL (mm) | Relaxed Length RWL (mm) | Total Length EWL (mm) | Full Waistband Consolidation (%) | Extended Waistband Consolidation (%) |
|---|---|---|---|---|---|---|---|
| L | 2.24 | 0.71 | 208 | 132 | 286 | 116 | 53 |
| M | 2.40 | 1.04 | 203 | 130 | 340 | 162 | 98 |
| N | 2.54 | 1.01 | 205 | 131 | 386 | 195 | 131 |
| O | 2.22 | 1.29 | 205 | 126 | 425 | 237 | 176 |

(7) Huggies Snug & Dry, size 4; Lot No. BI 103108B
(8) Huggies Little Movers, size 3; Lot No. BI 024610B
(9) Huggies Overnight, size 4; Lot No. PA 027104F
K—75% Installed Elongation and 75% Waistband Strain
L—150% Installed Elongation and 75% Waistband Strain
M—225% Installed Elongation and 75% Waistband Strain
N—300% Installed Elongation and 75% Waistband Strain
O—375% Installed Elongation and 75% Waistband Strain Another object of the present invention is to deliver an integrated leg gasketing system and front/back waistband feature that provides extra leakage protection around the perimeter of the article. Thus, one version of the present invention is directed to "360 Leakage Protection" which provides a common leg gasketing system and waistband with similar construction having similar gather counts. Additional articles may include leg gasketing systems and waistbands that overlap or have similar tints, textures, bond patterns, colors, or other visual cues.

The disposable absorbent article may comprise a waistband and a leg gasketing system, as described herein, wherein the leg gasketing system has a first gather count and the waistband has a second gather count such that the ratio of the first gather count to the second gather count is greater than about 0.5, greater than about 0.75, less than about 1.25, less than about 1.50. The ratio of the first gather count to the second gather count may be about 1.00. The ratio of the first gather count to the second gather count may be from about 0.75 to about 1.25. The ratio of the first gather count to the second gather count may be from about 0.75 to about 1.25, when the leg gasketing system gather count is greater than about 13. The ratio of the first gather count to the second gather count may be from about 0.75 to about 1.25, when the waistband gather count is greater than about 12. The ratio of the first gather count to the second gather count may be from about 0.75 to about 1.25, when the absorbent article is a taped-type product.

Both of the waistband and leg gasketing system may comprise elastic strands; the waistband may comprise elastic strands; both the waistband and leg gasketing system may comprise the same type of stretch material and/or laminate structure.

The waistband may have greater than about 10 gathers per 30 mm section, greater than about 12 gathers per 30 mm section. The leg gasketing system may have greater than about 10 gathers per 30 mm section, greater than about 12 gathers per 30 mm section.

The waistband may be present in the first waist edge and the second waist edge and the leg gasketing system is present in the first longitudinal edge and the second longitudinal edge.

360 Leakage Protection Examples:

| Products | Average Leg Gasketing System Gather Count | Average Waistband Gather Count | Ratio of Leg Gasketing System Gather Count to Waistband Gather Count |
|---|---|---|---|
| P | 20.7 | 22.2 | 0.9 |
| Q | 21.2 | 21.2 | 1.0 |
| R | 16.7 | 18.2 | 0.9 |
| Huggies Baby Steps (4) | 23.2 | 12.5 | 1.9 |
| Huggies Supreme (5) | 17.0 | 24.0 | 0.7 |
| Anerle Diaper (1) | 20.0 | 16.0 | 1.3 |
| Parent Choice (2) | 20.0 | 15.5 | 1.3 |
| Moony Diaper (3) | 12.5 | 11.2 | 1.1 |

P—150% Installed Elongation, 75% Waistband Strain
R—150% Installed Elongation, 75% Waistband Strain
Q—150% Installed Elongation, 75% Waistband Strain Construction Materials:

It is recognized that there are many combinations of material lateral tensile properties that could form a substantially suitable force transmission pathway in the waist region or the article without excessive lateral stretch in the waist region, and that the material force pathways may go from the opacity strengthening patch directly into the polymeric film layer or into the polymeric film layer through a variety of other layers in the region immediately outboard the polymeric film layer. These layers may include the topsheet, backsheet nonwoven, cuff, absorbent assembly, leg gasketing system, or any other layer that is located in a region adjacent to the polymeric film layer.

The material of the leg gasketing system 70 may be made from a substantially liquid impervious material. The material may be selected from the group consisting of an SMS nonwoven, SMMS nonwoven material, or a nonwoven component layer comprising "N-fibers".

Various nonwoven fabric webs may comprise spunbond, meltblown, spunbond ("SMS") webs comprising outer layers of spunbond thermoplastics (e.g., polyolefins) and an interior layer of meltblown thermoplastics. The leg gasketing cuff 70 may comprise a nonwoven component layer having fine fibers ("N-fibers") with an average diameter of less than 1 micron (an "N-fiber layer") may be added to, or otherwise incorporated with, other nonwoven component layers to form a nonwoven web of material. The N-fiber layer may be used to produce a SNS nonwoven web or SMNS nonwoven web, for example.

The leg gasketing cuff 70 may comprise a first nonwoven component layer comprising fibers having an average diameter in the range of about 8 microns to about 30 microns, a second nonwoven component layer comprising fibers having a number-average diameter of less than about 1 micron, a mass-average diameter of less than about 1.5 microns, and a ratio of the mass-average diameter to the number-average diameter less than about 2, and a third nonwoven component layer comprising fibers having an average diameter in the range of about 8 microns to about 30 microns. The second nonwoven component layer is disposed intermediate the first nonwoven component layer and the third nonwoven component layer.

The N-fibers may be comprised of a polymer, e.g., selected from polyesters, including PET and PBT, polylactic acid (PLA), alkyds, polyolefins, including polypropylene (PP), polyethylene (PE), and polybutylene (PB), olefinic copolymers from ethylene and propylene, elastomeric polymers including thermoplastic polyurethanes (TPU) and styrenic block-copolymers (linear and radial di- and tri-block copolymers such as various types of Kraton), polystyrenes, polyamides, PHA (polyhydroxyalkanoates) and e.g. PHB (polyhydroxubutyrate), and starch-based compositions including thermoplastic starch, for example. The above polymers may be used as homopolymers, copolymers, e.g., copolymers of ethylene and propylene, blends, and alloys thereof. The N-fiber layer may be bonded to the other nonwoven component layers by any suitable bonding technique, such as the calendar bond process, for example, also called thermal point bonding.

The use of an N-fiber layer in a nonwoven web may provide a low surface tension barrier that is as high as other nonwoven webs that have been treated with a hydrophobic coating or a hydrophobic melt-additive, and still maintain a low basis weight (e.g., less than 15 gsm or, alternatively, less than 13 gsm). The use of the N-fiber layer may also provide a soft and breathable (i.e., air permeable) nonwoven material that may be used in single web layer configurations in applications which previously used double web layer configurations. Furthermore, the use of the N-fiber layer may at least reduce the undesirable migration of hydrophilic surfactants toward the web and, therefore, may ultimately result in better leak protection for an associated absorbent article. Also, when compared to an SMS web having a similar basis weight, the use of a nonwoven web comprising the N-fiber layer may decrease the number of defects (i.e., holes or pinholes through the mechanical bond site) created during the mechanical bonding process. N-fibers are further discussed in WO 2005/095700 and U.S. patent application Ser. No. 13/024,844.

The inner cuff 71 web of material may have a hydrostatic head of greater than about 2 mbar, greater than about 3 mbar, greater than about 4 mbar. The outer cuff 74 web of material may have a hydrostatic head of less than about 200 mbar, less than about 100 mbar, less than about 75 mbar, less than about 50 mbar, less than about 25 mbar, less than about 15 mbar.

The folded outer cuff web of material may have a basis weight of 10 gsm; optionally 13 gsm; optionally 15 gsm; optionally 18 gsm.

The inner cuff 71 web of material may have an opacity of from about 15% to about 50% hunter opacity; optionally from about 20% to about 45% hunter opacity. The outer cuff 74 web of material may have an opacity of from about 45% to about 75% hunter opacity; optionally from about 50% to about 70% hunter opacity; optionally less than about 75% hunter opacity; optionally less than about 70% hunter opacity.

The inner cuff 71 web of material may have an air permeability of less than about 50 $m^3/m^2/min$; optionally less than about 45 $m^3/m^2/min$. The outer cuff 74 web of material may have an air permeability of greater than about 5 $m^3/m^2/min$; optionally greater than about 10 $m^3/m^2/min$; optionally greater than about 15 $m^3/m^2/min$; optionally greater than about 20 $m^3/m^2/min$.

The inner cuff 71 web of material may have a WVTR of less than about 5500 $g/m^2/24$ hrs; optionally less than about 5400 $g/m^2/24$ hrs. The outer cuff 74 web of material may have a WVTR of greater than about 4250 $g/m^2/24$ hrs; optionally greater than about 4500 $g/m^2/24$ hrs; optionally greater than about 5000 $g/m^2/24$ hrs; optionally greater than about 5250 $g/m^2/24$ hrs; optionally greater than about 5500 $g/m^2/24$ hrs.

The gasketing cuffs 70 may be substantially inelastic or may be elastically extensible to dynamically fit at the wearer's leg. The gasketing cuff 70 may be formed by one or more elastic members 77 and 78 (such as elastic strands) operatively joined to the topsheet 24, backsheet 26, or any other suitable substrate used in the formation of the absorbent article 20. Suitable gasketing cuff construction is further described in U.S. Pat. No. 3,860,003

The inner cuff 71 may span the entire longitudinal length of the absorbent article 20. The inner cuff 71 may be formed by a flap and an elastic member 78 (such as elastic strands). The inner cuff 71 may be a continuous extension of any of the existing materials or elements that form the absorbent article 20.

The inner cuff 71 may comprise a variety of substrates such as plastic films and woven or nonwoven webs of natural fibers (e.g., wood or cotton fibers), synthetic fibers (e.g., polyester or polypropylene fibers), or a combination of natural and synthetic fibers. The flap may comprise a nonwoven web such as spunbond webs, meltblown webs, carded webs, and combinations thereof (e.g., spunbond-meltblown composites and variants). Laminates of the aforementioned substrates may also be used to form the flap. A particularly suitable flap may comprise a nonwoven available from BBA Fiberweb, Brentwood, Tenn. as supplier code 30926. A particularly suitable elastic member is available from Invista, Wichita, Kans. as supplier code T262P. Further description of diapers having inner barrier cuffs and suitable construction of such barrier cuffs may be found in U.S. Pat. Nos. 4,808,178 and 4,909,803. The elastic member 78 may span the longitudinal length of the inner cuff 71. The elastic member 78 may span at least the longitudinal length of the inner cuff 71 within the crotch region 37. It is desirable that the elastic member 78 exhibits sufficient elasticity such that the inner cuff 71 remains in contact with the wearer during normal wear, thereby enhancing the barrier properties of the inner cuff 71. The elastic member 78 may be connected to the flap at opposing longitudinal ends. The flap may be folded over onto itself so as to encircle the elastic member 78.

The inner cuff 71 and/or outer cuff 74 may be treated, in full or in part, with a lotion, as described above with regard to topsheets, or may be fully or partially coated with a hydrophobic surface coating as detailed in U.S. application Ser. No. 11/055,743, which was filed Feb. 10, 2005. Hydrophobic surface coatings usefully herein may include a non-aqueous, solventless, multicomponent silicone composition. The silicone composition includes at least one silicone polymer and is substantially free of aminosilicones. A particularly suitable hydrophobic surface coating is available from Dow Corning MI, Salzburg as supplier code 0010024820.

Examples

| Product | Lot No. | Opacity % Outer Cuff | Opacity % Inner Cuff | Air Permeability $m^3/m^2/min$ Outer Cuff | Air Permeability $m^3/m^2/min$ Inner Cuff | WVTR $g/m^2/24$ hrs Outer Cuff |
| --- | --- | --- | --- | --- | --- | --- |
| Prototype N-Fiber | NA | 58.7 ± 2.2 | 37.6 ± 3.2 | 26.8 ± 5.6 | 36.9 ± 4.6 | 5905 ± 129 |
| Prototype SMS | NA | 65.8 ± 1.8 | 39.0 ± 1.0 | 65.6 ± 11.5 | 38.5 ± 3.8 | 5748 ± 276 |
| Pampers BabyDry | 0089U011390422 | 80.1 ± 0.4 | 38.8 ± 3.8 | 2.1 ± 1.0 | 56.1 ± 6.3 | 4063 ± 67 |
| Luvs | 1047U011390518 | 85.3 ± 1.2 | 36.4 ± 3.4 | 3.1 ± 1.9 | 90.2 ± 9.3 | 304 ± 144 |
| Huggies Little Movers | BI006912B | 80.1 ± 1.0 | 45.4 ± 4.2 | 2.6 ± 0.4 | 45.0 ± 15.7 | 3673 ± 190 |
| Huggies Supreme | NM1275U1F0755 | 72.7 ± 2.2 | 53.6 ± 2.3 | 4.4 ± 1.1 | 145.2 ± 23.2 | 375 ± 77 |

| Product | WVTR $g/m^2/24$ hrs Inner Cuff | Hydrohead mbar Outer Cuff | Hydrohead mbar Inner Cuff | 32 dyne Strikethrough Sec Outer Cuff | 32 dyne Strikethrough Sec Inner Cuff |
| --- | --- | --- | --- | --- | --- |
| Prototype N-Fiber | 5224 ± 87 | 16.8 ± 2.1 | 12.3 ± 1.3 | 21.0 ± 3.5 | 9.2 ± 1.5 |
| Prototype SMS | 5193 ± 145 | 16.3 ± 1.8 | 10.0 ± 1.7 | 15.6 ± 1.9 | 7.6 ± 1.4 |
| Pampers BabyDry | 5252 ± 157 | >200 | 6.7 ± 0.8 | >100 | 10.1 ± 0.5 |
| Luvs | 5244 ± 26 | >200 | 6.5 ± 1.0 | >100 | 11.8 ± 1.4 |
| Huggies Little Movers | 5581 ± 90 | >200 | 8.3 ± 1.3 | >100 | 14.3 ± 3.5 |
| Huggies Supreme | 5688 ± 85 | >200 | 9.2 ± 1.8 | >100 | 14.6 ± 3.1 |

\* Results are expressed as the average ± one standard deviation
\* Prototype N-Fiber is a 13 gsm SMNS available from Polymer Group Inc
\* Prototype SMS is a 15 gsm SMS (Spunbonded-Meltblown-Spunbonded) nonwoven available from Fibertex under the Comfort Line Test Methods:
Opacity Method Opacity is measured using a 0° illumination/45° detection, circumferential optical geometry, spectrophotometer with a computer interface such as the HunterLab LabScan XE running Universal Software (available from Hunter Associates Laboratory Inc., Reston, Va.) or equivalent instrument. Instrument calibration and measurements are made using the standard white and black calibration plates provided by the vendor. All testing is performed in a room maintained at 23±2° C. and 50±2% relative humidity.

The spectrophotometer is conFIG.d for the XYZ color scale, D65 illuminant, 10° standard observer, with UV filter set to nominal. The instrument is standardized according to the manufacturer's procedures using the 0.7 inch port size and 0.5 inch area view. After calibration, the software is set to the Y opacity procedure which prompts the operator to cover the sample with either the white or black calibration tile during the measurement.

Articles are pre-conditioned at 23° C.±2 C° and 50%±2% relative humidity for two hours prior to testing. To obtain a specimen, the article is stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens are prepared from the cuffs on the right side of the article.

The specimen is placed over the measurement port. The specimen should completely cover the port with the surface corresponding to the inner-facing surface of the cuff directed toward the port. The specimen is gently extended until taut in its longitudinal direction so that the cuff lies flat against the port plate. Adhesive tape is applied to secure the cuff to the port plate in its extended state for testing. Tape should not cover any portion of the measurement port. The specimen is then covered with the white standard plate. A reading is taken, then the white tile is removed and replaced with the black standard tile without moving the specimen. A second reading is taken, and the opacity is calculated as follows:

$$\text{Opacity} = (Y\text{ value}_{(black\ backing)}/Y\text{ value}_{(white\ backing)}) \times 100$$

Specimens from five identical articles (10 inner cuff (5 left and 5 right) and 10 outer cuff (5 left and 5 right)) are analyzed and their opacity results recorded. The average opacity for the inner cuffs and the outer cuffs are calculated and report separately, each to the nearest 0.01%.

Water Vapor Transmission Rate Method

Water Vapor Transmission Rate (WVTR) is measured using the wet cup approach. A cylindrical cup is filled with water, maintaining a constant headspace between the water surface and a specimen sealed over the cup's upper opening. The vapor loss is measured gravimetrically after heating the assembled cup for a specified time in an oven. All testing is performed in a room maintained at 23° C.±2 C° and 50%±2% relative humidity.

Articles are preconditioned at 23° C.±2 C° and 50%±2% relative humidity for two hours prior to testing. The article stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff.

In like fashion, inner and outer cuff specimens from the cuffs on the right side of the article are prepared.

Glass straight walled, cylindrical vials, 95 mm tall with a 17.8 mm internal diameter at the opening are used as WVTR test vials. Each test vial is filled with distilled water accurately to a level 25.0 mm±0.1 mm from the upper lip of the vial's opening. The specimen is placed, inner-facing surface of the cuff downward, over the vial's opening. The specimen is gently pulled taut and secured around the vial's circumference with an elastic band. The specimen is further sealed by wrapping Teflon tape around the vial's circumference. A preferred Teflon tape is a thread sealant tape 0.25" wide available from McMaster Carr (cat. No. 4591K11) or equivalent. The Teflon tape is applied up to the top edge of the vial but should not cover any portion of the vial's opening. The mass of the vial assembly (vial+specimen+ sealing tape) is weighed to the nearest 0.0001 gram. This is the starting mass.

The vial assemblies are placed upright in a mechanical convection oven (e.g. Lindberg/BlueM oven available from ThermoScientific or equivalent) maintained at 38±1° C. for 24 hours, taking care to avoid contact between the water in the vials and the specimens. After 24 hours has elapsed, the vial assemblies are removed from the oven and allowed to come to room temperature. The mass of each vial assembly is measured to the nearest 0.0001 gram. This is the final mass.

The WVTR is calculated using the following equation:

WVTR (g/m$^2$/24 hrs)=([starting mass (g)−final mass (g)]/surface area (m$^2$))/24 hrs Specimens from five identical articles (10 inner cuff (5 left and 5 right) and 10 outer cuff (5 left and 5 right)) are analyzed and their WVTR results recorded. The average WVTR for the inner cuffs and the outer cuffs are each reported separately to the nearest 1 g/m$^2$/24 hrs.

Air Permeability Test

Air permeability is tested using a TexTest FX3300 Air Permeability Tester (available from Advanced Testing Instruments, Greer, S.C.) with a custom made 1 cm$^2$ circular aperture (also available from Advanced Testing Instruments) or equivalent instrument. The instrument is calibrated according to the manufacturer's procedures. All testing is performed in a room maintained at 23° C.±2 C° and 50%±2% relative humidity.

The articles are pre-conditioned at 23° C.±2 C° and 50%±2% relative humidity for two hours prior to testing. To obtain a specimen, the article is stretched flat on a bench, body facing surface upward, and the total longitudinal length of the article is measured. A testing site on the inner and outer cuffs is selected at the longitudinal midpoint of the article. Using scissors, a test specimen is cut 60 mm long by the entire height of the inner cuff centered at the longitudinal midpoint of the left cuff. Next, a second test specimen is cut, this time from the outer cuff, 60 mm long by the entire height of the outer cuff, centered at the longitudinal midpoint of the left outer cuff. In like fashion, inner and outer cuff specimens are prepared from the cuffs on the right side of the article.

The specimen is centered over the measurement port. The specimen should completely cover the port with the surface corresponding to the inward-facing surface of the cuff directed toward the port. The specimen is gently extended in its longitudinal direction until taut so that the cuff lies flat across the port. Adhesive tape is applied to secure the cuff across the port in its extended state for testing. Tape should not cover any portion of the measurement port. The test pressure is set to allow air to pass through the specimen. For non-woven cuffs the pressure is typically set for 125 Pa and for cuffs containing films typically 2125 Pa is used. The sample ring is closed and the measuring range is adjusted until the range indicator shows green to indicate that the measurement is within the accepted limits of the instrument. The air permeability is recorded to the nearest 0.1 m$^3$/m$^2$/ min.

Hydrostatic Head Test

Hydrostatic head is tested using a TexTest FX3000 Hydrostatic Head Tester (available from Advanced Testing Instruments, Greer, S.C.) with a custom made 1.5 cm$^2$ circular measurement port (also available from Advanced Testing Instruments). Two annular sleeve rings, the same dimensions as the gaskets around the measurement ports, are cut from the standard protective sleeves for fine nonwovens (part FX3000-NWH, available from Advanced Testing Instruments). The sleeve rings are then adhered with two-sided adhesive tape to the sample facing surfaces of the upper and lower gaskets of the TexTest instrument to protect the specimen during clamping. Standardize the instrument according to the manufacturer's procedures. All testing is performed in a room maintained at about 23° C.±2 C° and about 50%±2% relative humidity.

Precondition the articles at about 23° C.±2 C° and about 50%±2% relative humidity for two hours prior to testing. To obtain a specimen, lay the article stretched flat on a bench, body facing surface upward, and measure the total longitudinal length of the article. Select a testing site on the inner and outer cuffs, at the longitudinal midpoint of the article. Using scissors cut a test specimen 70 mm long by the entire height of the inner cuff centered at the longitudinal midpoint of the left cuff. Next cut a second test specimen, this time from the outer cuff, 70 mm long by the entire height of the outer cuff, centered at the longitudinal midpoint of the left outer cuff. In like fashion, prepare inner and outer cuff specimens from the cuffs on the right side of the article.

Place the specimen centered over the port of the upper test head. The specimen should completely cover the port with the surface corresponding to the outward-facing surface of the cuff directed toward the port (inner-facing surface will then be facing the water). Gently extend the specimen taut in its longitudinal direction so that the cuff lies flat against the upper test plate. Adhesive tape is applied to secure the cuff to the test plate in its extended state for testing. Tape should not cover any portion of the measurement port.

Fill the TexTest syringe with distilled water, adding the water through the measurement port of the lower test plate. The water level should be filled to the top of the lower gasket. Mount the upper test head onto the instrument and lower the test head to make a seal around the specimen. The test speed is set to 3 mbar/min for samples that have a hydrostatic head of 50 mbar or less and a speed of 60 mbar/min for samples with a hydrostatic head above 50 mbar. Start the test and observe the specimen surface to detect water droplets penetrating the surface. The test is terminated when one drop is detected on the surface of the specimen or the pressure exceeds 200 mbar. Record the pressure to the nearest 0.5 mbar or record as >200 mbar if there was no penetration detected.

A total of five identical articles (10 inner cuff and 10 outer cuff specimens) are analyzed and their hydrostatic head results recorded. Calculate and report the average hydrostatic head for the inner cuffs and the outer cuffs and report each to the nearest 0.1 mbar.

Low Surface Tension Fluid Strikethrough Time Test

The low surface tension fluid strikethrough time test is used to determine the amount of time it takes a specified quantity of a low surface tension fluid, discharged at a prescribed rate, to fully penetrate a sample of a web (and other comparable barrier materials) which is placed on a reference absorbent pad.

For this test, the reference absorbent pad is 5 plies of Ahlstrom grade 989 filter paper (10 cm×10 cm) and the test fluid is a 32 mN/m low surface tension fluid.

This test is designed to characterize the low surface tension fluid strikethrough performance (in seconds) of webs intended to provide a barrier to low surface tension fluids, such as runny BM, for example.

Lister Strikethrough Tester: The instrumentation is like described in EDANA ERT 153.0-02 section 6 with the following exception: the strike-through plate has a star-shaped orifice of 3 slots angled at 60 degrees with the narrow slots having a 10.0 mm length and a 1.2 mm slot width. This equipment is available from Lenzing Instruments (Austria) and from W. Fritz Metzger Corp (USA). The unit needs to be set up such that it does not time out after 100 seconds.

Reference Absorbent Pad: Ahlstrom Grade 989 filter paper, in 10 cm×10 cm areas, is used. The average strike-through time is 3.3+0.5 seconds for 5 plies of filter paper using the 32 mN/m test fluid and without the web sample. The filter paper may be purchased from Empirical Manufacturing Company, Inc. (EMC) 7616 Reinhold Drive Cincinnati, Ohio 45237.

Test Fluid: The 32 mN/m surface tension fluid is prepared with distilled water and 0.42+/−0.001 g/liter Triton-X 100. All fluids are kept at ambient conditions.

Electrode-Rinsing Liquid: 0.9% sodium chloride (CAS 7647-14-5) aqueous solution (9 g NaCl per 1 L of distilled water) is used.

Test Procedure

All testing is performed in a room maintained at about 23° C.±2 C° and about 50%±2% relative humidity. The Ahlstrom filter paper and test articles are conditioned in this controlled environment for 24 hours and 2 hours before testing.

Ensure that the surface tension is 32 mN/m+/−1 mN/m. Otherwise remake the test fluid.

Prepare the 0.9% NaCl aqueous electrode rinsing liquid.

Ensure that the strikethrough target (3.3+/−0.5 seconds) for the Reference Absorbent Pad is met by testing 5 plies with the 32 mN/m test fluid as follows:

Neatly stack 5 plies of the Reference Absorbent Pad onto the base plate of the strikethrough tester.

Place the strikethrough plate over the 5 plies and ensure that the center of the plate is over the center of the paper. Center this assembly under the dispensing funnel.

Ensure that the upper assembly of the strikethrough tester is lowered to the pre-set stop point.

Ensure that the electrodes are connected to the timer.

Turn the strikethrough tester "on" and zero the timer.

Using the 5 mL fixed volume pipette and tip, dispense 5 mL of the 32 mN/m test fluid into the funnel.

Open the magnetic valve of the funnel (by depressing a button on the unit, for example) to discharge the 5 mL of test fluid. The initial flow of the fluid will complete the electrical circuit and start the timer. The timer will stop when the fluid has penetrated into the Reference Absorbent Pad and fallen below the level of the electrodes in the strikethrough plate.

Record the time indicated on the electronic timer.

Remove the test assembly and discard the used Reference Absorbent Pad. Rinse the electrodes with the 0.9% NaCl aqueous solution to "prime" them for the next test. Dry the depression above the electrodes and the back of the strikethrough plate, as well as wipe off the dispenser exit orifice and the bottom plate or table surface upon which the filter paper is laid.

Repeat this test procedure for a minimum of 3 replicates to ensure the strikethrough target of the Reference Absorbent Pad is met. If the target is not met, the Reference Absorbent Pad may be out of spec and should not be used.

After the Reference Absorbent Pad performance has been verified, nonwoven web samples may be tested.

Precondition the test articles at about 23° C.±2 C° and about 50%±2% relative humidity for two hours prior to testing. To obtain a specimen, lay the article stretched flat on a bench, body facing surface upward, and measure the total longitudinal length of the article. Select a testing site on the inner and outer cuffs, at the longitudinal midpoint of the article. Using scissors cut a test specimen 70 mm long by the entire height of the inner cuff centered at the longitudinal midpoint of the left cuff. Next cut a second test specimen, this time from the outer cuff, 70 mm long by the entire height of the outer cuff, centered at the longitudinal midpoint of the left outer cuff. In like fashion, prepare inner and outer cuff specimens from the cuffs on the right side of the article.

Place the specimen centered over the port of the strike through plate. The specimen should completely cover the port with the surface corresponding to the body-facing surface of the cuff directed toward the port. Gently extend the specimen taut in its longitudinal direction so that the cuff lies flat against the upper test plate. Adhesive tape is applied to secure the cuff to the test plate in its extended state for testing. Tape should not cover any portion of the measurement port.

Ensure that the upper assembly of the strikethrough tester is lowered to the pre-set stop point.

Ensure that the electrodes are connected to the timer. Turn the strikethrough tester "on" and zero the timer.

Run as described above.

Repeat this procedure for three articles. Average the six values and report as the 32 mN/m low surface tension strikethrough time to the nearest 0.1 seconds.

Chassis Contraction Method

The chassis contraction is measured using a calibrated ruler capable of measuring to ±1 mm, (traceable to National standards such as NIST), and a force gauge capable of measuring an applied force of 500 g accurately to ±0.5 g (a suitable gauge is the Chatillon DFS series, available from Ametek, Largo, Fla.). A spring loaded clamp, with contact faces 60 mm wide by 10 mm deep, is attached to the force gauge to hold the test article. All testing is performed in a room maintained at about 23±2° C. and about 50±2% relative humidity. All samples were conditioned for 2 hours before testing at about 23±2° C. and about 50±2% relative humidity.

For this measure the chassis is identified as the portion of the article with contiguous back sheet and does not include any attached tabs or attached elastic tabs/ears. Unfold the absorbent article taking care not to stretch the waist features. Place it on a horizontal bench surface with the back sheet facing the bench and the top sheet facing upward. If present, unfold and lie flat any tabs or ears attached to the back half of the article. Identify the back waist feature of the article. With the article flat against the bench, lay the calibrated ruler along the article aligning it with the lateral midline of the waist feature. Measure the lateral distance from the right distal edge of the chassis to the left distal edge of the chassis and record to the nearest 1 mm. This is the Relaxed Back Chassis Width (RBCW)

Attach the force gauge to the right distal edge of the chassis. As attached, the force gauge is oriented to pull from left to right. The grip faces are parallel to the longitudinal axis of the article, centered at the lateral midline of the waist feature, with 3 mm of the chassis within the grip faces.

Adhere a piece of 2-sided adhesive tape 50 mm in width by 900 mm long to the bench. Hold the article with the back sheet directed toward the taped surface with the back waist parallel to the long dimension of the tape. Align the lateral midline of the waist feature with the lateral midline of the tape strip. Secure the first 3 mm of the left chassis edge to the adhesive tape. Using the force gauge, extend the back waist to an applied force of 500 g. Next lower the article and adhere the article's back waist to the adhesive tape across the lateral width of the chassis. Remove the force gauge from the chassis. Lay the ruler across the article aligning it along the lateral midline of the waist feature. Measure the lateral distance from the right distal edge of the chassis to the left distal edge of the chassis and record to the nearest 1 mm. This is the Extended Back Chassis Width (EBCW).

Repeat this measure in like fashion for the front waist feature of the article to determine the Relaxed Front Chassis Width (RFCW) and the Extended Front Chassis Width (EFCW). Calculate the Chassis Contractions as follows:

Back Chassis Contraction (% BCC)=(EBCW−RBCW)/EBCW×100%

Front Chassis Contraction (% FCC)=(EFCW−RFCW)/EFCW×100

Front-to-Back Delta Chassis Contraction=absolute value of (% BCC−% FCC)

Waist Feature Calipers

Calipers were performed using an Ono Sokki digital caliper (GS-503 Linear Gauge Sensor with DG-3610 Digital Gauge, Ono Sokki Co, Japan) capable of measuring to 0.01 mm. The foot diameter is 1 cm and the applied pressure is 0.5 psi. Readings are taken after a residence time of 5 sec. Linear measurements are made using a calibrated ruler capable of measuring to ±1 mm (traceable to National standards such as NIST). A stainless steel plate, uniformly 1.5 mm thick±0.1 mm, 20 cm wide and 40 cm long is used for mounting the extended waist. All testing is performed in a room maintained at about 23±2° C. and about 50±2% relative humidity. All samples are conditioned for 2 hours before testing at about 23±2° C. and about 50±2% relative humidity.

Relaxed Waist Calipers

Unfold an absorbent article taking care not to stretch the waist features. Place it on a horizontal bench surface with the back sheet facing the bench and the top sheet facing upward. If present, unfold and lie flat any tabs or ears attached to the back half of the article. Identify the back waist feature of the article. Using a calibrated ruler measure the lateral width of the waist feature along its longitudinal midline. This is the Relaxed Length of the waist feature (RWL) Mark the waist feature along its midline at 50% of its lateral width. This is waist site 1 (WS1). Measure and mark two more sites, the first 1.5 cm to the left of the 50% mark (WS2) and the second 1.5 cm to the right of the 50% mark (WS3).

Place the caliper on the anvil and zero the digital controller. Place the article on the anvil, with the top sheet facing upward, and use the caliper to measure the thickness at WS1, WS2, and WS3. Report to the nearest 0.01 mm as the Relaxed Waist Caliper RWC1, RWC2, and RWC3 respectively.

Using a cryogenic freeze spray (available as CytoFreeze, Control Company, TX) gently remove the elastic feature from the article. Place the article on the anvil, with the top sheet facing upward, and use the caliper to measure the thickness of the article corresponding to WS1, WS2, and WS3. Report to the nearest 0.01 mm as Relaxed Back Sheet Caliper RBC1, RBC2, RBC3 respectively.

Calculate the Waist Feature Caliper as:

Relaxed Waist Feature Caliper=[(RWC1−RBC1)+(RWC2−RBC2)+(RWC3−RBC3)]/3

Repeat this procedure for three identical articles and report as the average to the nearest 0.01 mm.

Extended Waist Calipers

Unfold an absorbent article taking care not to stretch the waist features. Assemble a vertical ring stand which supports a horizontal bar. Attach a spring loaded clamp to the left edge of the chassis, centered on the waist feature. Attach the clamp to the horizontal support so that the waist feature hangs vertically. Attach a second clamp, which has a mass of 300 g±1 g, to the right edge of the chassis, centered on the midline of the waist feature. Allow the article to hang for 30 seconds and then using the calibrated ruler measure the extended length of the waist feature to the nearest 1 mm. This is the Chassis Extended Length (CEL). The CEL can be used for all extended waist measures.

Unfold another absorbent article taking care not to stretch the waist features. Place it on a horizontal bench surface with the back sheet facing the bench and the top sheet facing upward. If present, unfold and lie flat any tabs or ears attached to the back half of the article. Identify the back waist feature of the article. Using a calibrated ruler measure the lateral width of the waist feature along its longitudinal midline. This is the Relaxed Length of the waist feature (RWL) Mark the waist feature along its midline at 50% of its lateral width. This is waist site 1 (WS1). Measure and mark two more sites, the first 1.5 cm to the left of the 50% mark (WS2) and the second 1.5 cm to the right of the 50% mark (WS3). Identify the proximal edge of the waist feature, i.e. the edge closest to the crotch of the article. Mark a lateral line 1.5 cm from the proximal edge toward the crotch, and parallel to the waist feature. Along a longitudinal axis that passes through WS1, mark the intersection at the lateral line just drawn (AS1). Repeat in like fashion for WS2 and WS3 to define sites AS2 and AS3 respectively.

Place the article, top sheet facing upward, onto the stainless steel plate. Secure the left distal edge of the chassis at the waist feature's midline to the steel plate with adhesive tape. Grasp the right side of the chassis and pull until the waist feature has been extended equal to the Chassis Extended Length (CEL). Secure the right side of the chassis to the steel plate with adhesive tape.

Place the steel plate with attached article on the anvil of the caliper. Place the caliper foot on a region of the steel plate that is not covered by the article and zero the digital control. Using the caliper, measure the thickness at the six marked sites. Report to the nearest 0.01 mm as Extended Waist Caliper EWC1, EWC2, and EWC3. Using a cryogenic freeze spray gently remove the elastic feature from the article. Place the steel plate with attached article on the anvil of the caliper and measure the thickness of the article at the sites corresponding to WS1, WS2 and WS3. Report to the nearest 0.01 mm as Extended Back Sheet Caliper EBC1, EBC2, EBC3 respectively.

Calculate the Waist Feature Calipers as:

Extended Waist Feature Caliper=[(EWC1−EBC1)+ (EWC2−EBC2)+(EWC3−EBC3)]/3

Repeat this procedure for three identical articles and report as the average to the nearest 0.01 mm.

Waist Feature Percent Consolidation

Linear measurements are made using a calibrated ruler capable of measuring to ±1 mm (traceable to National standards such as NIST). All testing is performed in a room maintained at about 23±2° C. and about 50±2% relative humidity. All samples are conditioned for 2 hours before testing at about 23±2° C. and about 50±2% relative humidity.

Unfold the absorbent article taking care not to stretch the waist features. Place it on a horizontal bench surface with the back sheet facing the bench and the top sheet facing upward. If present, unfold and lie flat any tabs or ears attached to the back half of the article. Identify the back waist feature of the article. Using a calibrated ruler measure the lateral width of the waist feature along its midline and record to the nearest 1 mm. This is the Relaxed Length of the waist feature (RWL).

Using a cryogenic freeze spray (available as CytoFreeze, Control Company, TX) carefully remove the waist feature from the article. Place the waist feature into a beaker with 100 mL of dichloromethane and soak for 15 minutes to dissolve the adhesives. Remove the waist feature from the solvent and remove the elastics. Lay the waist feature substrate flat in a fume hood to dry. Assemble a vertical ring stand which supports a horizontal bar. Attach a spring loaded clamp, which is at least as wide as the waist feature, to the left edge of the waist feature. Attach the clamp to the horizontal support so that the waist feature hangs vertically. Attach a second clamp, which has a mass of 3 g±1 g and is at least as wide as the waist feature, to the right edge of the waist feature. Allow the article to hang for 30 seconds and then using the calibrated ruler measure the extended length of the waist feature to the nearest 1 mm. This is the Extended Waist Feature Length (EWL).

Calculate the Full Waistband Consolidation as:

% Full Waistband Consolidation=((EWL−RWL)/ RWL)×100

Repeat this procedure for three identical articles and report as the average to the nearest 1 mm. Calculate the Extended Waistband Consolidation as:

% Extended Waistband Consolidation=((EWL− RWL)/RWL)×100−((1−((CEL−RWL)/CEL)) *100)

Repeat this procedure for three identical articles and report as the average to the nearest 1 mm.

Frequency of Waistband and Outer Leg Cuff Gathers on Taped Diaper Products

Figure 10:
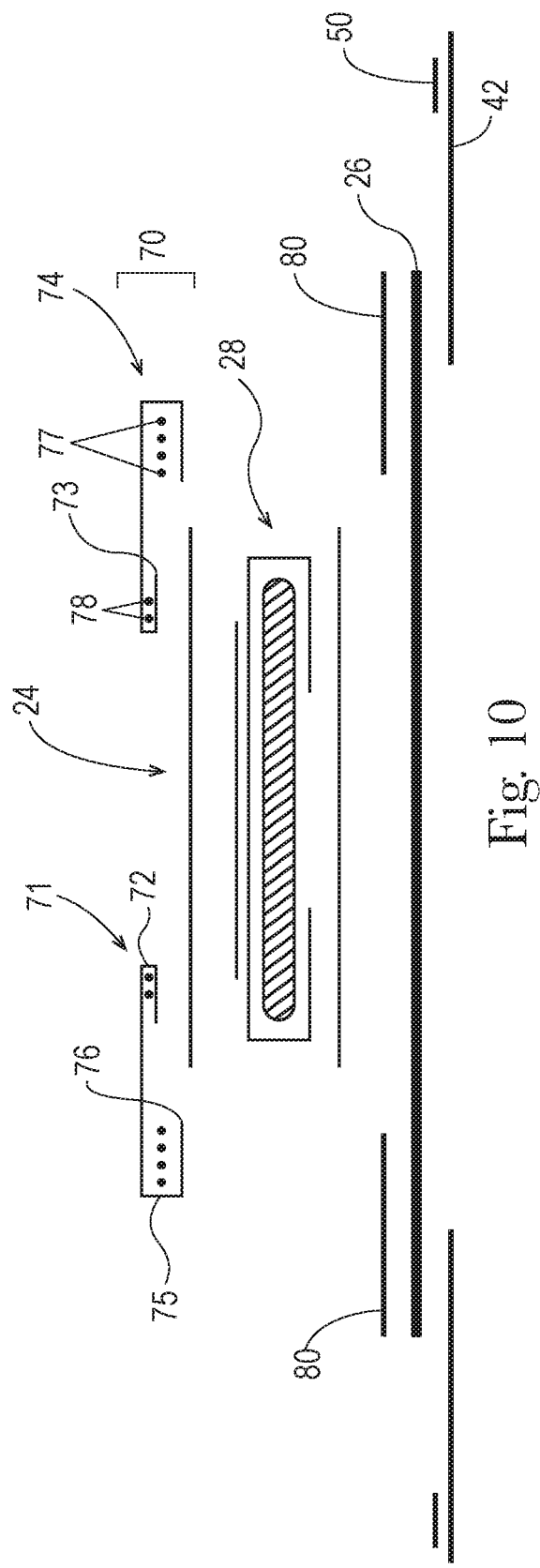
FIG. 10 is a schematic cross sectional view of an absorbent article as described herein.

In the visual center of the waistband on the diaper both CD and MD, report the number of gathers per 30 mm on both taped end (TE) and un-taped end (UTE). Hold in place the measuring template, as shown in FIG. 10, then count the gather peaks within the 30 mm window on the template. Make sure not to stretch the gathers. Perform this on both the taped (TE) inside and outside and then repeat on the un-taped end (UTE) inside and outside of the product. Report the number of gathers within the 30 mm.

In the visual center of the Leg Gasketing System gather on the diaper both CD and MD, report the number of gathers per 30 mm on both Baby right and Baby left. Hold in place the measuring template then count the number of gathers within the 30 mm window on the template. Make sure not to stretch the gathers. Perform this on both Baby right and Baby left of the product both CD and MD. Report the number of gathers within the 30 mm.

Calculate the Ratio of Leg Gasketing System Gather Count to Waistband Gather Count as follows:

Ratio=Average Leg Gasketing System Gather Count/ Average Waistband Gather Count

Repeat this procedure for three identical articles and report as the average.

CD Length Ratio

CD Length Ratio is the ratio of chassis extended length (CEL) to Extended Back Chassis Width (EBCW), as defined here.

Calculate the CD Length Ratio as follows:

CD Length Ratio=CEL/EBCW

Repeat this procedure for three identical articles and report as the average.

Packaging:

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 36:
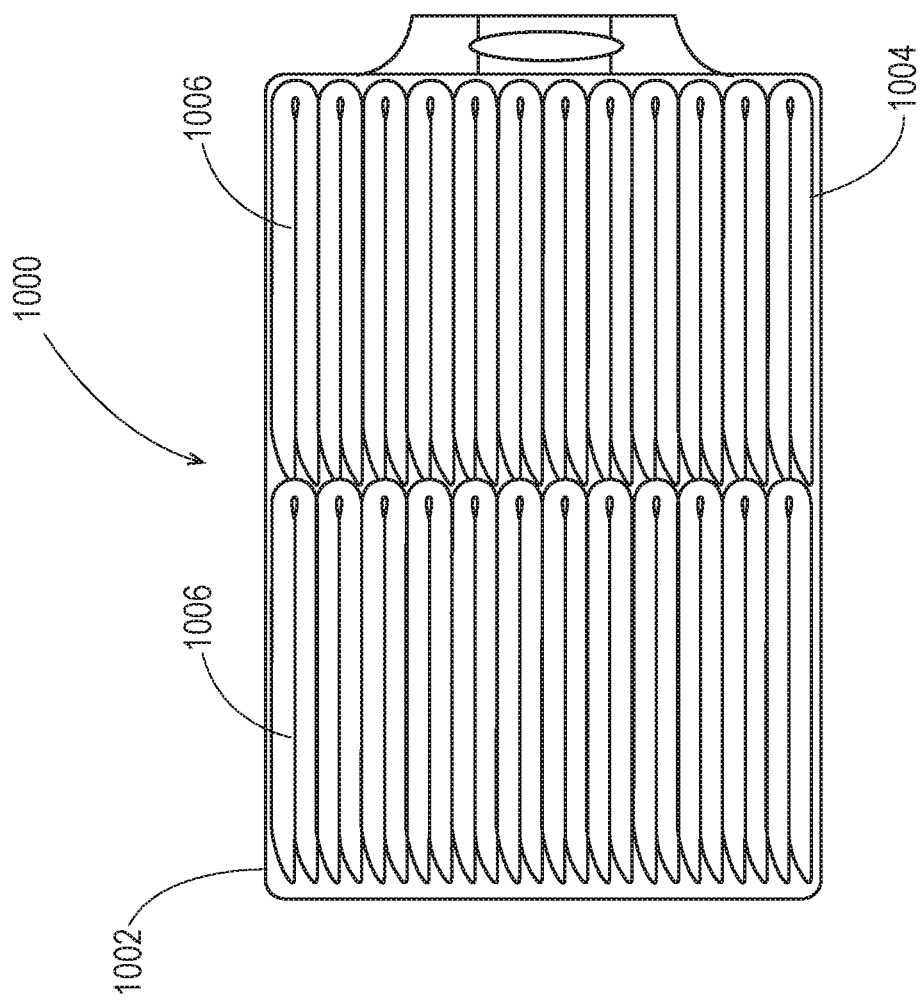
FIG. 36 is a schematic cross sectional view of a package of absorbent articles as detailed herein.

FIG. 36 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 36). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Examples

A. A disposable absorbent article for wearing about the lower torso of a wearer, the disposable absorbent article comprising: a first waist region, a second waist region, a crotch region disposed between the first and second waist regions; a first waist edge and a second waist edge; and a first longitudinal edge and a second longitudinal edge; wherein the disposable absorbent article comprises a chassis comprising:
1.) a topsheet;
2.) a backsheet; and
3.) an absorbent core disposed between the topsheet and the backsheet;
wherein the disposable absorbent article further comprises a leg gasketing system;
wherein the leg gasketing system comprises a web of material forming an inner cuff and an outer cuff;
wherein the inner cuff comprises an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge;
wherein at least a portion of the web of material between the outer cuff folded edge and the outer cuff material edge is attached to the chassis in the first waist region, the second waist region and the crotch region; and at least a portion of the web of material between the inner cuff folded edge and the outer cuff folded edge is attached to the chassis in the crotch region and the first waist region; and the web of material between the inner cuff folded edge and the outer cuff folded edge is unattached to the chassis in at least a portion of the second waist region, forming a leg gasketing system pocket with an opening on an inboard longitudinal edge of the leg gasketing system pocket;
wherein the absorbent core comprises superabsorbent polymer enclosed within a core wrap, wherein the superabsorbent polymer is disposed on an absorbent material deposition area within the core wrap and the absorbent material deposition area comprises at least one channel which is at least partially oriented in the longitudinal direction of the disposable absorbent article.

B. The disposable absorbent article of Paragraph A, wherein the opening of the leg gasketing system pocket measures between 5 mm and 100 mm in the longitudinal direction.

C. The disposable absorbent article of any one of Paragraphs A-B, wherein the leg gasketing system does not comprise a polymeric film.

D. The disposable absorbent article of any one of Paragraphs A-C, wherein the leg gasketing system comprises an N-fiber material.

E. The disposable absorbent article of any one of Paragraphs A-D, wherein the leg gasketing system is comprised of one web of material.

F. The disposable absorbent article of any one of Paragraphs A-E, wherein the leg gasketing system extends from the first waist edge to the second waist edge.

G. The disposable absorbent article of any one of Paragraphs A-F, wherein the absorbent material deposition area comprises at least two channels.

H. The disposable absorbent article of any one of Paragraphs A-G, further comprising a liquid management system.

I. The disposable absorbent article of Paragraph H, wherein the liquid management system comprises at least one liquid management system channel.

J. The disposable absorbent article of Paragraph H, wherein the liquid management system comprises at least two liquid management system channels.

K. The disposable absorbent article of any one of Paragraphs H-J, wherein the at least one channel partially aligns with the at least one liquid management system channel.

L. A disposable absorbent article for wearing about the lower torso of a wearer, the disposable absorbent article comprising: a first waist region, a second waist region, a crotch region disposed between the first and second waist regions; a first waist edge and a second waist edge; and a first longitudinal edge and a second longitudinal edge; wherein the disposable absorbent article comprises a chassis comprising:
1.) a topsheet;
2.) a backsheet;
3.) an absorbent core disposed between the topsheet and the backsheet; and
4.) a liquid management system adjacent to the absorbent core;

wherein the disposable absorbent article further comprises a leg gasketing system;
wherein the leg gasketing system comprises a web of material forming an inner cuff and an outer cuff;
wherein the inner cuff comprises an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge;
wherein at least a portion of the web of material between the outer cuff folded edge and the outer cuff material edge is attached to the chassis in the first waist region, the second waist region and the crotch region; and at least a portion of the web of material between the inner cuff folded edge and the outer cuff folded edge is attached to the chassis in the crotch region and the first waist region; and the web of material between the inner cuff folded edge and the outer cuff folded edge is unattached to the chassis in at least a portion of the second waist region, forming a leg gasketing system pocket with an opening on an inboard longitudinal edge of the leg gasketing system pocket;
wherein the absorbent core comprises superabsorbent polymer enclosed within a core wrap, wherein the superabsorbent polymer is disposed on an absorbent material deposition area within the core wrap and the absorbent material deposition area comprises at least one channel which is at least partially oriented in the longitudinal direction of the disposable absorbent article; and
wherein the liquid management system comprises at least one liquid management system channel, and wherein the at least one channel of the absorbent core aligns with the at least one liquid management system channel.

M. The disposable absorbent article of Paragraph L, wherein the absorbent material deposition area comprises at least two channels.

N. The disposable absorbent article of any one of Paragraphs L-M, wherein the liquid management system comprises at least two channels.

O. A disposable absorbent article for wearing about the lower torso of a wearer, the disposable absorbent article comprising: a first waist region, a second waist region, a crotch region disposed between the first and second waist regions; a first waist edge and a second waist edge; and a first longitudinal edge and a second longitudinal edge; wherein the disposable absorbent article comprises a chassis comprising:
1.) a topsheet;
2.) a backsheet; and
3.) an absorbent core disposed between the topsheet and the backsheet;
wherein the disposable absorbent article further comprises a leg gasketing system;
wherein the leg gasketing system comprises a web of material forming an inner cuff and an outer cuff;
wherein the inner cuff comprises an inner cuff folded edge and an inner cuff material edge and the outer cuff comprises an outer cuff folded edge and an outer cuff material edge, such that the web of material is folded laterally inward to form the outer cuff folded edge and folded laterally outward to form the inner cuff folded edge;
wherein the leg gasketing system extends from the first waist edge to the second waist edge; and at least a portion of the web of material between the outer cuff folded edge and the outer cuff material edge is attached to the chassis in the first waist region, the second waist region and the crotch region; and at least a portion of the web of material between the inner cuff folded edge and the outer cuff folded edge is attached to the chassis in the crotch region and the first waist region;
wherein the outer cuff comprises an elastics adhesive and at least one longitudinally oriented elastic member running parallel to the outer cuff folded edge, the elastics adhesive and at least one elastic member disposed between 1) the web of material between the outer cuff folded edge and the outer cuff material edge and 2) the web of material between the outer cuff folded edge and the inner cuff folded edge;
wherein in at least a portion of the second waist region, the outer cuff is free of elastics adhesive and elastic members, thus forming a leg gasketing system pocket between 1) the web of material between the outer cuff folded edge and the outer cuff material edge and 2) the web of material between the outer cuff folded edge and the inner cuff folded edge, the leg gasketing system pocket having an outboard longitudinal edge at the outer cuff folded edge;
wherein the leg gasketing system pocket comprises an opening on an inboard longitudinal edge of the leg gasketing system pocket; and
wherein the absorbent core comprises superabsorbent polymer enclosed within a core wrap, wherein the superabsorbent polymer is disposed on an absorbent material deposition area within the core wrap and the absorbent material deposition area comprises at least one channel which is at least partially oriented in the longitudinal direction of the disposable absorbent article.

P. The disposable absorbent article of Paragraph O, wherein the absorbent material deposition area comprises at least two channels.

Q. The disposable absorbent article of any one of Paragraphs O-P, further comprising a liquid management system.

R. The disposable absorbent article of Paragraph Q, wherein the liquid management system comprises at least one liquid management system channel.

S. The disposable absorbent article of any one of Paragraphs Q-R, wherein the at least one channel partially aligns with the at least one liquid management system channel.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article for wearing about the lower torso of a wearer, the disposable absorbent article comprising:
   a first waist region;
   a second waist region;
   a crotch region disposed between the first and second waist regions;
   a first waist edge;
   a second waist edge;
   a first longitudinal edge;
   a second longitudinal edge;
   a chassis comprising:
      a topsheet;
      a backsheet; and
      an absorbent core disposed between the topsheet and the backsheet;
   a waistband disposed in the second waist region and comprising:
      a waistband elastic member;
      a distal lateral edge disposed inboard of the second waist edge of the absorbent article; and
      a proximal lateral edge disposed between the distal lateral edge and the crotch region; and
   a leg gasketing system comprising:
      a web of material forming an inner cuff and an outer cuff;
      wherein the inner cuff comprises an inner cuff folded edge and an inner cuff material edge, and wherein the outer cuff comprises an outer cuff folded edge and an outer cuff material edge, such that the web of material is folded laterally inward to form the outer cuff folded edge and folded laterally outward to form the inner cuff folded edge;
      wherein at least a portion of the web of material between the outer cuff folded edge and the outer cuff material edge is attached to the chassis in the first waist region, the second waist region and the crotch region, wherein at least a portion of the web of material between the inner cuff folded edge and the outer cuff folded edge is attached to the chassis in the crotch region and the first waist region, and wherein the web of material between the inner cuff folded edge and the outer cuff folded edge is unattached to the chassis in at least a portion of the second waist region, forming a leg gasketing system pocket with an opening on an inboard longitudinal edge of the leg gasketing system pocket; and
      wherein the absorbent core comprises superabsorbent polymer enclosed within a core wrap, and wherein the superabsorbent polymer is disposed on an absorbent material deposition area within the core wrap and the absorbent material deposition area comprises at least one channel which is at least partially oriented in a longitudinal direction of the disposable absorbent article.

2. The disposable absorbent article of claim 1, wherein the waistband elastic member comprises a film.

3. The disposable absorbent article of claim 2, wherein the waistband is disposed between the topsheet and the backsheet.

4. The disposable absorbent article of claim 1, comprising a garment-facing surface and a body-facing surface, wherein the waistband comprises a first waistband nonwoven, and wherein the waistband is disposed on the garment-facing surface of the disposable absorbent article.

5. The disposable absorbent article of claim 4, wherein the waistband elastic member comprises a film.

6. The disposable absorbent article of claim 4, wherein the waistband elastic member comprises an elastic strand.

7. The disposable absorbent article of claim 1, comprising a garment-facing surface and a body-facing surface, wherein the waistband comprises a first waistband nonwoven, and wherein the waistband is disposed on the body-facing surface of the disposable absorbent article.

8. The disposable absorbent article of claim 7, wherein the waistband elastic member comprises a film.

9. The disposable absorbent article of claim 7, wherein the waistband elastic member comprises an elastic strand.

10. A disposable absorbent article for wearing about the lower torso of a wearer, the disposable absorbent article comprising:
   a first waist region;
   a second waist region;
   a crotch region disposed between the first and second waist regions;
   a first waist edge;
   a second waist edge;
   a first longitudinal edge;
   a second longitudinal edge;
   a chassis comprising:
      a topsheet;
      a backsheet;
      an absorbent core disposed between the topsheet and the backsheet;
   a waistband disposed in the second waist region and comprising:
      a waistband elastic member;
      a distal lateral edge, wherein the distal lateral edge is coterminous with the second waist edge; and
      a proximal lateral edge disposed between the distal lateral edge and the crotch region;
   a liquid management system adjacent to the absorbent core; and
   a leg gasketing system comprising:
      a web of material forming an inner cuff and an outer cuff;
      wherein the inner cuff comprises an inner cuff folded edge and an inner cuff material edge, and wherein the outer cuff comprises an outer cuff folded edge and an outer cuff material edge, such that the web of material is folded laterally inward to form the outer cuff folded edge and folded laterally outward to form the inner cuff folded edge;
      wherein at least a portion of the web of material between the outer cuff folded edge and the outer cuff material edge is attached to the chassis in the first waist region, the second waist region and the crotch region, wherein at least a portion of the web of material between the inner cuff folded edge and the outer cuff folded edge is attached to the chassis in the crotch region and the first waist region, and wherein the web of material between the inner cuff folded edge and the outer cuff folded edge is unattached to the chassis in at least a portion of the second waist region, forming a leg gasketing system pocket with an opening on an inboard longitudinal edge of the leg gasketing system pocket;
      wherein the absorbent core comprises superabsorbent polymer enclosed within a core wrap, and wherein the superabsorbent polymer is disposed on an absorbent material deposition area within the core wrap and the absorbent material deposition area comprises at least one channel which is at least partially oriented in a longitudinal direction of the disposable absorbent article; and wherein the liquid management system comprises at least one liquid management system channel, wherein the at least one channel of the absorbent core aligns with the at least one liquid management system channel.

11. The disposable absorbent article of claim 10, wherein the waistband elastic member comprises a film.

12. The disposable absorbent article of claim 11, wherein the waistband is disposed between the topsheet and the backsheet.

13. The disposable absorbent article of claim 10, comprising a garment-facing surface and a body-facing surface, wherein the waistband comprises a first waistband nonwoven, and wherein the waistband is disposed on the garment-facing surface of the disposable absorbent article.

14. The disposable absorbent article of claim 13, wherein the waistband elastic member comprises a film.

15. The disposable absorbent article of claim 13, wherein the waistband elastic member comprises an elastic strand.

16. The disposable absorbent article of claim 10, comprising a garment-facing surface and a body-facing surface, wherein the waistband comprises a first waistband nonwoven, and wherein the waistband is disposed on the body-facing surface of the disposable absorbent article.

17. The disposable absorbent article of claim 16, wherein the waistband elastic member comprises a film.

18. The disposable absorbent article of claim 16, wherein the waistband elastic member comprises an elastic strand.

19. A disposable absorbent article for wearing about the lower torso of a wearer, the disposable absorbent article comprising:
    a first waist region;
    a second waist region;
    a crotch region disposed between the first and second waist regions;
    a first waist edge;
    a second waist edge;
    a first longitudinal edge;
    a second longitudinal edge;
    a chassis comprising:
        a topsheet;
        a backsheet; and
        an absorbent core disposed between the topsheet and the backsheet;
    a waistband disposed in the second waist region and comprising a waistband elastic member; and
    a leg gasketing system comprising:
        a web of material forming an inner cuff and an outer cuff;
    wherein the inner cuff comprises an inner cuff folded edge and an inner cuff material edge, and wherein the outer cuff comprises an outer cuff folded edge and an outer cuff material edge, such that the web of material is folded laterally inward to form the outer cuff folded edge and folded laterally outward to form the inner cuff folded edge;
    wherein the leg gasketing system extends from the first waist edge to the second waist edge;
    wherein at least a portion of the web of material between the outer cuff folded edge and the outer cuff material edge is attached to the chassis in the first waist region, the second waist region and the crotch region;
    wherein at least a portion of the web of material between the inner cuff folded edge and the outer cuff folded edge is attached to the chassis in the crotch region and the first waist region;
    wherein the outer cuff comprises an elastics adhesive and at least one longitudinally oriented elastic member running parallel to the outer cuff folded edge, the elastics adhesive and at least one elastic member disposed between: 1) the web of material between the outer cuff folded edge and the outer cuff material edge, and 2) the web of material between the outer cuff folded edge and the inner cuff folded edge;
    wherein in at least a portion of the second waist region, the outer cuff is free of elastics adhesive and elastic members, thereby forming a leg gasketing system pocket between: 1) the web of material between the outer cuff folded edge and the outer cuff material edge, and 2) the web of material between the outer cuff folded edge and the inner cuff folded edge, the leg gasketing system pocket having an outboard longitudinal edge at the outer cuff folded edge;
    wherein the leg gasketing system pocket comprises an opening on an inboard longitudinal edge of the leg gasketing system pocket; and
    wherein the absorbent core comprises superabsorbent polymer enclosed within a core wrap, and wherein the superabsorbent polymer is disposed on an absorbent material deposition area within the core wrap and the absorbent material deposition area comprises at least one channel which is at least partially oriented in the longitudinal direction of the disposable absorbent article.

20. The disposable absorbent article of claim 19, wherein the absorbent material deposition area comprises at least two channels.

* * * * *